United States Patent
Cantrell, Jr. et al.

(10) Patent No.: US 10,927,121 B1
(45) Date of Patent: Feb. 23, 2021

(54) TECHNOLOGIES FOR REMOVING RESIDUAL SOLVENT FROM NALMEFENE HYDROCHLORIDE AND PRODUCING CRYSTALLINE NALMEFENE HYDROCHLORIDE MONOHYDRATE, MONOSOLVATE, OR CRYSTALLINE NALMEFENE HYDROCHLORIDE DIHYDRATE

(71) Applicant: Southwest Research Institute, San Antonio, TX (US)

(72) Inventors: William R. Cantrell, Jr., San Antonio, TX (US); Robert D. Gutierrez, San Antonio, TX (US); Michael J. Rubal, Lytle, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 16/723,215

(22) Filed: Dec. 20, 2019

(51) Int. Cl.
 *C07D 489/08* (2006.01)
(52) U.S. Cl.
 CPC .................... *C07D 489/08* (2013.01)
(58) Field of Classification Search
 CPC ................................... C07D 489/08
 USPC ......................................... 546/44
 See application file for complete search history.

(56) References Cited

U.S. PATENT DOCUMENTS

| | | |
|---|---|---|
| 4,535,157 A | 8/1985 | Meltzer et al. |
| 8,530,495 B2 | 9/2013 | Lopez de Diego et al. |
| 8,598,352 B2 | 12/2013 | De Faveri et al. |
| 8,841,452 B1 | 9/2014 | De Faveri et al. |

FOREIGN PATENT DOCUMENTS

| | | | |
|---|---|---|---|
| CN | 105646508 A * | 6/2016 | ........ C07D 489/08 |
| CN | 106 167492 A | 11/2016 | |

OTHER PUBLICATIONS

Elliot F. Hahn; et al., Narcotic Antagonists. 4. Carbon-6 Derivatives of N-Substituted Noroxymorphones as Narcotic Antagonists, 1975, pp. 259-262, vol. 18., No. 3, Journal of Medicinal Chemistry.

* cited by examiner

*Primary Examiner* — Charanjit Aulakh
(74) *Attorney, Agent, or Firm* — Grossman Tucker Perreault & Pfleger PLLC

(57) ABSTRACT

Methods for removing residual solvent from Nalmefene Hydrochloride (HCl) and producing crystalline Nalmefene HCl monohydrate, monosolvate or crystalline Nalmefene HCl dihydrate are described. In embodiments, the methods include recrystallizing Nalmefene HCl from a solvate that includes Nalmefene HCl, water, and a first solvent, wherein the first solvent has a molar volume of at least 98 cm$^3$. Crystalline Nalmefene HCl with a desirably low amount of residual solvent is also described.

25 Claims, 50 Drawing Sheets

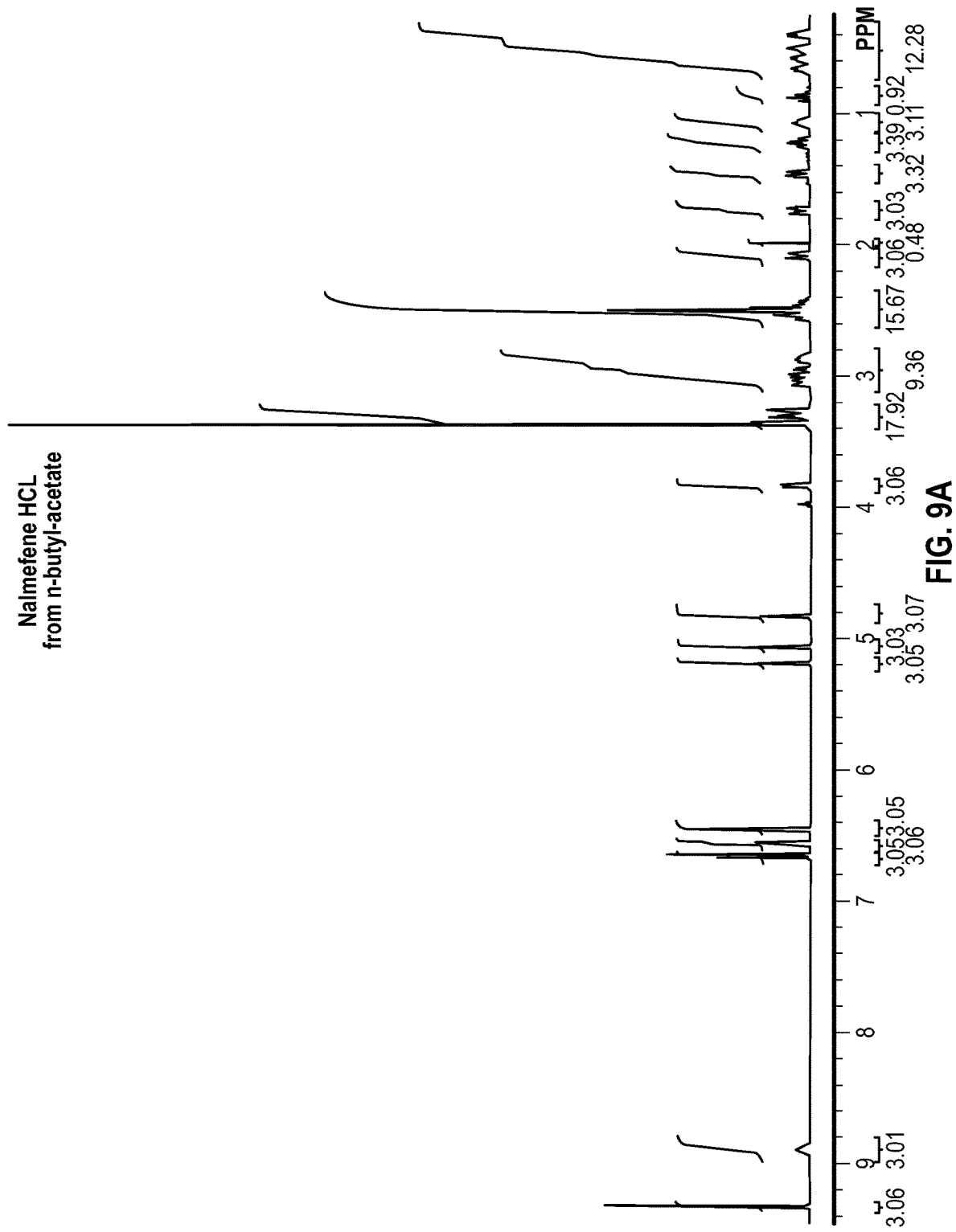

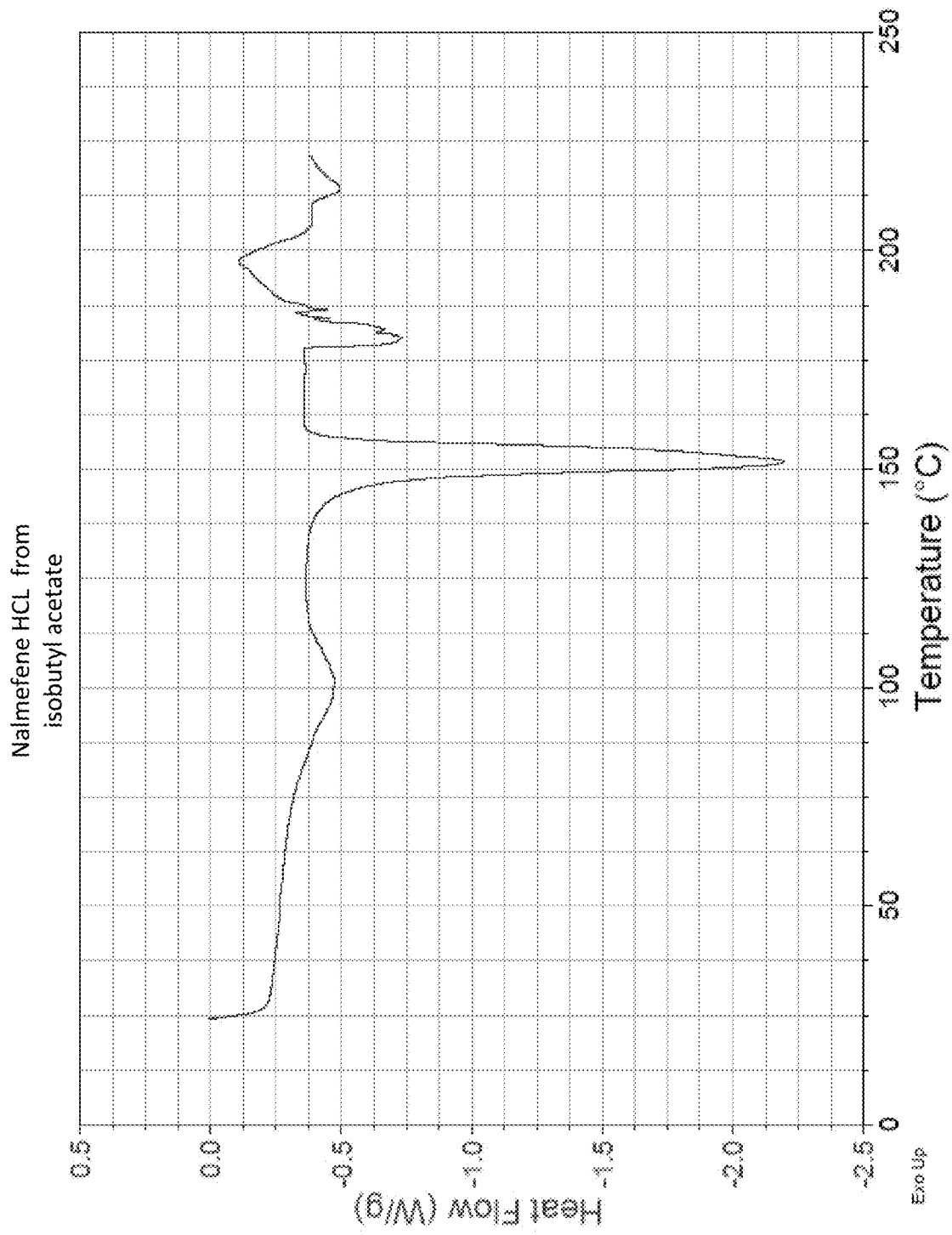

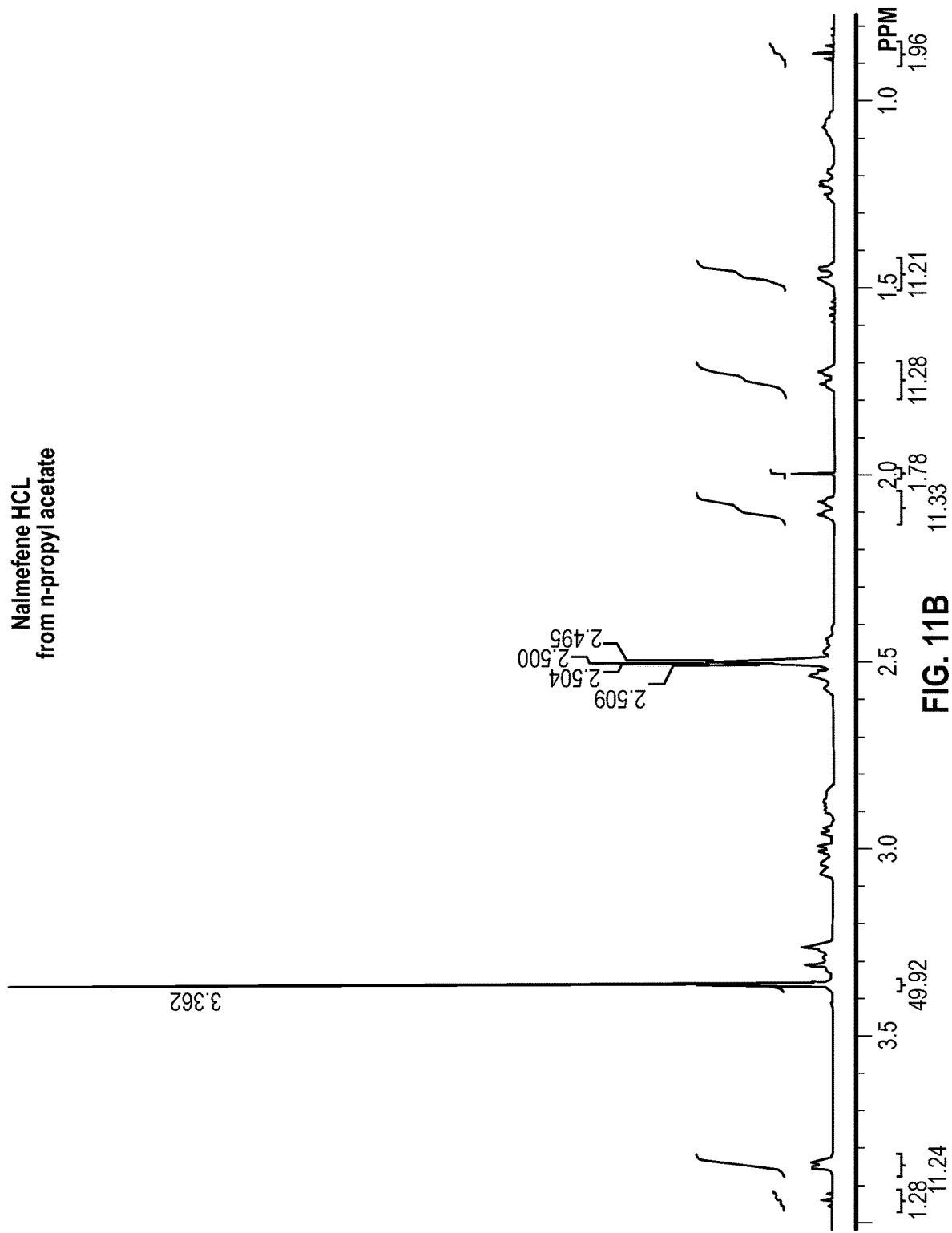

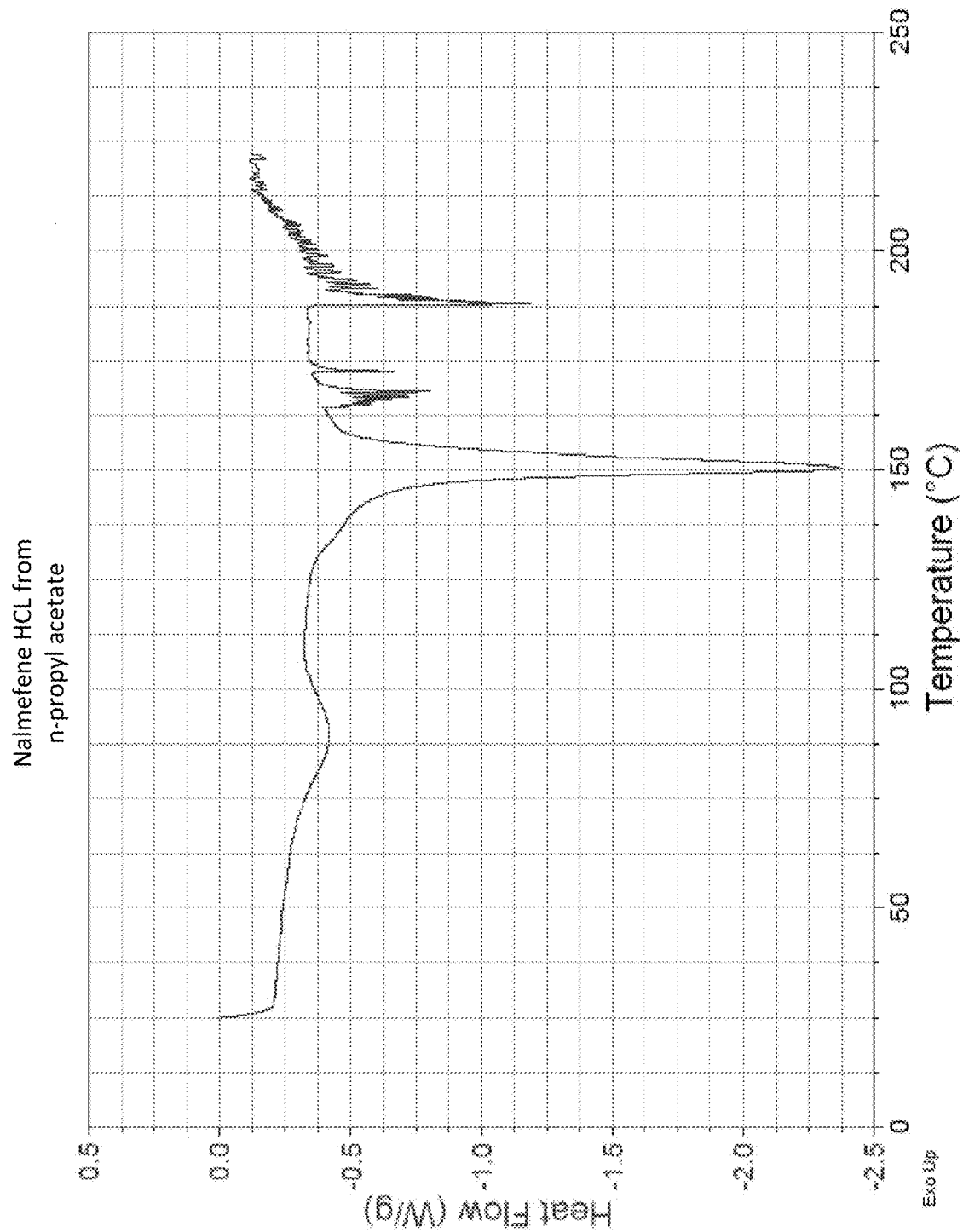

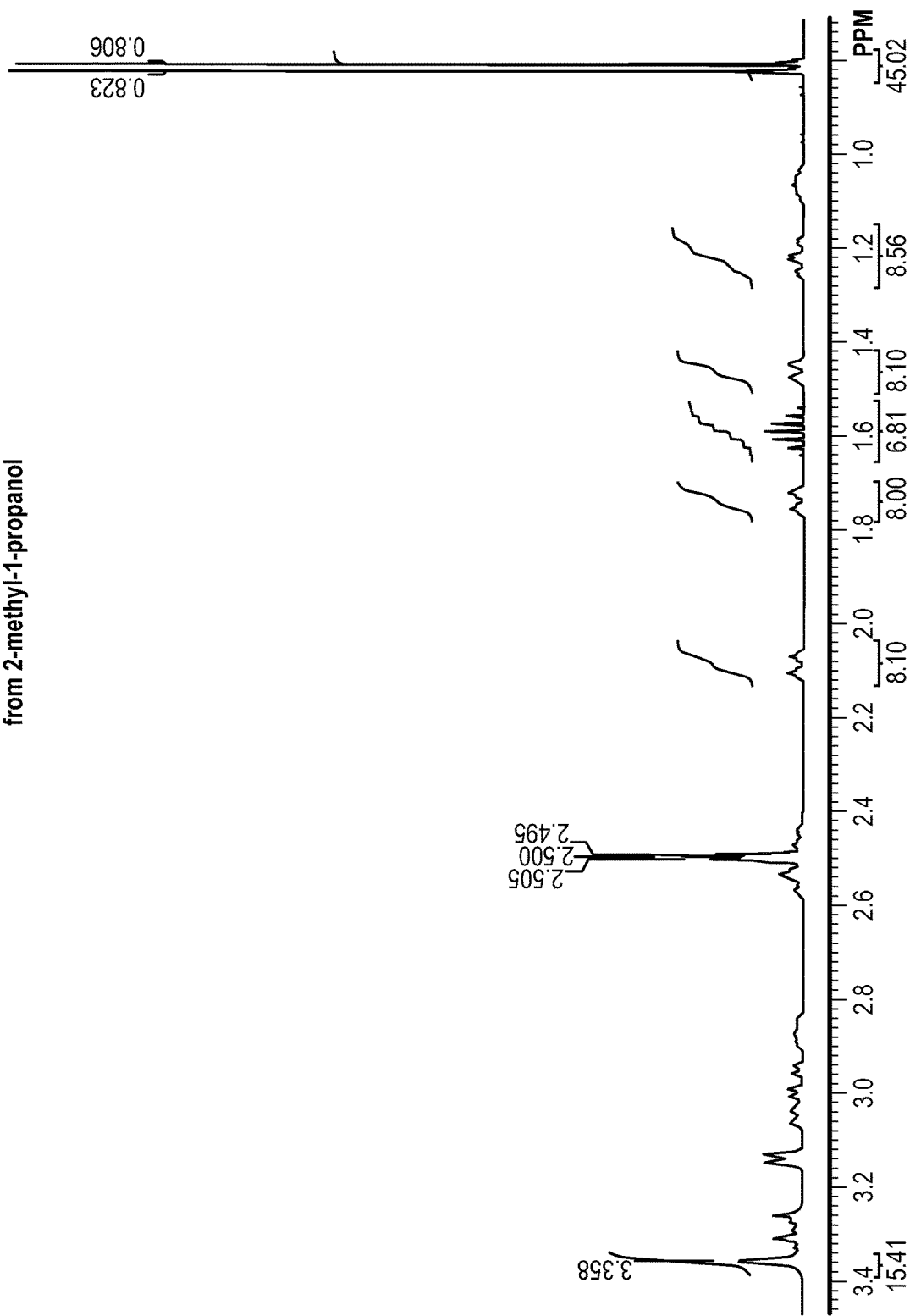

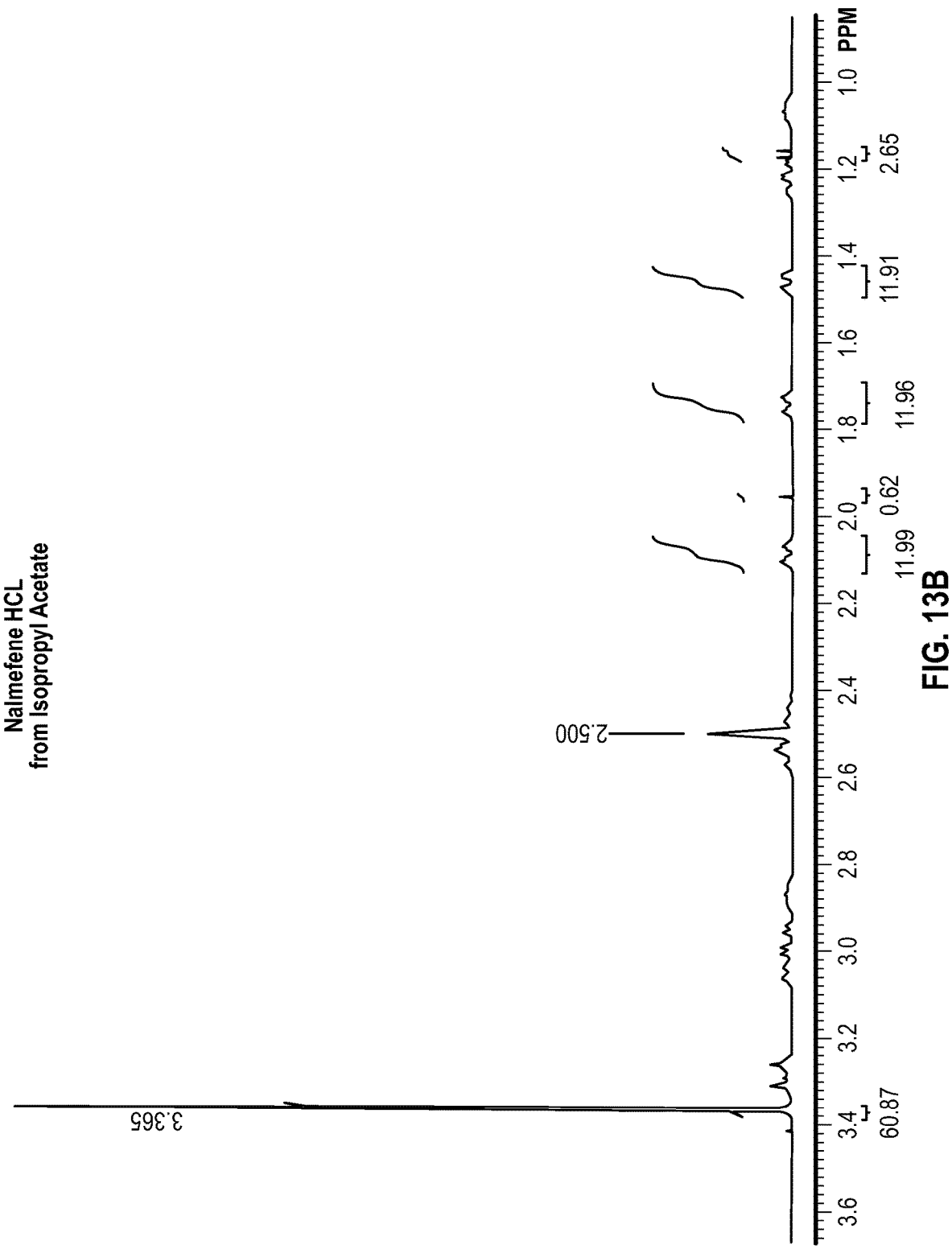

TECHNOLOGIES FOR REMOVING RESIDUAL SOLVENT FROM NALMEFENE HYDROCHLORIDE AND PRODUCING CRYSTALLINE NALMEFENE HYDROCHLORIDE MONOHYDRATE, MONOSOLVATE, OR CRYSTALLINE NALMEFENE HYDROCHLORIDE DIHYDRATE

FIELD

The present disclosure generally relates to technologies for removing residual solvent from Nalmefene Hydrochloride (HCl) and producing crystalline Nalmefene HCl monohydrate, monosolvate or Nalmefene HCl dihydrate. Crystalline Nalmefene HCl with a desirably low amount of residual solvent is also described.

BACKGROUND

Nalmefene is an opioid receptor antagonist that can inhibit the effects of endogenous and administered opioid agonists. Among other things, Nalmefene can rapidly reverse the effects of opioid agonists. The hydrochloride salt of Nalmefene (i.e., Nalmefene HCl, also known as 17-(cyclopropylmethyl)-4,5-alpha-epoxy-6-methylenemorphinan-3,14-diol hydrochloride) has long been used to treat alcohol dependency in patients. It has also been investigated for treatment of other conditions, particularly addictions such as gambling addiction.

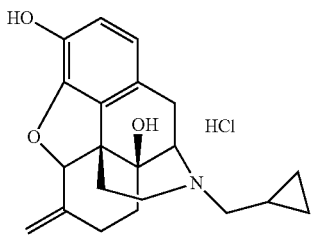

1, Nalmefene HCl

Naltrexone is another opioid antagonist and is structurally similar to Nalmefene. Nalmefene differs from Naltrexone in that instead of a ketone group at the 6 position of Naltrexone, Nalmefene includes a methylene ($CH_2$) group at that location. Consequently, Nalmefene can exhibit increased binding affinity to the μ-opioid receptor, relative to Naltrexone. Nalmefene can also bind to the other two opioid receptor types (i.e., the К and δ receptors) and is therefore known as a "universal antagonist."

Nalmefene can be synthesized from Naltrexone using the Wittig reaction—a known method for synthesizing olefins. In the Wittig reaction, a phosphorous ylide is prepared by treating a suitable salt (e.g., phosphonium salt) with a base. The ylide is then reacted with a substrate containing a carbonyl group to give an alkene. One method for producing Nalmefene by the Wittig reaction involves the reaction of Naltrexone with the ylide methylene triphenylphosphorane in dimethyl sulfoxide (DMSO). See Hahn and Fisherman, J. Med. Chem., vol. 18, pp. 259-262 (1975). In that process, however, a large amount of excess ylide is used, bringing with it the need to remove substantial amounts of biproducts to purify the obtained Nalmefene.

Various other methods for synthesizing Nalmefene via the Wittig reaction have been developed. For example, U.S. Pat. No. 4,535,157 discloses a method of synthesizing Nalmefene via the Wittig reaction by reacting Naltrexone with the ylide methylene triphenylphosphorane in tetrahydrofuran (THF) to yield Nalmefene base, which can be purified and converted to the hydrochloride salt. To further streamline the production of Nalmefene HCl, U.S. Pat. No. 8,598,352 describes a method for synthesizing Nalmefene HCl from Naltrexone using the Wittig reaction, wherein 2-methyltetrahydrofuran (MTHF) is used as a solvent. The '352 patent goes on to explain that the Nalmefene base obtained by its synthetic process of the '352 patent is isolated using a multistep process to obtain a residue containing the Nalmefene base. The residue is then dissolved in an organic solvent (e.g., dichloromethane) and the resulting solution is treated with hydrochloric acid (HCl) to precipitate Nalmefene HCl.

While the above noted and other methods of synthesizing Nalmefene HCl are useful, they are not without challenges. For example, many methods of producing Nalmefene HCl produce the monohydrate form of Nalmefene HCl, which is hygroscopic. While methods have been developed to produce the dihydrate form of Nalmefene HCl (which is not hygroscopic), those and the other above noted methods may utilize organic solvents that can become entrapped in the crystalline lattice of Nalmefene HCl. Removing or at least reducing the amount of residual solvent may be needed to ensure that the Nalmefene HCl may be safely consumed by a patient and/or comply with relevant regulatory requirements. Due to their entrapment in the crystalline lattice of Nalmefene HCl, however, it may be difficult to remove such solvents by conventional processes such as drying under vacuum.

Consequently, the inventors have identified that a need remains in the art for methods of producing crystalline Nalmefene HCl—particularly in its dihydrate form—wherein the Nalmefene HCl contains little or no residual solvent. The present disclosure aims to address that need.

BRIEF DESCRIPTION OF THE DRAWINGS

Features and advantages of embodiments of the claimed subject matter will become apparent as the following Detailed Description proceeds, and upon reference to the Drawings, wherein like numerals depict like parts, and in which:

FIG. 9A is a proton nuclear magnetic resonance (NMR) spectrum measured from a sample of crystalline Nalmefene HCl recrystallized from a mixture of n-butyl-acetate, Water, and Nalmefene HCl;

FIG. 10C is a Differential Scanning calorimetry (DC) plot measured from a sample of crystalline Nalmefene HCl recrystallized from a mixture of isobutyl acetate, Water, and Nalmefene HCl;

FIG. 11B is a magnified region of the NMR spectrum of FIG. 11A;

FIG. 11C is a Differential Scanning calorimetry (DC) plot measured from a sample of crystalline Nalmefene HCl recrystallized from a solution of n-propyl acetate, Water, and Nalmefene HCl;

FIG. 12B is a magnified region of the NMR spectrum of FIG. 12A;

FIG. 13B is a magnified region of the NMR spectrum of FIG. 13A;

DETAILED DESCRIPTION

One aspect of the present disclosure relates to methods of forming Nalmefene HCl. In embodiments, the methods described herein can produce crystalline Nalmefene HCl that contains little or no residual solvent. For example, using the methods herein one may prepare crystalline Nalmefene HCl that contains less than or equal to 15 weight % of residual solvent. In embodiments, the amount of residual solvent in the crystalline Nalmefene HCl is less than 10 weight %, such as less than or equal to 5 weight %, less than or equal to 2.5 weight %, or even less than or equal to 1.4 weight %.

Crystalline Nalmefene HCl has at least two polymorphs, including a monosolvate, monohydrate polymorph and a dihydrate polymorph. The dihydrate is preferred for many applications because—unlike the monosolvate, monohydrate form—the dihydrate is not hygroscopic. With that in mind, the methods described herein enable the formation of specific polymorphs of Nalmefene HCl. In embodiments, the crystalline Nalmefene HCl consists or consists essentially of the dihydrate polymorph, or consists or consists essentially of the monohydrate, monosolvate polymorph. Preferably, the crystalline Nalmefene HCl consists or consists essentially of the dihydrate polymorph.

Figure 1A:
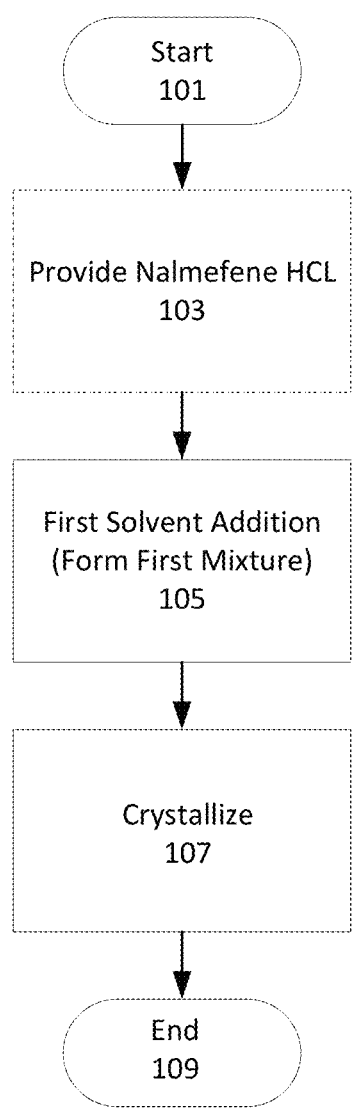
FIGS. 1A and 1B are flow diagrams of example operations of one example of a method of forming crystalline Nalmefene HCl consistent with the present disclosure.
Figure 1B:
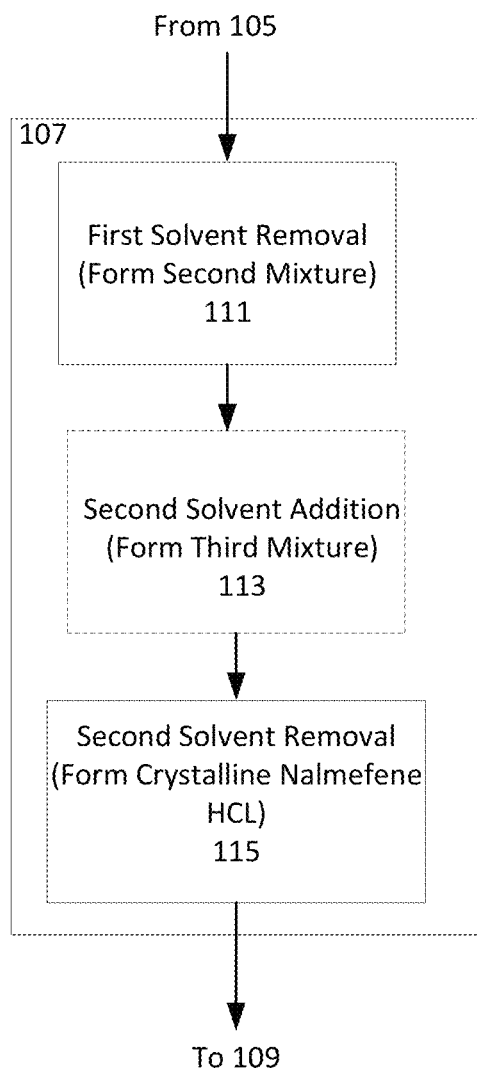

FIGS. 1A and 1B depict flow diagrams of example operations of one example of a method of forming Nalmefene HCl consistent with the present disclosure. As shown in FIG. 1A, method 100 begins at block 101. The method may then proceed to optional block 103, pursuant to which a stock solution of Nalmefene HCl may be provided. In embodiments, the stock solution is an aqueous solution of Nalmefene HCl in water.

The Nalmefene HCl in the stock solution may be produced by any suitable method, such as via the Wittig reaction. In embodiments the stock solution consists of a solution of Nalmefene HCl in water, wherein the concentration of Nalmefene HCl in the stock solution ranges from 100 mg/g to 150 mg/g. In embodiments, the stock solution is an aqueous solution containing 125 mg/g of Nalmefene HCl in water (i.e., 10 g Nalmefene HCl in 70 mL of water).

Following the operations of block 103 (or if block 103 is omitted), the method may proceed to block 105, pursuant to which a first solvent addition process is performed by adding a first solvent is added to the stock solution to form a first (mixture). In general, the first solvent is an organic solvent that, when added to the stock solution, forms a first mixture that is an azeotrope with water when distilled. That is, the addition of the first solvent to the stock solution produces a first mixture that has a constant boiling point and composition when it is subject to distillation. The ability of the first mixture to azeotrope can aid in the removal of water from the mixture, allowing crystallization of Nalmefene HCL from the mixture to occur.

The first solvent is preferably selected from solvents listed in ICH Q3C class 3 solvents on or before Dec. 1, 2019. Non-limiting examples of such solvents include Ethanol, 1-Butanol, 2-Butanone, 2-Propanol, Heptane, Ethyl acetate, 1-Propanol, n-Butyl acetate, Isobutyl acetate, n-Propyl acetate, 2-Methyl-1-propanol, and Isopropyl alcohol, combinations thereof, and the like. Table 1 lists various properties of such solvents.

TABLE 1

Properties of Example First Solvents

| Solvent | BP[1] | H$_2$O Miscibility[2] | Azeotrope[3] | MV[4] | MW[5] |
|---|---|---|---|---|---|
| Ethanol | 78 | 100 | 96 | 59.0 | 46.07 |
| 1-Butanol | 118 | 7.45 | 57 | 92.0 | 74.12 |
| 2-Butanone | 80 | 26 | 89 | 91.6 | 72.11 |
| 2-Propanol | 83 | 100 | 88 | 75.9 | 60.10 |
| Heptane | 98 | 0.01 | 87 | 144.0 | 100.20 |
| Ethyl acetate | 77 | 7.7 | 92 | 98.0 | 88.10 |
| 1-Propanol | 97 | 100 | 72 | 75.5 | 60.10 |
| n-Butyl acetate | 125 | 0.5 | 73 | 131.0 | 116.16 |
| Isobutyl acetate | 117 | 0.6 | 83 | 131.4 | 116.16 |
| n-Propyl acetate | 102 | 2.3 | 86 | 114.5 | 102.13 |
| 2-Methyl-1-propanol | 108 | 8.7 | 73 | 92.4 | 74.122 |
| Isopropyl acetate | 87 | 2.9 | 89 | 114.9 | 102.13 |

[1]BP - Boiling Point (° C.)
[2]Miscibility with H$_2$O (%)
[3]Azeotrope with H$_2$O (%)
[4]MV - Molar Volume (cm$^3$)
[5]MW - Molecular Weight (g/mol)

The inventors have surprisingly found that the molar volume of the first solvent can impact the polymorph of Nalmefene HCl that is formed, as well as the amount of residual solvent contained therein. In embodiments the first solvent is an organic solvent with a molar volume of greater than or equal to 98 cm$^3$, such as greater than or equal to 110 cm$^3$, greater than or equal to 120 cm$^3$, greater than or equal to 120 cm$^3$, or even greater than or equal to 140 cm$^3$. Non-limiting example of such solvents include Heptane, Ethyl acetate, n-Butyl acetate, Isobutyl acetate, n-Propyl acetate, Isopropyl alcohol, combinations thereof, and the like. In such embodiments and as will be described further below, the crystalline Nalmefene HCl formed by the methods described herein may include, consist essentially of, or consist of the dihydrate polymorph, and may contain less than or equal to 5 weight %, such as less than or equal to 2.5 weight %, or even less than or equal to 1.4 weight % of residual solvent.

In other embodiments, the first solvent is an organic solvent with a molar volume in a range of greater than 0 to less than 95 cm$^3$ (i.e., <95 cm$^3$), such as about 55 to about 95 cm$^3$. Non-limiting examples of such solvents include Ethanol, 1-Butanol, 2-Butanone, 2-Propanol, 1-Propanol, 2-Methyl-1-propanol, combinations thereof, and the like. In such embodiments, the crystalline Nalmefene HCl formed by the methods described herein may include the monohydrate, monosolvate polymorph, and may contain greater than 5 weight %, such as from 8 to 15 weight % or even from 9.8 to 14.9 weight % of residual solvent. In still further embodiments, the first solvent is selected from Ethanol, 2-Propanol, 1-Propanol, 2-Methyl-1-propanol, or a combination thereof, and the Nalmefene HCl formed consists or consists essentially of monohydrate, monosolvate polymorph, and contains greater than 5 weight % (e.g. from 8 to 15 weight % or even from 9.8 to 14.9 weight %) of residual solvent.

Any suitable amount of first solvent may be added to the stock solution pursuant to block 105. In embodiments, the amount of first solvent added in the first solvent addition process is selected such that the resulting first mixture has a ratio of first solvent:stock solution ranging from 2:1 to 10:1, such as from 2:1 to 5:1, or even 3:1 to 5:1. Preferably, the ratio of first solvent:stock solution in the first mixture ranges from 3:1 to 5:1. In embodiments, the first solvent addition process results in a first mixture in the form of a multiphasic (e.g. biphasic) mixture.

Following the operations of block 105 the method may process to block 107, pursuant to which crystalline Nalmefene HCl may be formed. In general, the formation of crystalline Nalmefene HCl involves removing the first solvent from the first mixture of Nalmefene HCl, water, and first solvent. The removal of first solvent from the first mixture may be performed in any suitable manner. In embodiments, first solvent is removed from the first mixture using one or a series of solvent removal operations. For example, the first solvent may be removed from the first mixture using one or more vacuum distillation operations, wherein each of such operations includes heating the first mixture above room temperature (e.g., to a temperature greater than or equal to 40° C.) and drying the heated first mixture under vacuum (e.g., with a pressure in the range of 1 to 50 mbar, preferably 5 to 20 mbar) to remove the first solvent.

In embodiments, the substantially all the first solvent may be removed in a single solvent removal operation. In such operations, the method may proceed from block 107 to block 109 and end. In other embodiments the operations of block 107 may include multiple solvent removal operations. For example and as shown in FIG. 1B, the operations of block 107 may begin with block 111, pursuant to which the first mixture may be subject to a first solvent removal operation. In embodiments, the first solvent removal operation is a first vacuum distillation operation in which the first mixture produced pursuant to block 105 is heated above room temperature (e.g., to a temperature greater than or equal to 40° C.) and dried under vacuum to partially remove the first solvent and form a second mixture that is partially dried, relatively to the first mixture. That is, the second mixture may include an amount of first solvent that is less than the amount of first solvent in the first mixture. For example, the amount of first solvent in the second mixture may be 10-90% less than the amount of first solvent in the first mixture. Following the operations of block 111 the method may proceed to optional block 113, pursuant to which additional first solvent may be added to the second mixture, resulting in the formation of a third mixture. The amount of additional first solvent added to the second mixture may vary, and any suitable amount of additional first solvent may be added. In embodiments, the amount of additional first solvent added to the second mixture ranges from 10% to 125% by weight of the amount of first solvent added (e.g., from 50 to 120%, or even from 60 to 115%) to the stock solution pursuant to block 105.

Following the operations of block 113 the method may proceed to block 115, pursuant to which second solvent removal operations may be performed. The second solvent removal operations may be the same or different from the first solvent removal operations of block 111. In embodiments, the second solvent removal operations include heating the second solvate to above room temperature (e.g., greater than or equal to 40° C.) and drying the heated second solvate under vacuum. The vacuum used in the second solvent removal operation may have the same or different vacuum pressure as the vacuum used in the first solvent removal operation. In embodiments, the pressure of the vacuum used in the second solvent removal operation is the same or substantially the same (i.e., within +/−5%) of the vacuum pressure used in the first solvent removal operation (e.g., 1-50 mbar, preferably 5-20 mbar).

The operations of block 115 generally removes all or substantially all the first solvent from the second solvate, and results in the formation of crystalline Nalmefene HCl. To the extent additional solvent (e.g., water, first solvent, or both) remains, however, the method may proceed to optional block 117, pursuant to which the crystalline Nalmefene HCl may be subject to one or more additional drying processes. For example, the crystalline Nalmefene HCl may be dried under vacuum to reduce the amount of water and/or further reduce the amount of first solvent remaining following the operations of block 115. Following the operations of optional block 115 (or if such operations are omitted), the method may proceed to block 109. At that point, crystalline Nalmefene HCl is produced.

As discussed above, the inventors have surprisingly discovered that by appropriately selecting the solvent used as the first solvent, it is possible to produce crystalline Nalmefene HCl that contains a desirably low amount of residual solvent. For example, the method 100 can enable the production of crystalline Nalmefene HCl that contains less than or equal to 15 weight % of residual first solvent, such as less than or equal to 10 weight %, less than or equal to 5 weight %, less than or equal to 2.5 weight %, or even less than or equal to 1.4 weight % of residual solvent. Preferably, the methods produce Nalmefene HCl that contains less than or equal to 5 weight %, less than or equal to 2.5 weight %, or even less than or equal to 1.4 weight % of residual first solvent.

As also discussed above, the inventors have surprisingly discovered that the molar volume of the first solvent can also be highly determinative of the polymorph of Nalmefene HCl that is produced by process 100. Specifically, the inventors have determined that when a first solvent having a molar volume greater than or equal to 98 cm$^3$ is used, process 100 generally produces crystalline Nalmefene HCl that includes, consists essentially of, or consists of the dihydrate polymorph. In contrast, when the first solvent has a molar volume of 95 cm$^3$ or less (e.g. from 55 cm$^3$ to 95 cm$^3$) and process 100 generally produces crystalline Nalmefene HCl that includes, consists essentially of, or consists of the monohydrate monosolvate polymorph. Without limitation, a solvent with a molar volume greater than or equal to 98 cm$^3$ is used as the first solvent, and process 100 produces crystalline Nalmefene HCl that consists essentially of or consists of the dihydrate polymorph.

In embodiments, the molar volume of the first solvent is greater than or equal to 98 cm$^3$, process 100 produces crystalline Nalmefene HCl that includes, consists of, or consists essentially of the dihydrate polymorph, and the crystalline Nalmefene HCl contains less than or equal to 5 weight %, less than or equal to 2.5 weight %, or even less than or equal to 1.4 weight % of residual first solvent. In other embodiments, the molar volume of the first solvent is less than or equal to 95 cm$^3$ (e.g., from 55 to 95 cm$^3$), process 100 produces crystalline Nalmefene HCl that includes, consists of, or consists essentially of the monohydrate, monosolvate polymorph, and the crystalline Nalmefene HCl contains less than or equal to 15 weight % of residual first solvent, such as from 8 to 15 weight % or even about 9.8 to 14.9 weight % of residual first solvent.

Another aspect of the present disclosure relates to crystalline Nalmefene HCl that includes less than or equal to 15 weight % of a residual amount of a first solvent.

In embodiments, the first solvent is an organic solvent with a molecular volume molar volume of greater than or equal to about 98 cm$^3$, such as but not limited to those specified in table 1 above. In such embodiments the residual amount of first solvent is in the range of less than or equal to 5 weight %, such as less than or equal to 2.5 weight %, or even less than or equal to 1.4 weight %. Alternatively or additionally, the Nalmefene HCl in such embodiments includes, consists essentially of, or consists of crystalline Nalmefene HCl dihydrate. Preferably, the Nalmefene HCl in such embodiments consists essentially of or consists of crystalline Nalmefene HCl dihydrate.

In other embodiments, the first solvent is an organic solvent with a molecular volume of less than or equal to 95 cm$^3$, such as from about 55 to 95 cm$^3$. In such embodiments the amount of residual amount in the Nalmefene HCl ranges from 8 to 15 weight %, such as from 9.8 to 14.9 weight %. Alternatively or additionally, the Nalmefene HCl in such embodiments includes, consists essentially of, or consists of crystalline Nalmefene HCl monohydrate monosolvate. Preferably, the Nalmefene HCl in such embodiments consists essentially of or consists of crystalline Nalmefene HCl monohydrate monosolvate.

EXAMPLES

To evaluate the efficacy of the methods described herein, a stock solution of Nalmefene HCL was prepared by dissolving 10 g of Nalmefene HCl in 70 ml of water to produce a solution with a concentration of 125 mg/g. Mixtures were prepared by adding a first solvent to the stock solution in a 40 ml vial. The amount of stock solution, the type of first solvent, and the amount of first solvent are reported in table 2 below.

TABLE 2

Preparation of Nalmefene HCL solvates

| # | Amount of Stock Solution (g) | Solvent | Amount of Solvent (g) | Observations |
|---|---|---|---|---|
| 1 | 4.0 | Ethanol | 15.1 | One layer, pale yellow |
| 2 | 4.1 | 1-Butanol | 15.2 | One layer, pale yellow |
| 3 | 4.0 | 2-Butanone | 14.8 | Two layers, top layer light in color |
| 4 | 4.0 | n-Butyl acetate | 15.3 | Two layers, top layer light in color |
| 5 | 4.0 | 2-Propanol | 14.9 | One layer, pale yellow |
| 6 | 4.2 | Heptane | 12.6 | Two layers, top layer light in color |
| 7 | 4.0 | Ethyl Acetate | 16.0 | Two layers, top layer light in color |
| 8 | 4.0 | 1-Propanol | 14.4 | One layer, pale yellow |
| 9 | 4.0 | Isopropyl acetate | 15.3 | Two layers, top layer light in color |
| 10 | 4.2 | Isobutyl acetate | 16.8 | Two layers, top layer light in color |
| 11 | 4.1 | N-propyl acetate | 16.2 | Two layers, top layer light in color |
| 12 | 4.2 | 2-Methyl-1-propanol | 14.1 | One layer, pale yellow (emulsion) |

Each sample mixture was placed in a Genevac EZ-2 Mk3 evaporator, and subject to a first evaporation cycle, during which the samples were heated to 40° C. and dried using program 09-HPLC, which included three stages. During stage 1 of the program, the atmosphere within the evaporator was initially pulled down to 250 mbar (187 Torr) and then ramped down to 40 mbar (30 Torr) over a period of 30 minutes. The sample being processed was held in that atmosphere (at 40 mbar (30 Torr)) for an additional 40 minutes. During stage 2 (following stage 1), the atmosphere within the evaporator is pulled down to 8 mbar (6 Torr), and the sample being processed was subject to that vacuum for up to 510 minutes or until heatflow software of the evaporator determined that the bulk of the solvent in the sample being processed was removed. Thereafter the sample was subject to stage 3—during which the atmosphere within the evaporator was pulled to full or substantially full vacuum and the sample being processed was dried under than condition for 40 minutes. Following the first evaporation cycle, the observations shown in Table 3 below were made:

TABLE 3

Observations following the first evaporation cycle

| # | Solvent | Observations |
|---|---|---|
| 1 | Ethanol | No crystals; ~4 mm of solvent remaining |
| 2 | 1-Butanol | Crystals formed; ~24 mm of solvent remaining |
| 3 | 2-Butanone | Crystals formed; ~3 mm of solvent remaining |
| 4 | n-Butyl acetate | No crystals; ~6 mm of solvent remaining |
| 5 | 2-Propanol | Crystals formed; ~5 mm of solvent remaining |
| 6 | Heptane | Crystals formed; ~5 mm of solvent remaining |
| 7 | Ethyl Acetate | No crystals; ~mm of solvent remaining |
| 8 | 1-Propanol | Crystals formed; ~5 mm of solvent remaining |
| 9 | Isopropyl acetate | Large crystals; ~3 mm of solvent remaining |
| 10 | Isobutyl acetate | Large crystals; ~3 mm of solvent remaining |
| 11 | N-propyl acetate | Large crystals; ~3 mm of solvent remaining |
| 12 | 2-Methyl-1-propanol | Small crystals; ~12 mm of solvent remaining |

Following the first evaporation cycle, additional solvent was added to each sample and the samples were subject to a second evaporation cycle that was the same as the first evaporation cycle. The amount of solvent added and the observed results are provided in table 4 below.

TABLE 4

Observations following the second evaporation cycle

| # | Solvent | Solvent added (g) | Observations |
|---|---|---|---|
| 1 | Ethanol | 16.6 | Crystalline solid; no solvent observed |
| 2 | 1-Butanol | 9.3 | Crystalline solid; ~16 mm of solvent |
| 3 | 2-Butanone | 16.9 | Crystalline solid; no solvent observed |
| 4 | n-Butyl acetate | 17.3 | Crystalline solid; ~2 mm of solvent |
| 5 | 2-Propanol | 17.6 | Crystalline solid; no solvent observed |
| 6 | Heptane | 12.7 | Crystalline solid; no solvent observed |
| 7 | Ethyl Acetate | 17.2 | Crystalline solid; no solvent observed |
| 8 | 1-Propanol | 15.1 | Crystalline solid; no solvent observed |
| 9 | Isopropyl acetate | 17.6 | Microcrystalline solid; no solvent observed |
| 10 | Isobutyl acetate | 16.0 | Microcrystalline solid; no solvent observed |
| 11 | N-propyl acetate | 17.7 | Microcrystalline solid; no solvent observed |
| 12 | 2-Methyl-1-propanol | 12.9 | Crystalline solid; ~9 mm of solvent |

Water remained in sample 4 following the second evaporation cycle, and so that sample was subject to a third evaporation cycle. To isolate the solids, additional solvent was added to most of the samples, the solids were broken up with a spatula, vortexed and/or briefly sonicated, filtered, and the solids were washed with additional solvent. Table 5 provides further details concerning the isolation operation, including the amount of solvent added and used in the solvent wash, and the recovery amount in grams and percent.

TABLE 5

Isolation of Crystalline Samples

| # | Solvent | Solvent added (g) | Solvent Wash (g) | Recovery (g) | Recovery (%) |
|---|---|---|---|---|---|
| 1 | Ethanol | 2.6 | 2.5 | .20 | 40 |
| 2 | 1-Butanol | 0.0[a] | 2.0 | 0.73 | 140 |
| 3 | 2-Butanone | 3.1 | NR[b] | 0.53 | 105 |
| 4 | n-Butyl acetate | 5.2[c] | NA[c] | NA[c] | NA[c] |
| 4a[d] | n-Butyl acetate | 6.4 | 4.4 | 0.51 | 101 |
| 5 | 2-Propanol | 4.7 | 2.0 | 0.56 | 112 |
| 6 | Heptane | 4.4 | 2.2 | 0.50 | 96 |
| 7 | Ethyl Acetate | 4.8 | 2.5 | 0.55 | 110 |
| 8 | 1-Propanol | 4.0 | 1.8 | 0.55 | 109 |
| 9 | Isopropyl acetate | 4.9 | 2.8 | 0.54 | 108 |
| 10 | Isobutyl acetate | 5.7 | 2.5 | 0.53 | 101 |
| 11 | N-propyl acetate | 5.4 | 2.6 | 0.53 | 103 |
| 12 | 2-Methyl-1-propanol | 3.0 | 2.6 | 0.62 | 118 |

[a]No additional solvent was added
[b]NR = not reported
[c]Water remaining in the sample
[d]After the third vacuum drying cycle.

All the samples were placed in the Genevac evaporator for a final evaporation cycle during which the samples were heated to 40° C. and further dried using program 01-very low BP, which includes two stages. During the first stage of that program, the atmosphere within the atmosphere was pulled down to 600 mbar (450 Ton) and then ramped down to 100 mbar (75 Ton) over a period of 40 minutes. The sample being processed was held in that atmosphere (at 100 mbar (75 Ton)) for up to an additional 260 minutes or until heatflow software of the evaporator determined that the bulk of the solvent was removed from the sample, whichever was sooner. Following the final evaporation cycle, the samples were analyzed by proton nuclear magnetic resonance (NMR), differential scanning calorimetry (DSC), and x-ray powder diffraction (XRPD). The details of each analysis are discussed below.

Proton NMR:

Each of the samples were analyzed by proton NMR to determine the amount of residual water and solvent remaining in the solids. To perform the analysis, approximately 20 mg of each sample was dissolved in 1ml of deuterated dimethylsulfoxide (DMSO). The DMSO was contained in a sure seal bottle to prevent exposure to moisture. The approximate concentration of the analyzed samples was 20 mg/ml. Each sample was analyzed using a Varian 400 MHz proton NMR instrument. The water peak, a known Nalmefene peak, and a known solvent peak were integrated and the data was processed to calculate the mole and weight % of water and solvent remaining in the sample. The NMR spectra obtained are shown in FIGS. 2A, 2B, 3A, 3B . . . 13A, and 13B, and the results are provided in Table 6 below.

TABLE 6

Residual water and solvent determined by proton NMR

| # | Solvent | H$_2$O (mol %) | Solvent (mol %) | H$_2$O (wt. %) | Solvent (wt. %) |
|---|---|---|---|---|---|
| 1 | Ethanol | 33.69 | 31.94 | 4.05 | 9.81 |
| 2 | 1-Butanol | 14.36 | 50.89 | 1.51 | 22.07 |
| 3 | 2-Butanone | 53.08 | 12.05 | 6.40 | 5.82 |
| 4a | n-Butyl acetate | 32.61 | 30.50 | 3.61 | 11.25 |
| 5 | 2-Propanol | 65.49 | 0.17 | 8.36 | 0.12 |

TABLE 6-continued

Residual water and solvent determined by proton NMR

| # | Solvent | H$_2$O (mol %) | Solvent (mol %) | H$_2$O (wt. %) | Solvent (wt. %) |
|---|---|---|---|---|---|
| 6 | Heptane | 61.75 | 3.87 | 7.74 | 2.37 |
| 7 | Ethyl Acetate | 33.71 | 29.62 | 3.76 | 11.01 |
| 8 | 1-Propanol | 64.54 | 1.69 | 8.27 | 1.40 |
| 9 | Isopropyl acetate | 69.09 | 0.51 | 9.78 | 0.46 |
| 10 | Isobutyl acetate | 67.67 | 1.77 | 9.46 | 1.40 |
| 11 | N-propyl acetate | 33.10 | 32.23 | 3.72 | 14.92 |
| 12 | 2-Methyl-1-propanol | 71.46 | 0.49 | 10.83 | 0.42 |

Except for 1-butanol and 2-butanone, the samples crystallized as either the monohydrate, monosolvate (MHMS) or as the dihydrate (DH). A correlation was observed between the salt form, the residual water content, and the molar volume of the solvent as shown in Table 7. Specifically, the solvents with a molar volume of greater than or equal to 98 cm$^3$ or more crystallized as the dihydrate polymorph, and contained 5 weight % or less of residual solvent. In contrast, the solvents with a molar volume less than or equal to 95 cm$^3$ (other than 1-butanol and 2 butanone) crystallized as the monohydrate, monosolvate polymorph and contained 5.82 weight % or more of residual solvent.

TABLE 7

Correlation between molar volume, salt form, and residual solvent

| # | Solvent | Molar Volume (cm$^3$) | Residual H$_2$O (mol) | Residual Solvent (Mol) | Residual Solvent (Wt. %) | Polymorph |
|---|---|---|---|---|---|---|
| 1 | Ethanol | 59 | 1.01 | 0.96 | 9.81 | MHMS |
| 2 | 1-Butanol | 92 | 0.43 | 1.53 | 22.07 | DH and MHMS |
| 3 | 2-Butanone | 91.6 | 1.59 | 0.36 | 5.82 | DH and MHMS |
| 4a | n-Butyl acetate | 131 | 1.94 | 0.05 | 1.40 | DH |
| 5 | 2-Propanol | 75.9 | 0.98 | 0.92 | 11.25 | MH |
| 6 | Heptane | 144 | 1.96 | 0.01 | 0.12 | DH |
| 7 | Ethyl Acetate | 98 | 1.85 | 0.12 | 2.37 | DH |
| 8 | 1-Propanol | 75.5 | 1.01 | 0.89 | 11.01 | MH |
| 9 | Isopropyl acetate | 114.9 | 2.14 | 0.01 | 0.42 | DH |
| 10 | Isobutyl acetate | 131.4 | 2.07 | 0.02 | 0.46 | DH |
| 11 | N-propyl acetate | 114.5 | 2.03 | 0.5 | 1.40 | DH |
| 12 | 2-Methyl-1-propanol | 92.4 | 0.99 | 0.97 | 14.92 | MH |

Figure 2A:
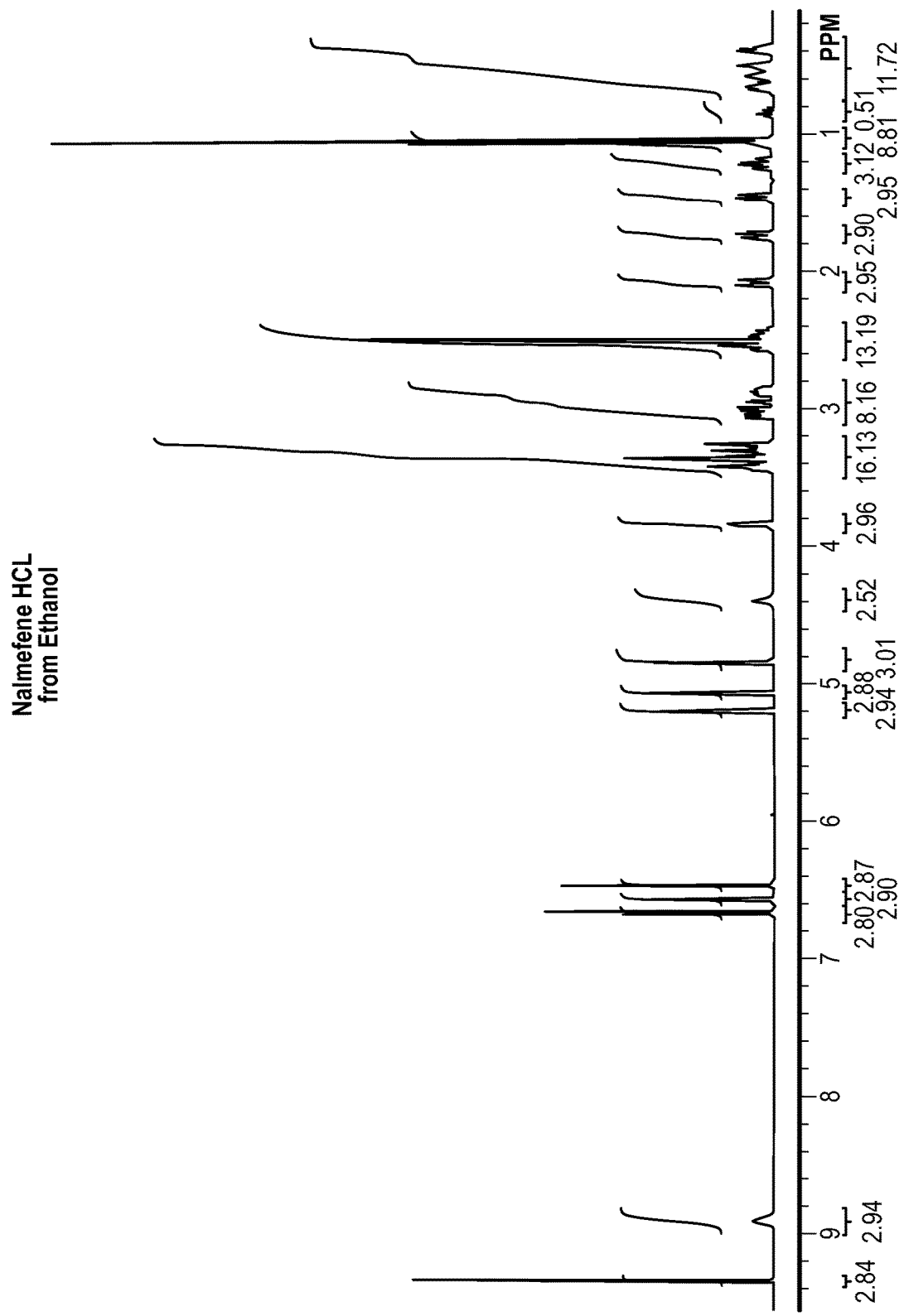
FIG. 2A is a proton nuclear magnetic resonance (NMR) spectrum measured from a sample of crystalline Nalmefene HCl recrystallized from a mixture of Ethanol, Water, and Nalmefene HCl.
Figure 2B:
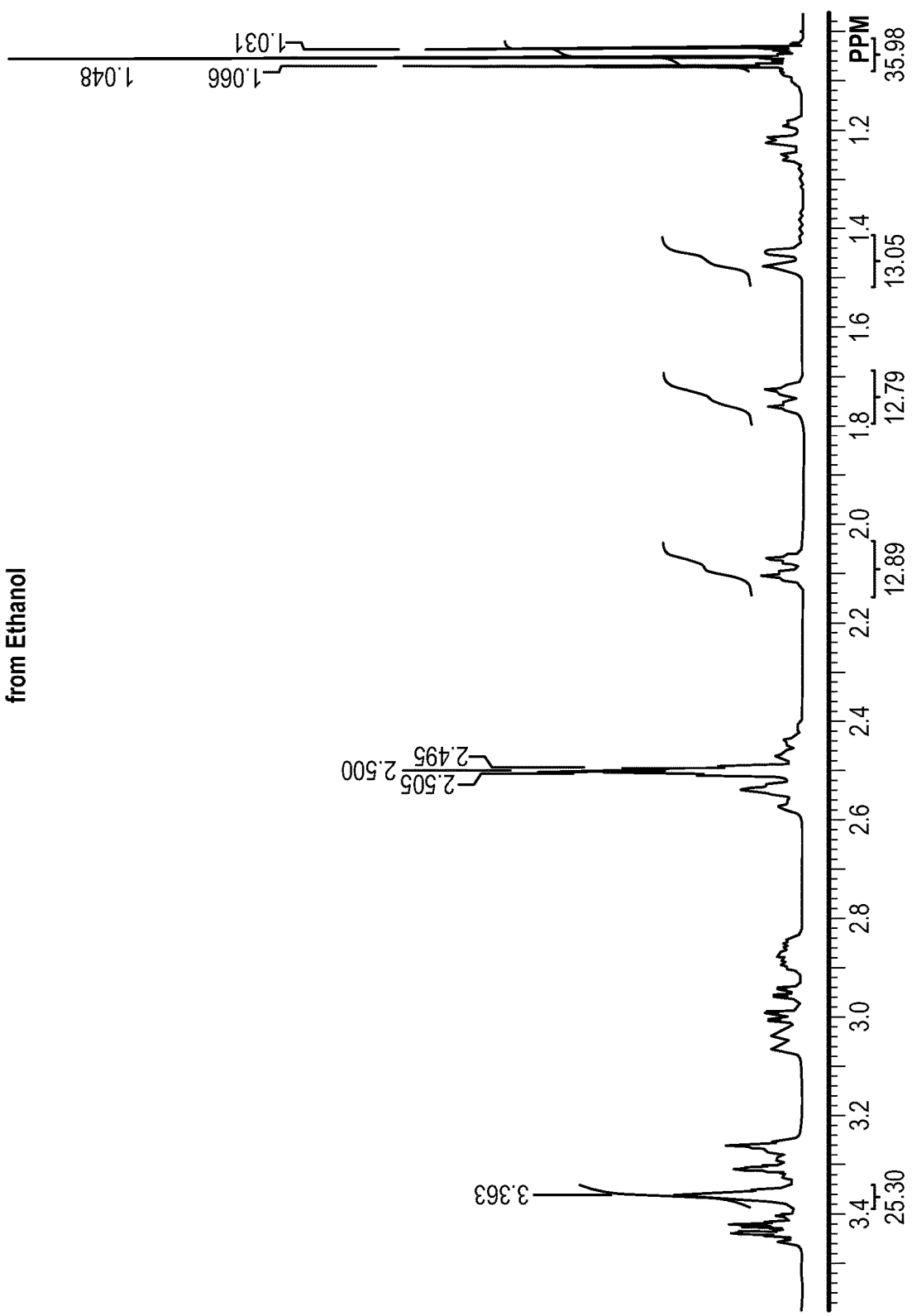
FIG. 2B is a magnified region of the NMR spectrum of FIG. 2A.
Figure 2C:
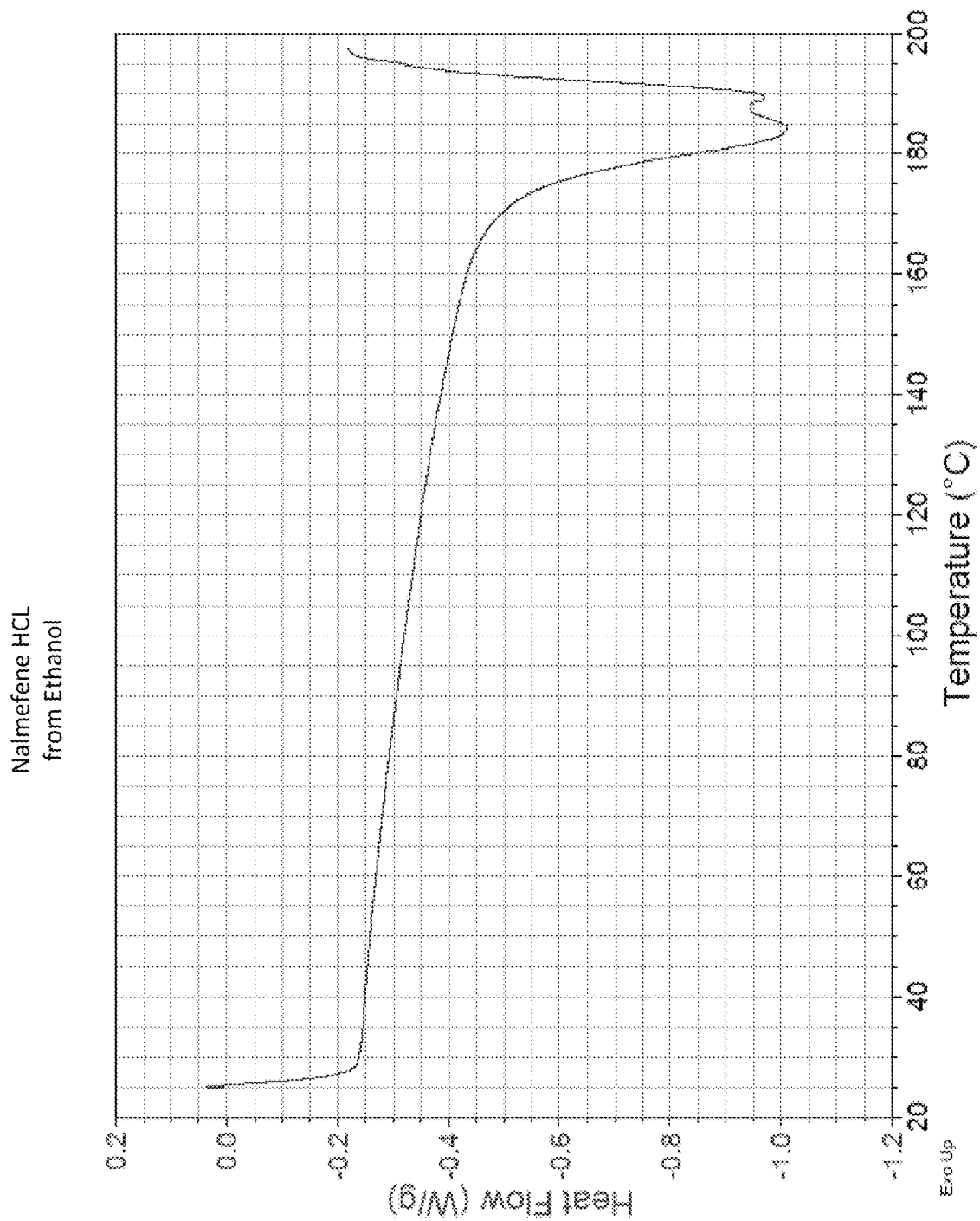
FIG. 2C is a Differential Scanning calorimetry (DC) plot measured from a sample of crystalline Nalmefene HCl recrystallized from a mixture of Ethanol, Water, and Nalmefene HCl.
Figure 3A:
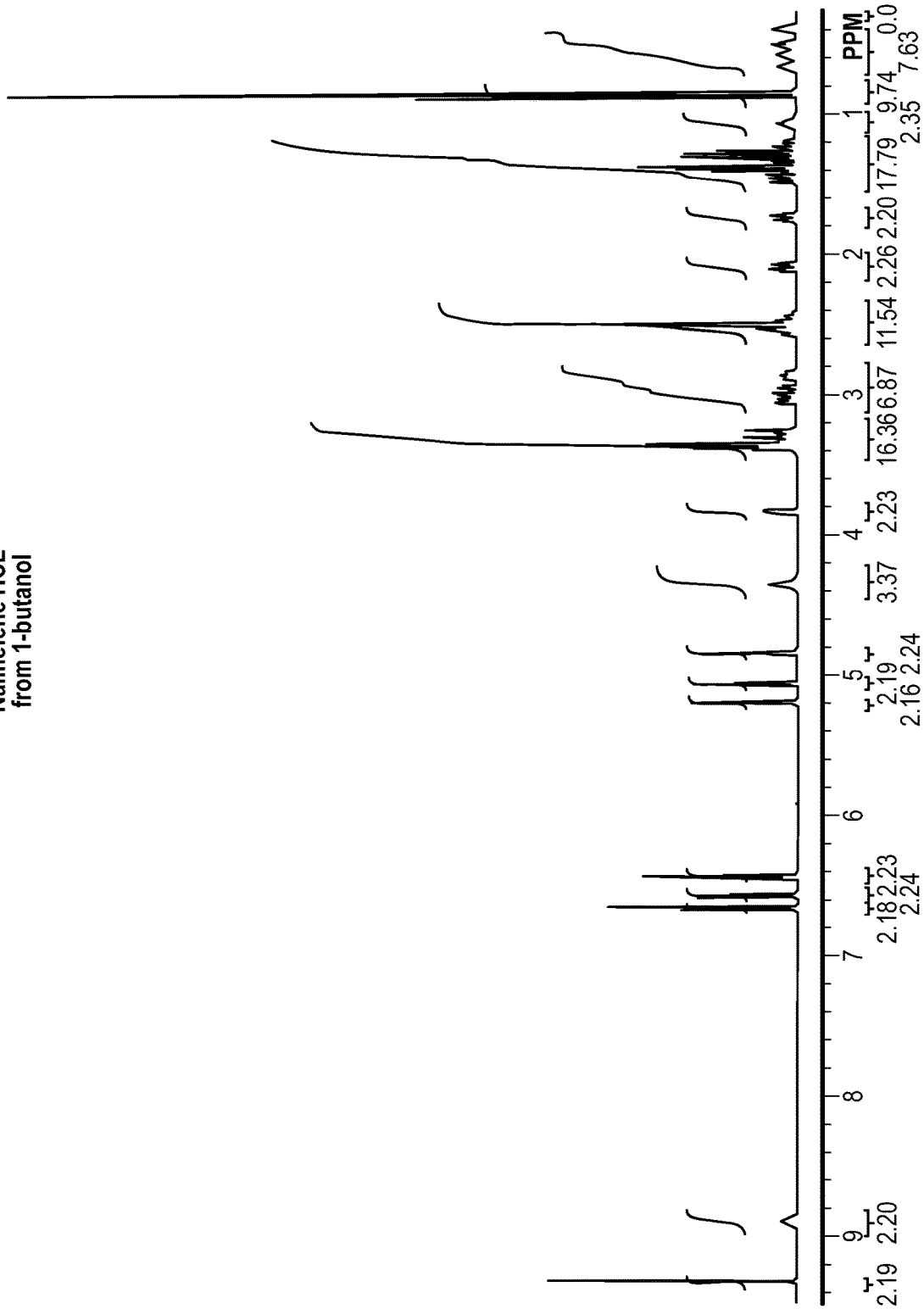
FIG. 3A is a proton nuclear magnetic resonance (NMR) spectrum measured from a sample of crystalline Nalmefene HCl recrystallized from a mixture of 1-butanol, Water, and Nalmefene HCl.
Figure 3B:
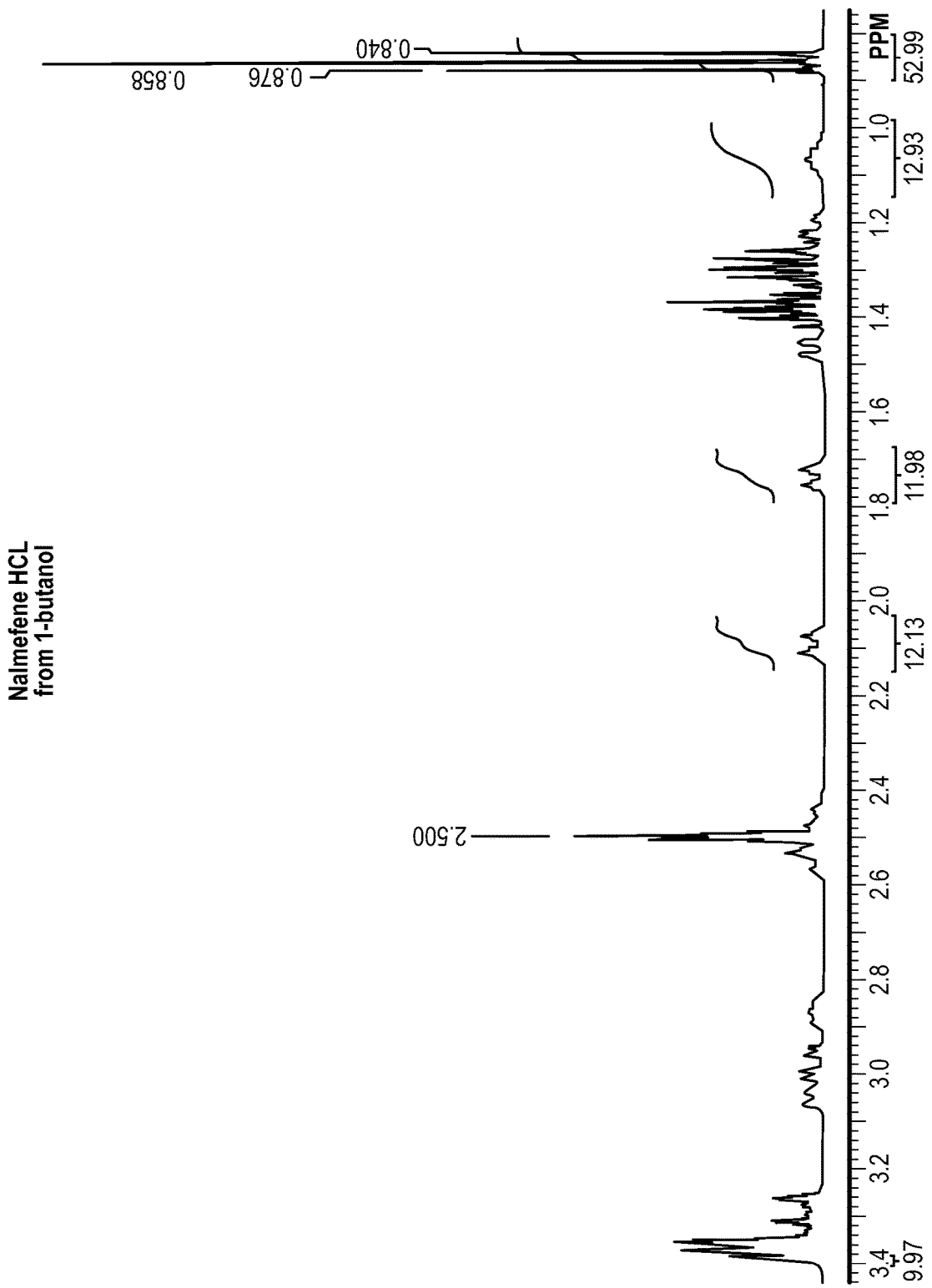
FIG. 3B is a magnified region of the NMR spectrum of FIG. 3A.
Figure 3C:
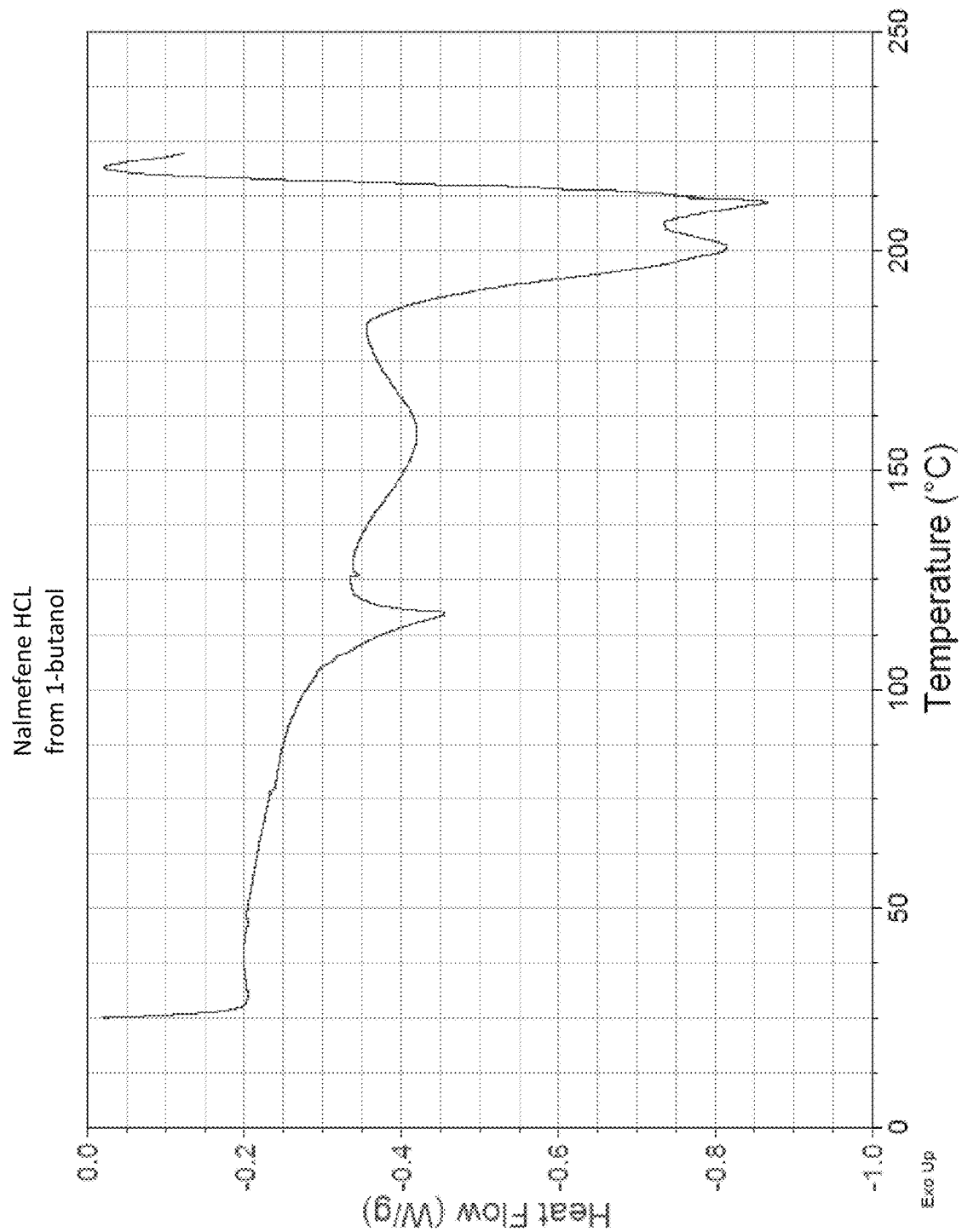
FIG. 3C is a Differential Scanning calorimetry (DC) plot measured from a sample of crystalline Nalmefene HCl recrystallized from a mixture of 1-butanol, Water, and Nalmefene HCl.
Figure 3D:
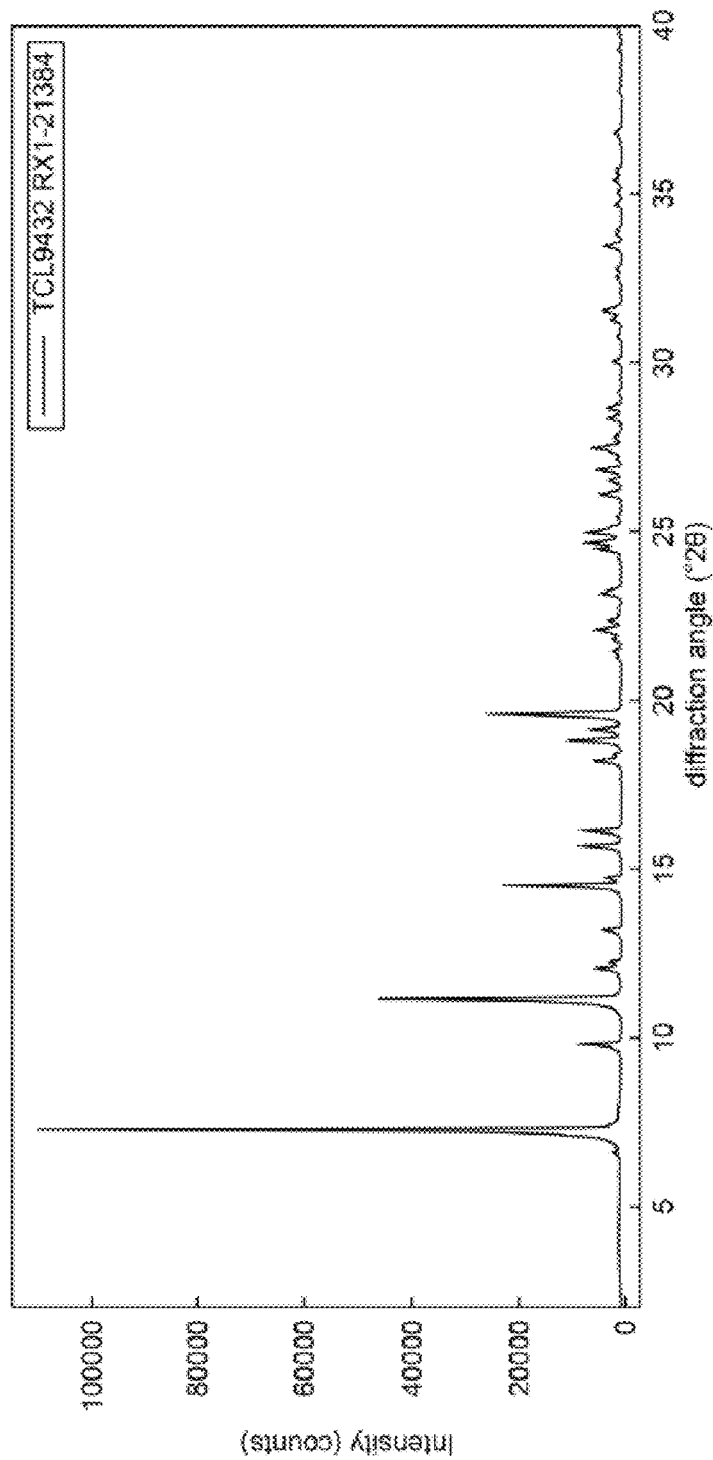
FIG. 3D is an x-ray diffraction spectrum measured from a sample of crystalline Nalmefene HCl recrystallized from a mixture of 1-butanol, Water, and Nalmefene HCl.
Figure 4A:
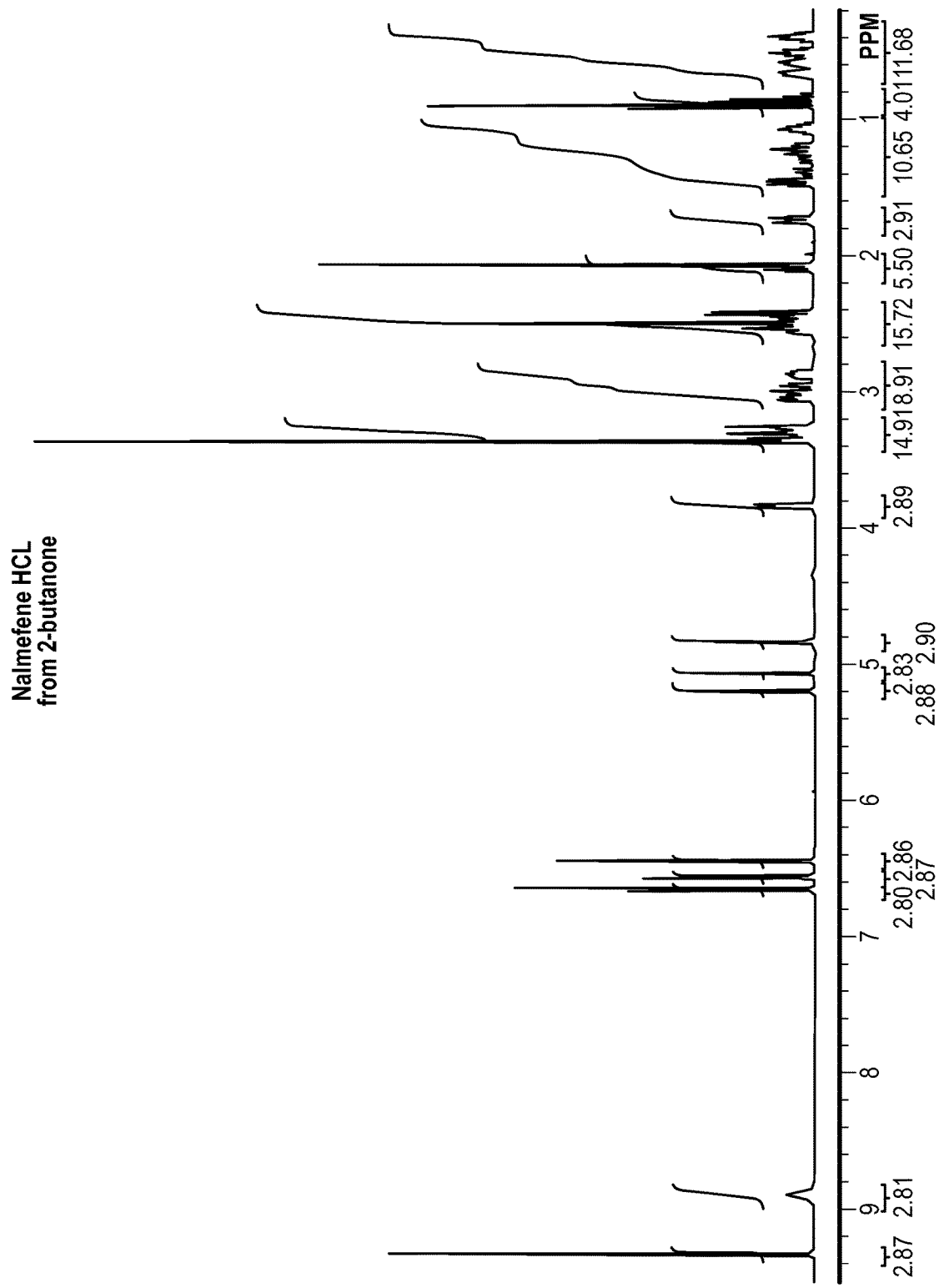
FIG. 4A is a proton nuclear magnetic resonance (NMR) spectrum measured from a sample of crystalline Nalmefene HCl recrystallized from a mixture of 2-butanone, Water, and Nalmefene HCl.
Figure 4B:
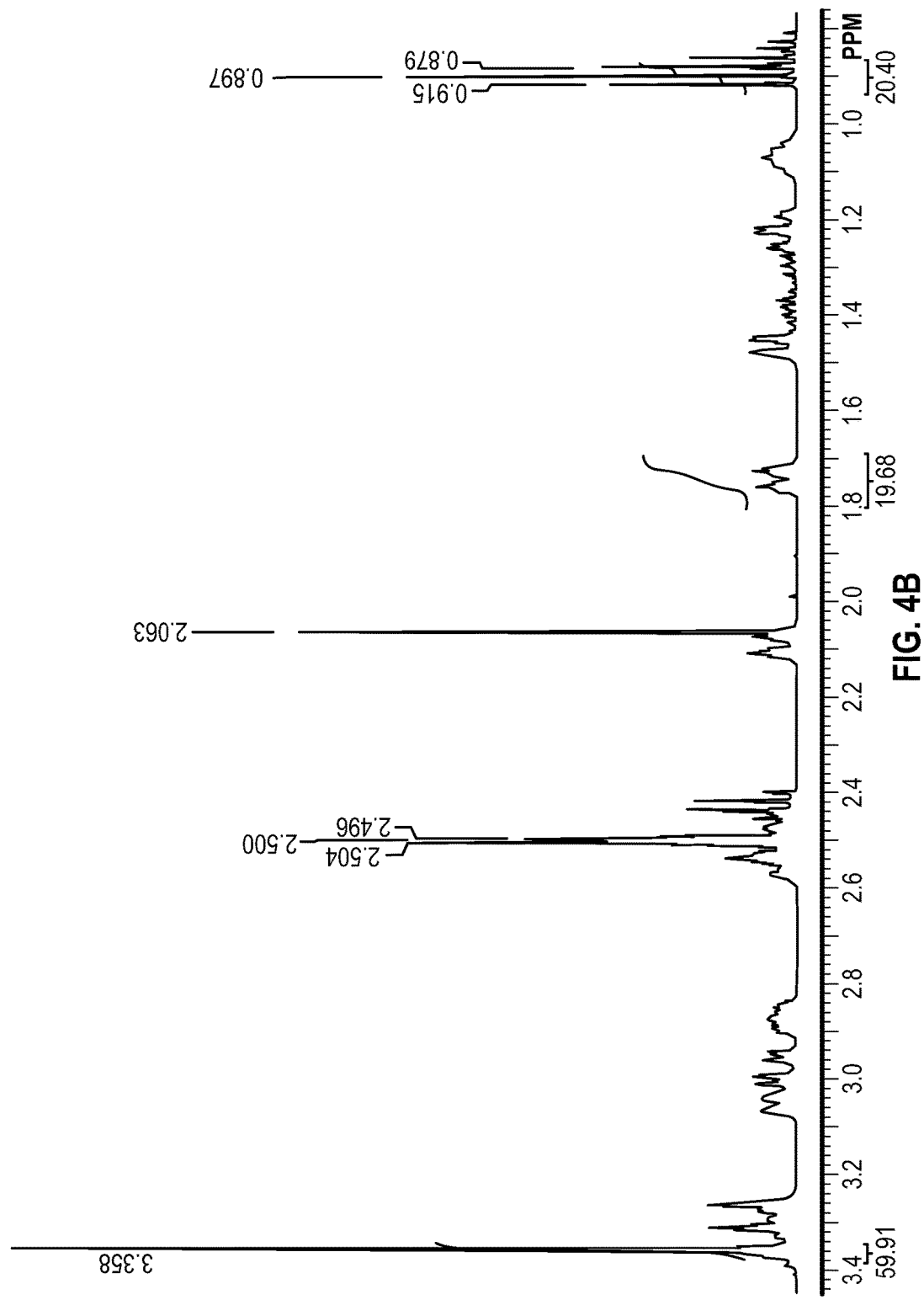
FIG. 4B is a magnified region of the NMR spectrum of FIG. 4A.
Figure 4C:
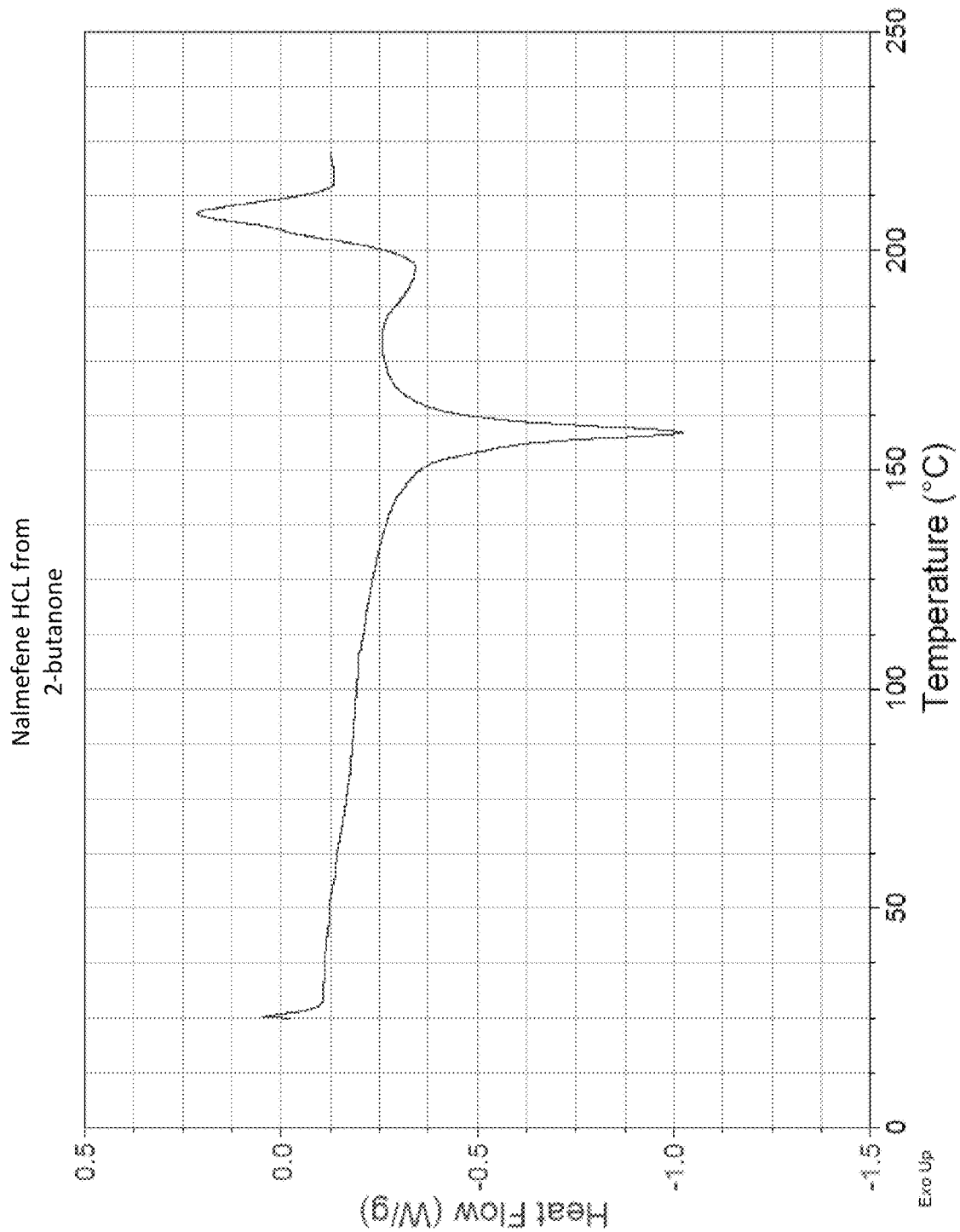
FIG. 4C is a Differential Scanning calorimetry (DC) plot measured from a sample of crystalline Nalmefene HCl recrystallized from a mixture of 2-butanone, Water, and Nalmefene HCl.
Figure 4D:
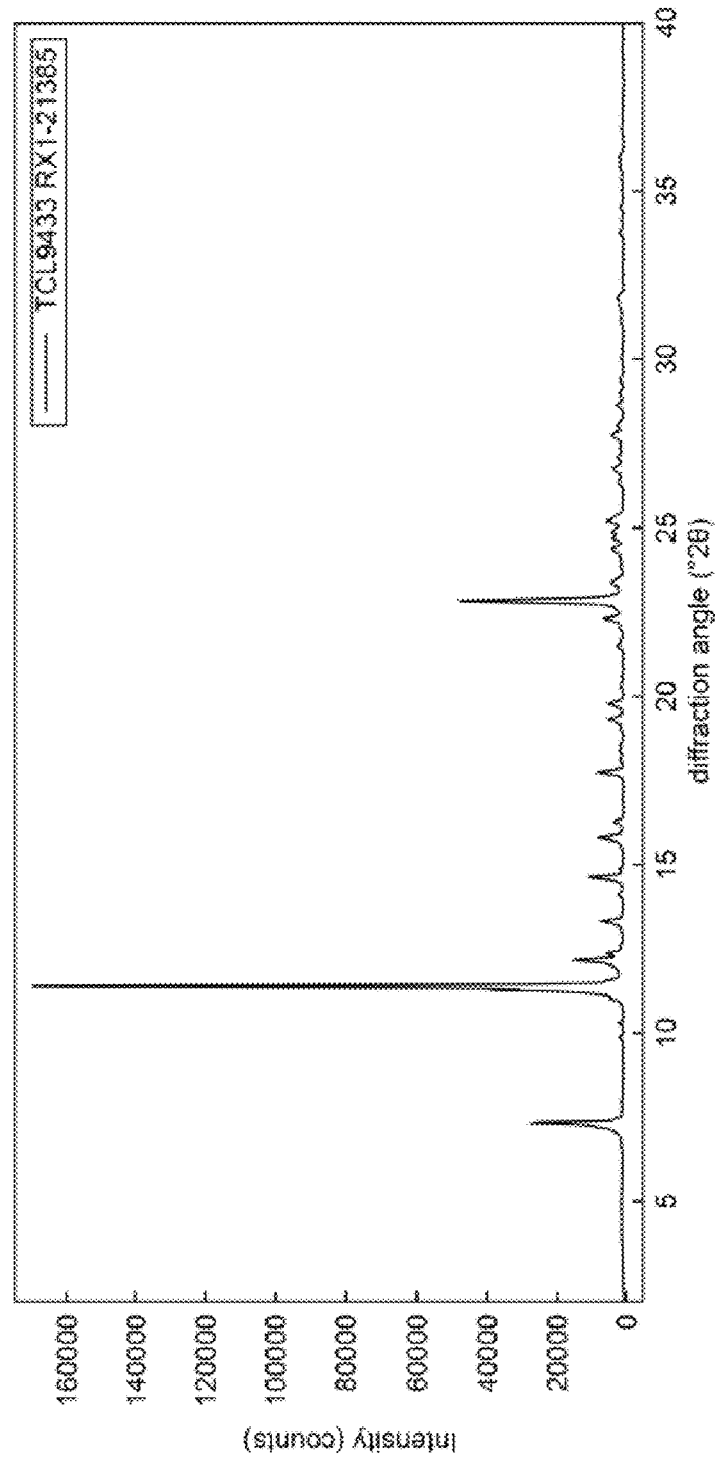
FIG. 4D is an x-ray diffraction spectrum measured from a sample of crystalline Nalmefene HCl recrystallized from a mixture of 2-butanone, Water, and Nalmefene HCl.
Figure 5A:
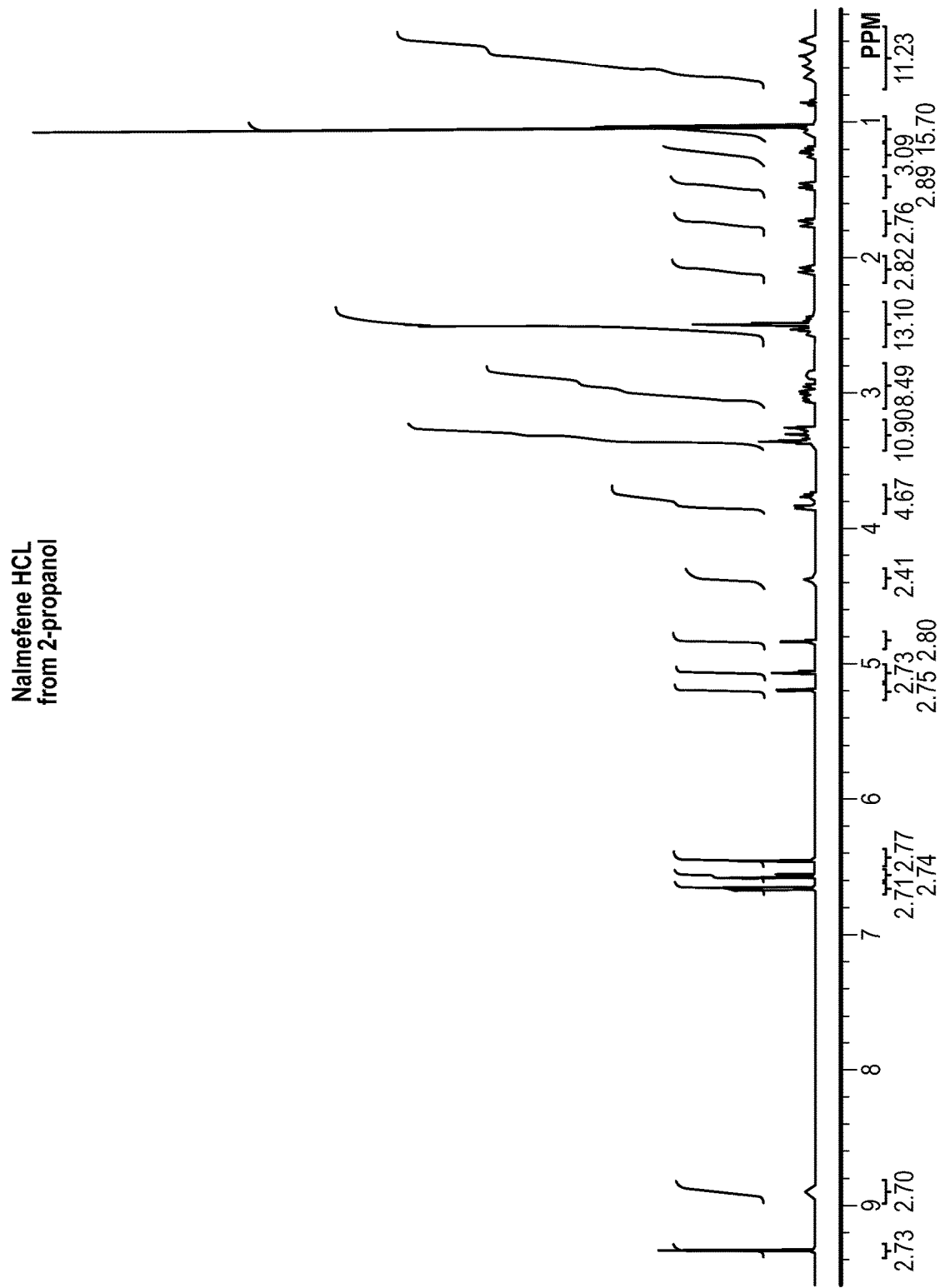
FIG. 5A is a proton nuclear magnetic resonance (NMR) spectrum measured from a sample of crystalline Nalmefene HCl recrystallized from a mixture of 2-propanol, Water, and Nalmefene HCl.
Figure 5B:
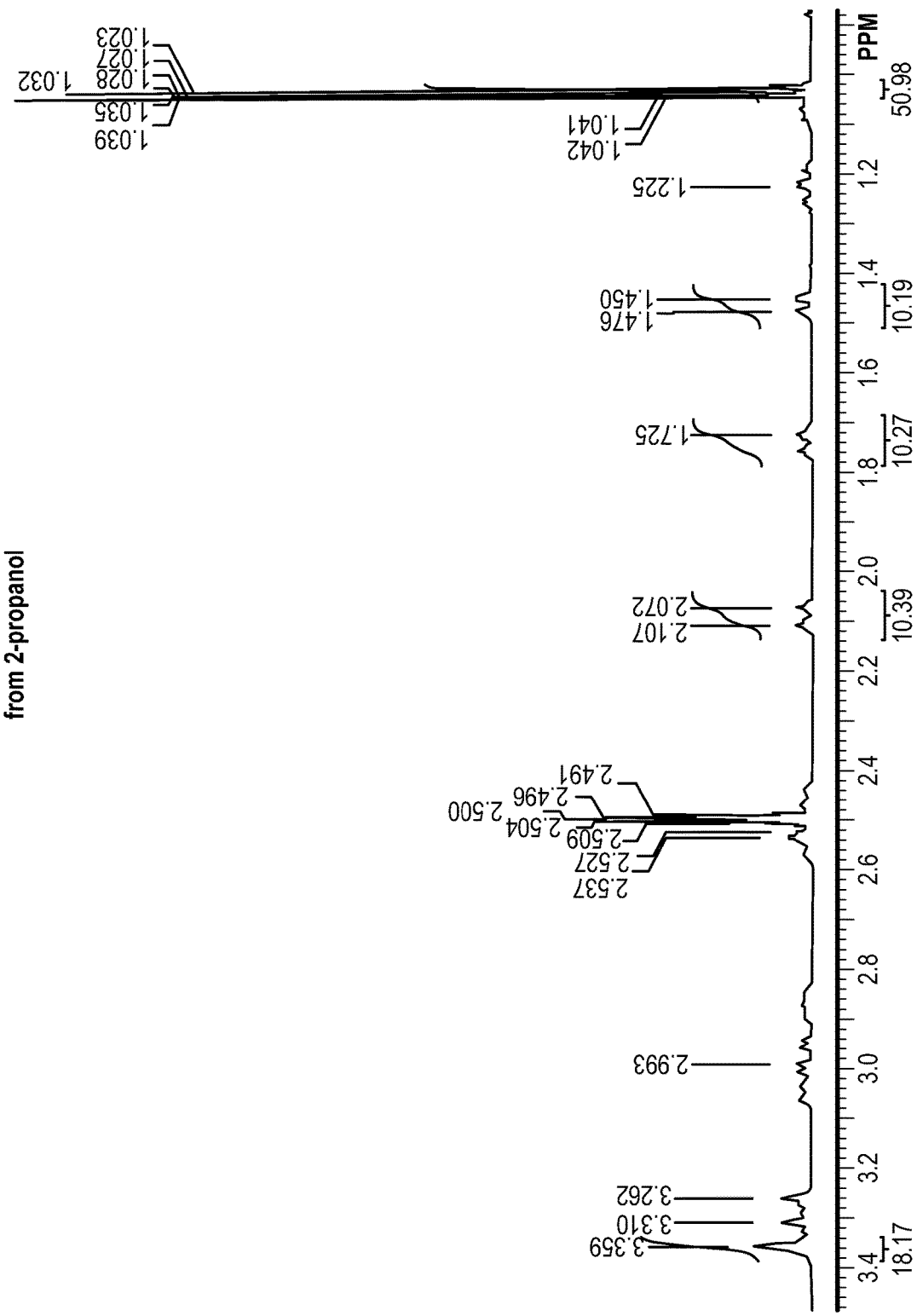
FIG. 5B is a magnified region of the NMR spectrum of FIG. 5A.
Figure 5C:
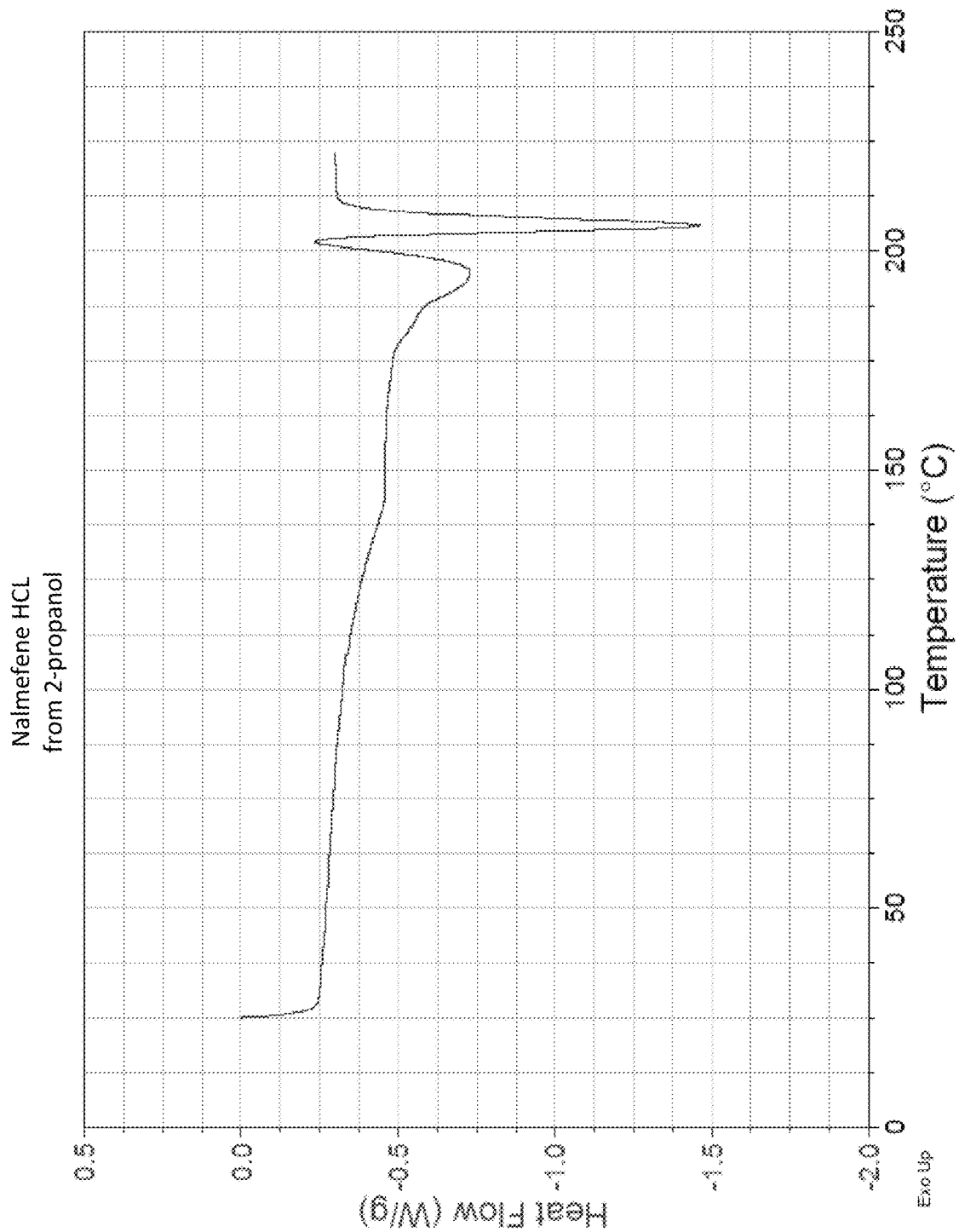
FIG. 5C is a Differential Scanning calorimetry (DC) plot measured from a sample of crystalline Nalmefene HCl recrystallized from a mixture of 2-propanol, Water, and Nalmefene HCl.
Figure 5D:
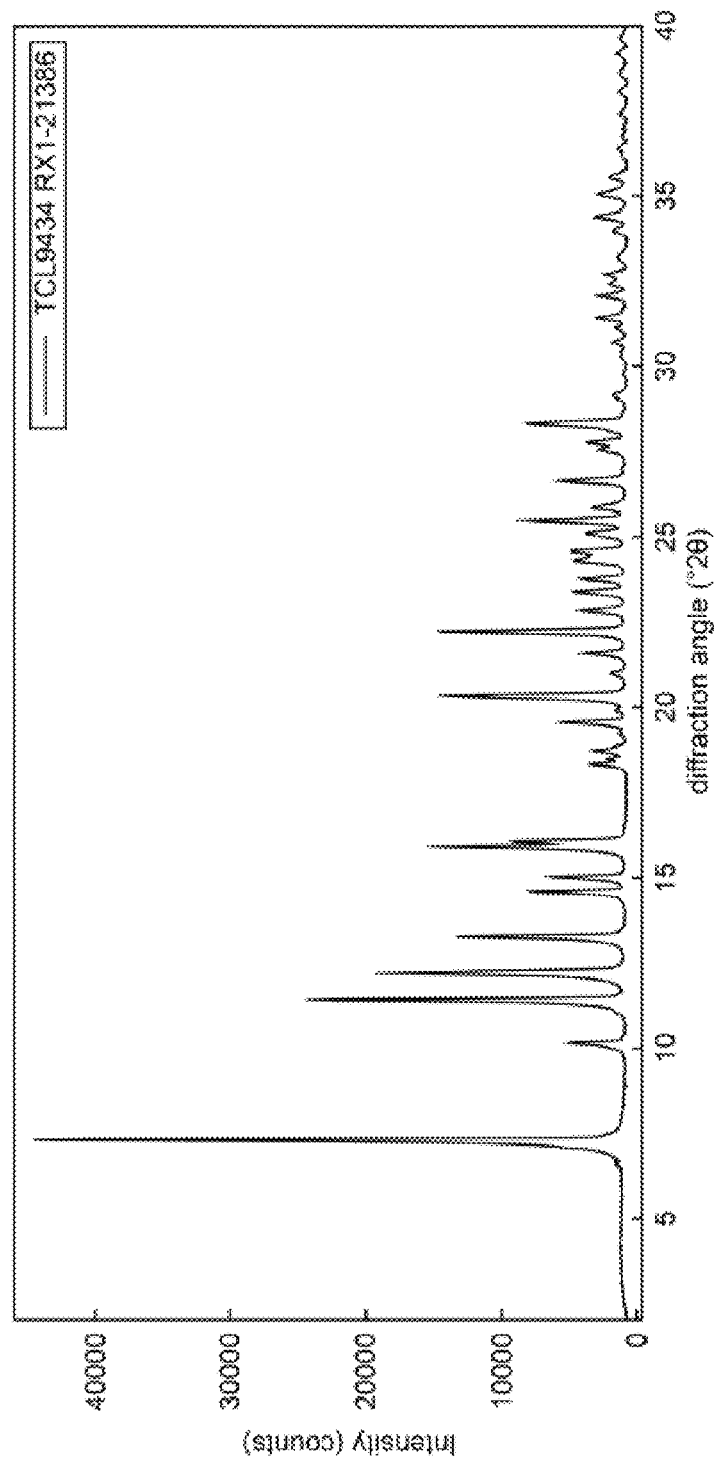
FIG. 5D is an x-ray diffraction spectrum measured from a sample of crystalline Nalmefene HCl recrystallized from a mixture of 2-propanol, Water, and Nalmefene HCl.
Figure 6A:
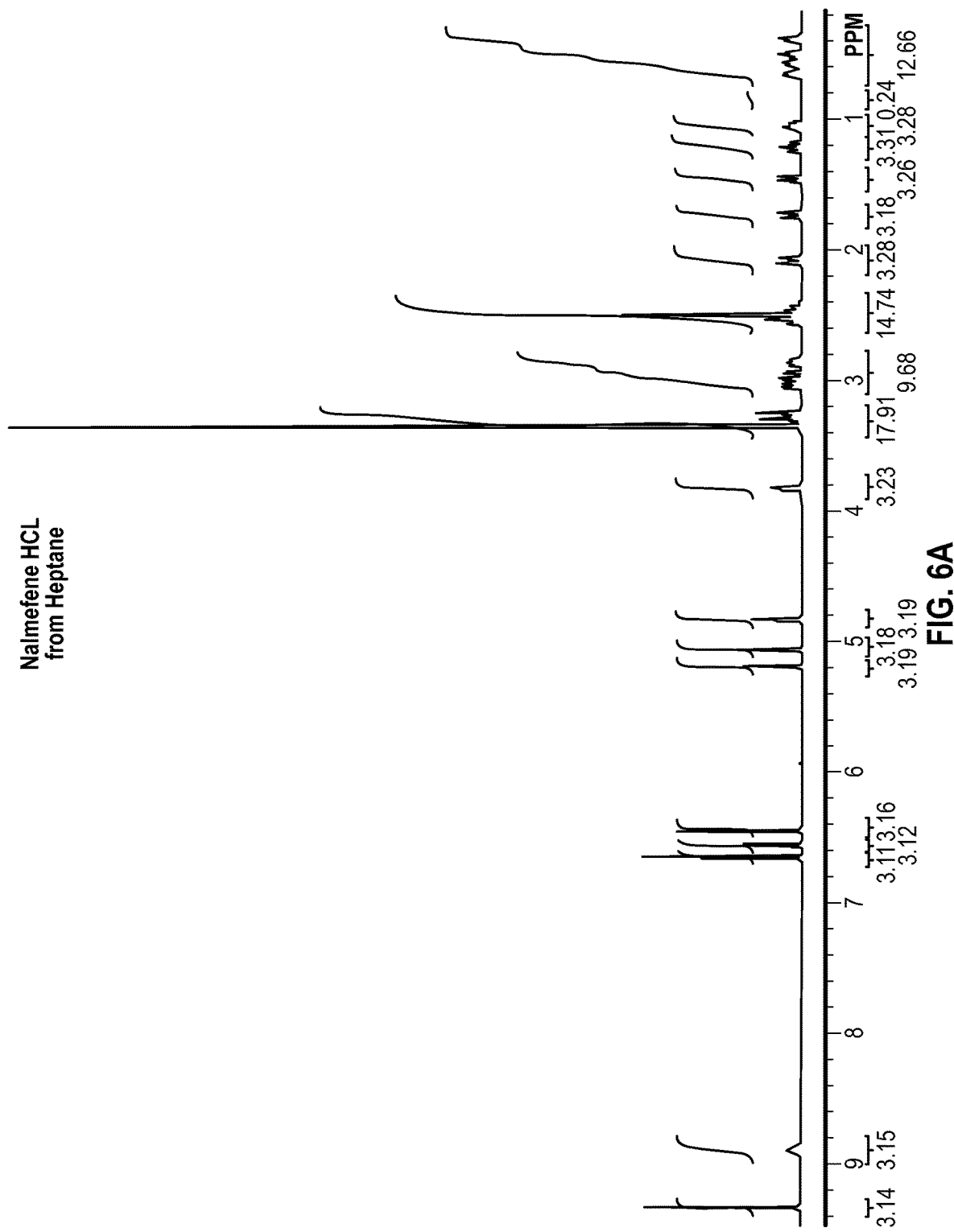
FIG. 6A is a proton nuclear magnetic resonance (NMR) spectrum measured from a sample of crystalline Nalmefene HCl recrystallized from a mixture of heptane, Water, and Nalmefene HCl.
Figure 6B:
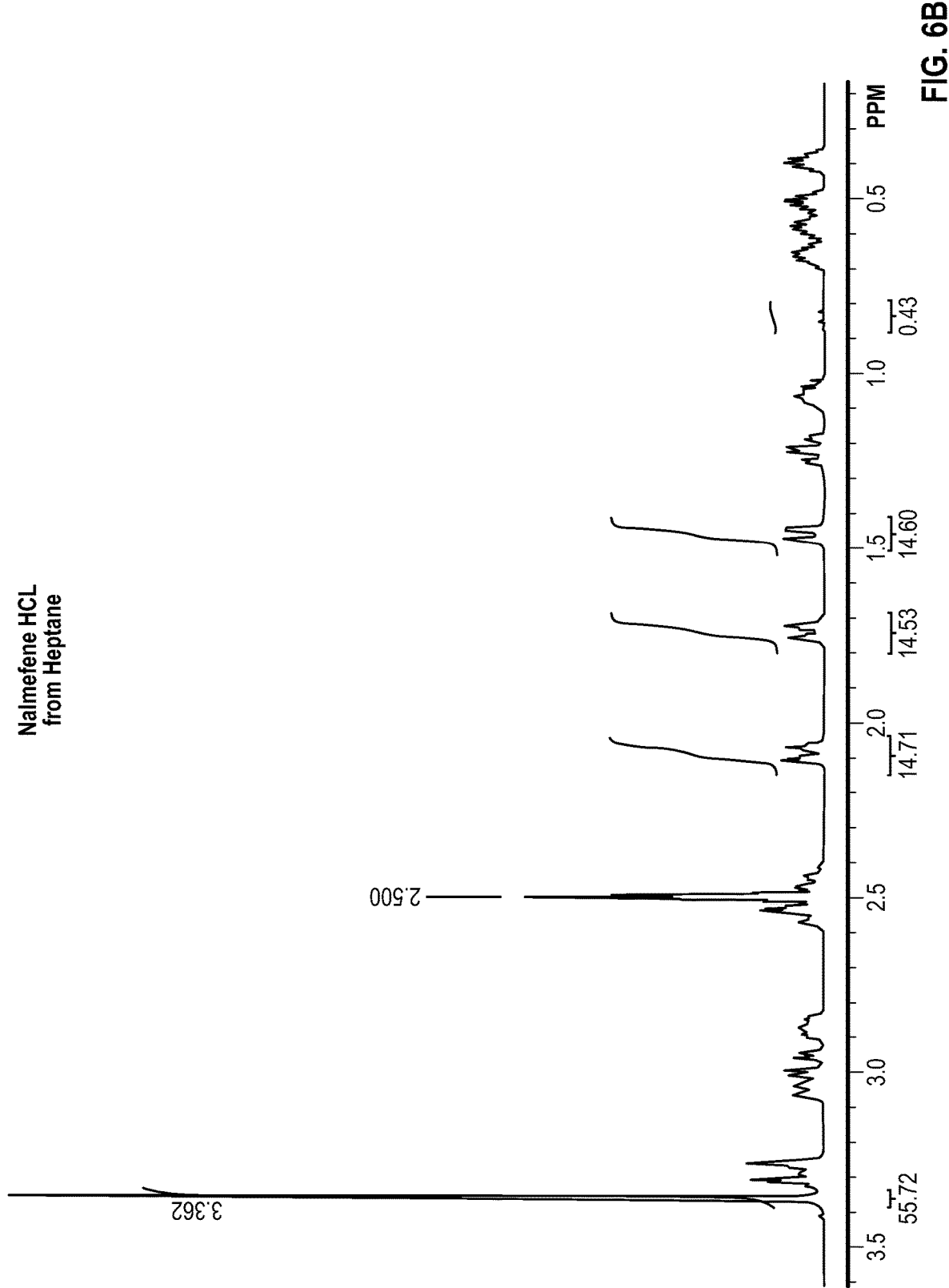
FIG. 6B is a magnified region of the NMR spectrum of FIG. 6A.
Figure 6C:
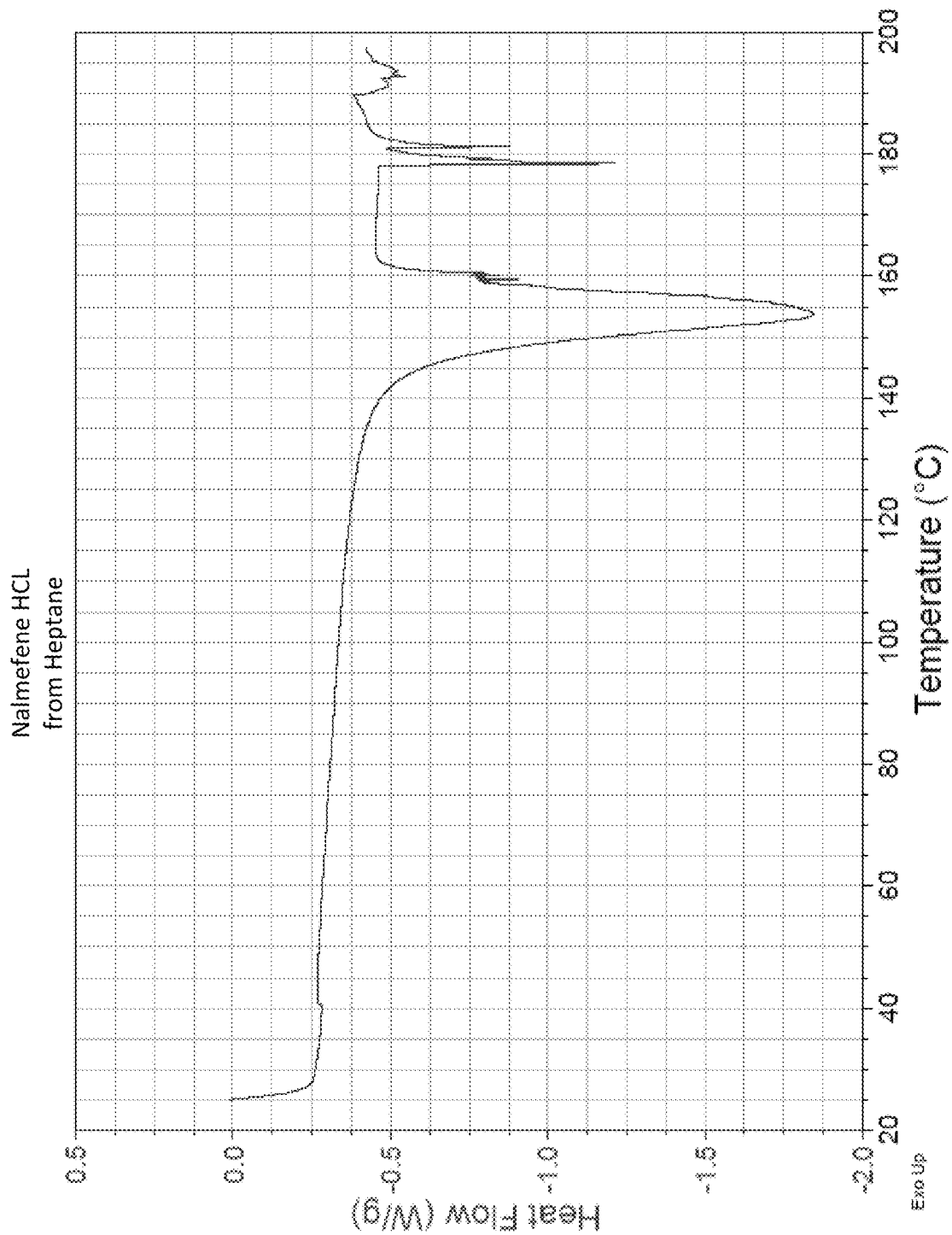
FIG. 6C is a Differential Scanning calorimetry (DC) plot measured from a sample of crystalline Nalmefene HCl recrystallized from a mixture of heptane, Water, and Nalmefene HCl.
Figure 6D:
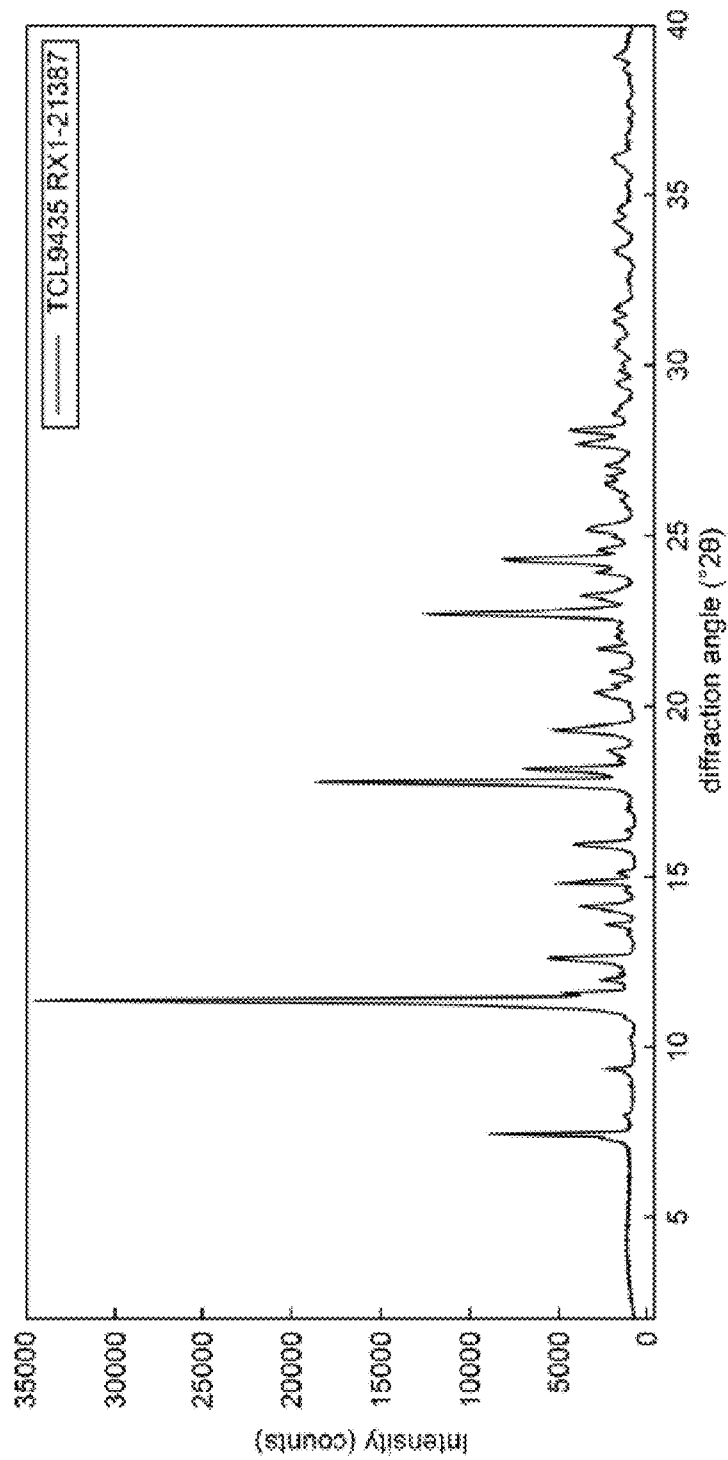
FIG. 6D is an x-ray diffraction spectrum measured from a sample of crystalline Nalmefene HCl recrystallized from a mixture of heptane, Water, and Nalmefene HCl.
Figure 7A:
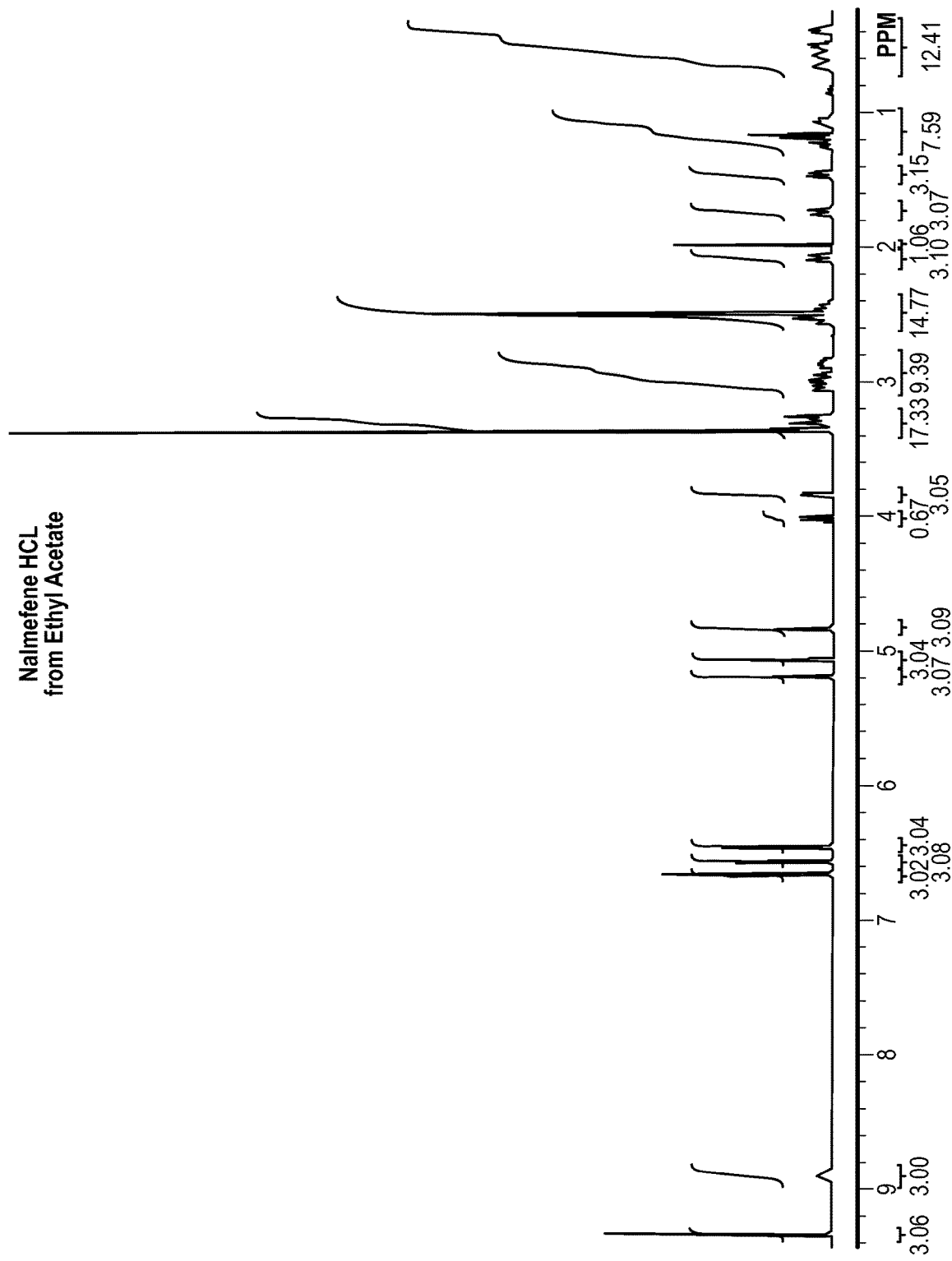
FIG. 7A is a proton nuclear magnetic resonance (NMR) spectrum measured from a sample of crystalline Nalmefene HCl recrystallized from a mixture of ethyl acetate, Water, and Nalmefene HCl.
Figure 7B:
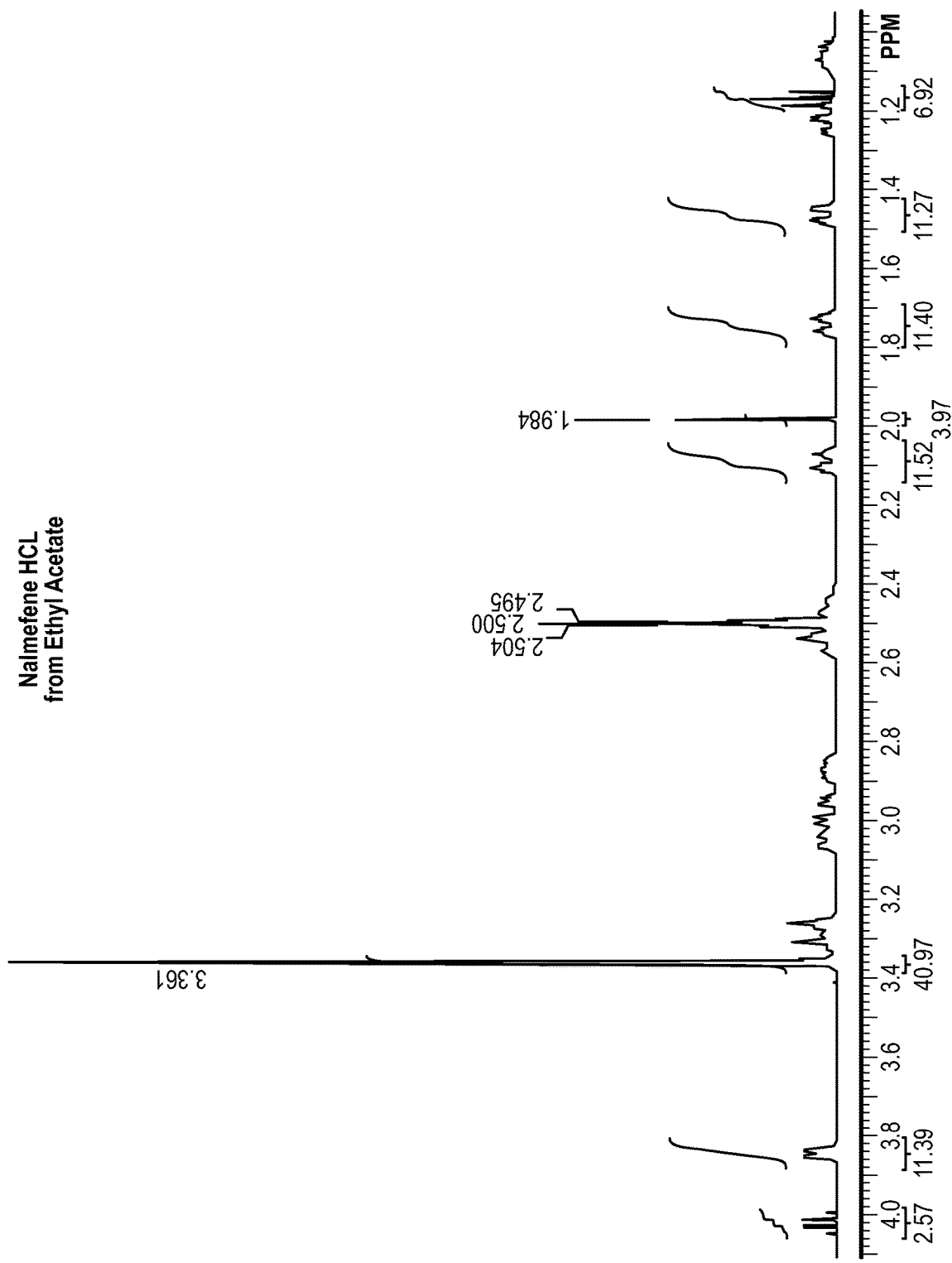
FIG. 7B is a magnified region of the NMR spectrum of FIG. 7A.
Figure 7C:
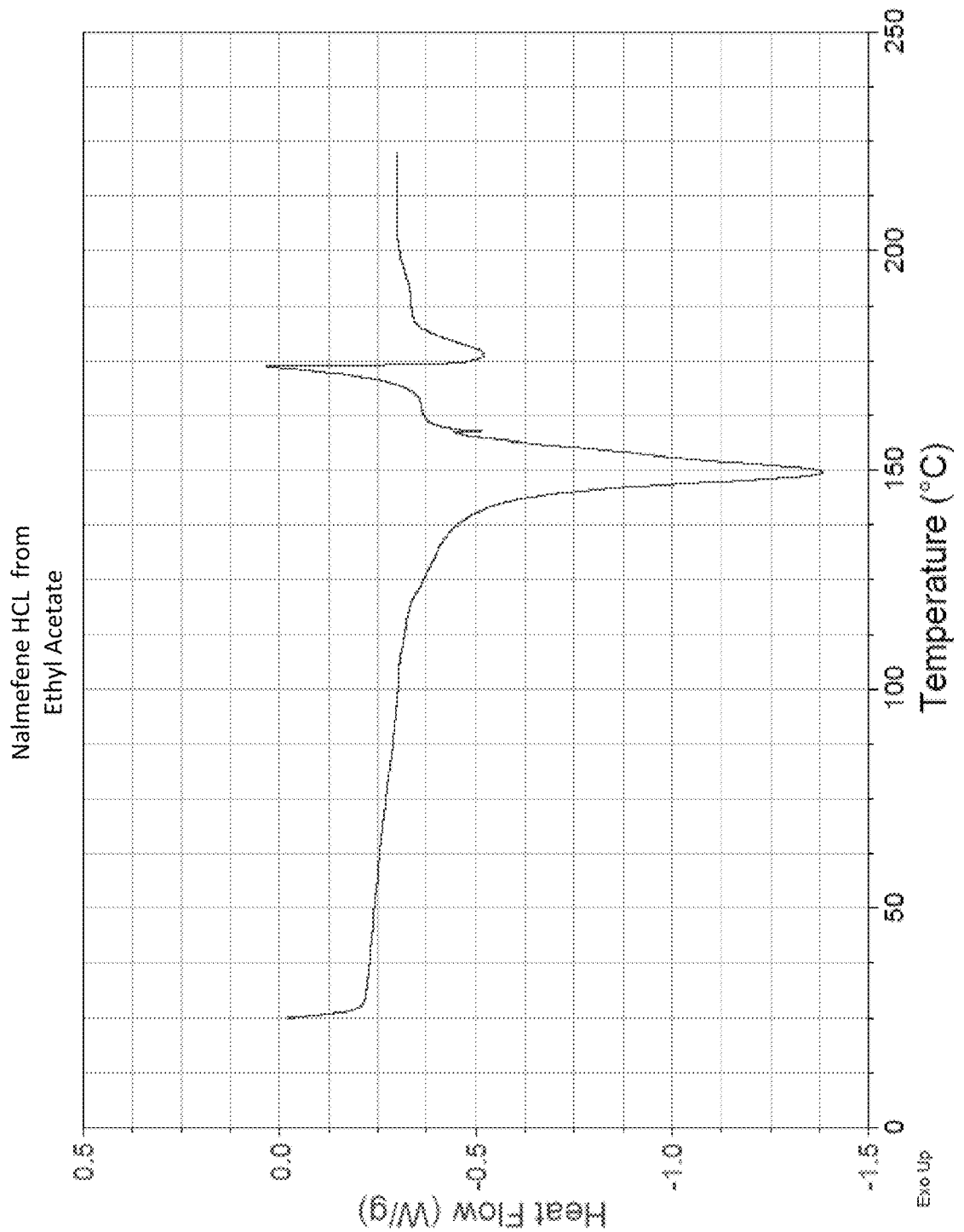
FIG. 7C is a Differential Scanning calorimetry (DC) plot measured from a sample of crystalline Nalmefene HCl recrystallized from a mixture of ethyl acetate, Water, and Nalmefene HCl.
Figure 7D:
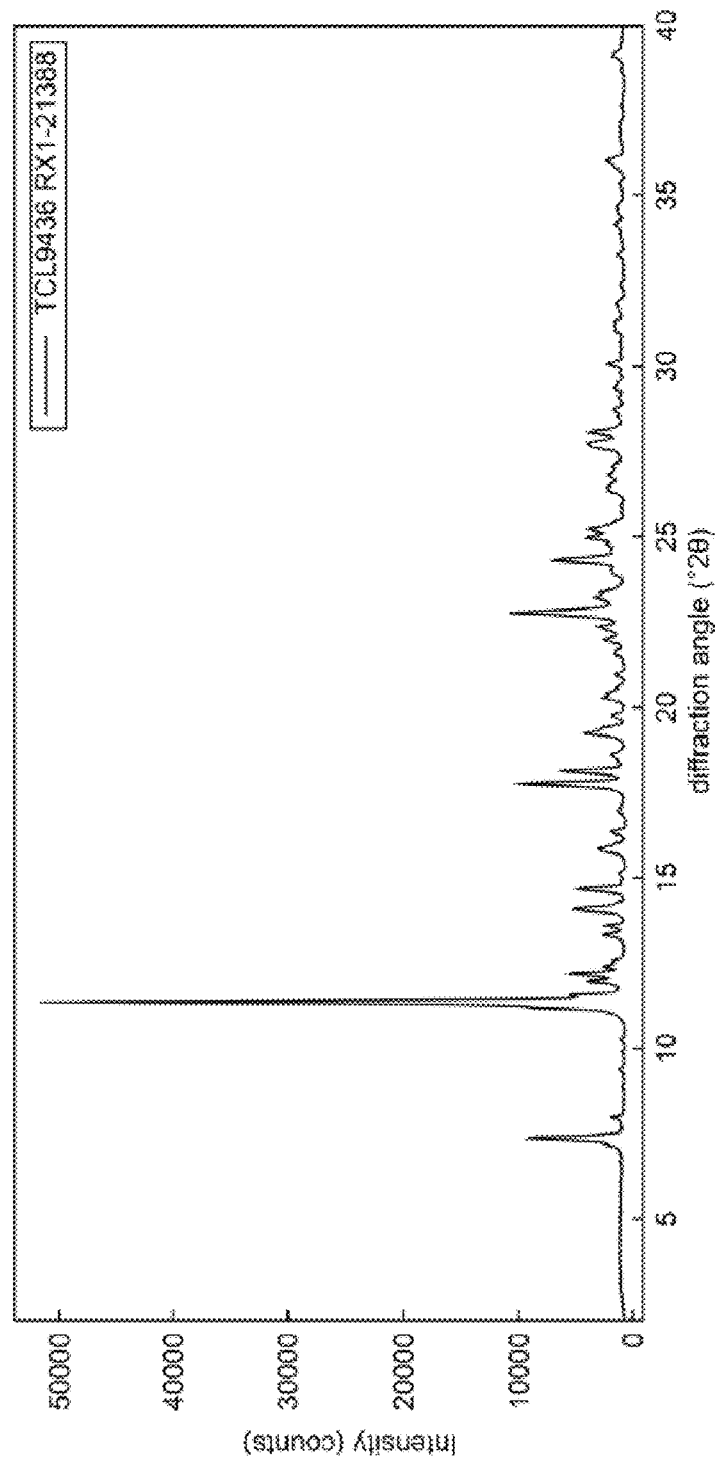
FIG. 7D is an x-ray diffraction spectrum measured from a sample of crystalline Nalmefene HCl recrystallized from a mixture of ethyl acetate, Water, and Nalmefene HCl.
Figure 8A:
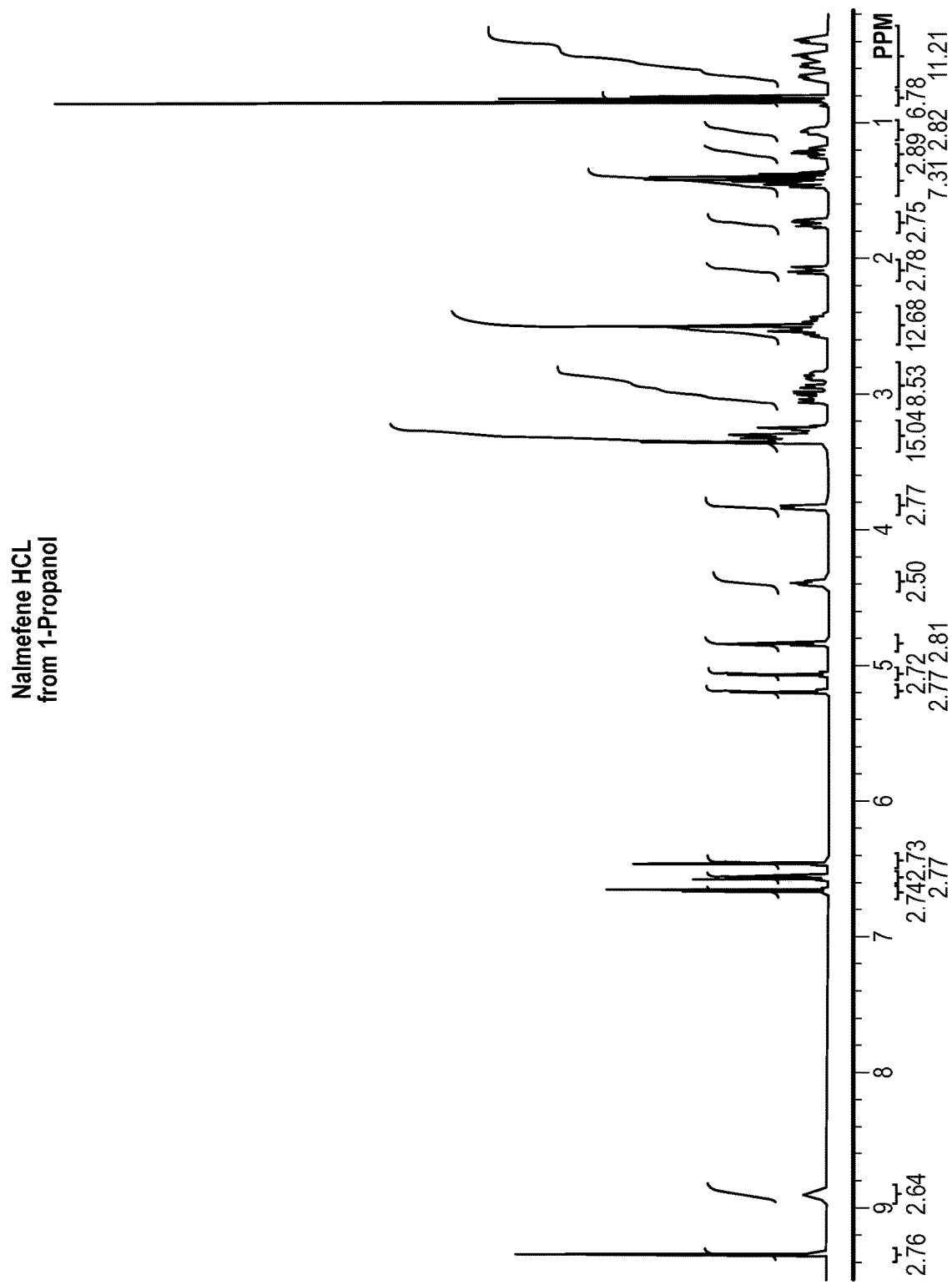
FIG. 8A is a proton nuclear magnetic resonance (NMR) spectrum measured from a sample of crystalline Nalmefene HCl recrystallized from a mixture of 1-propanol, Water, and Nalmefene HCl.
Figure 8B:
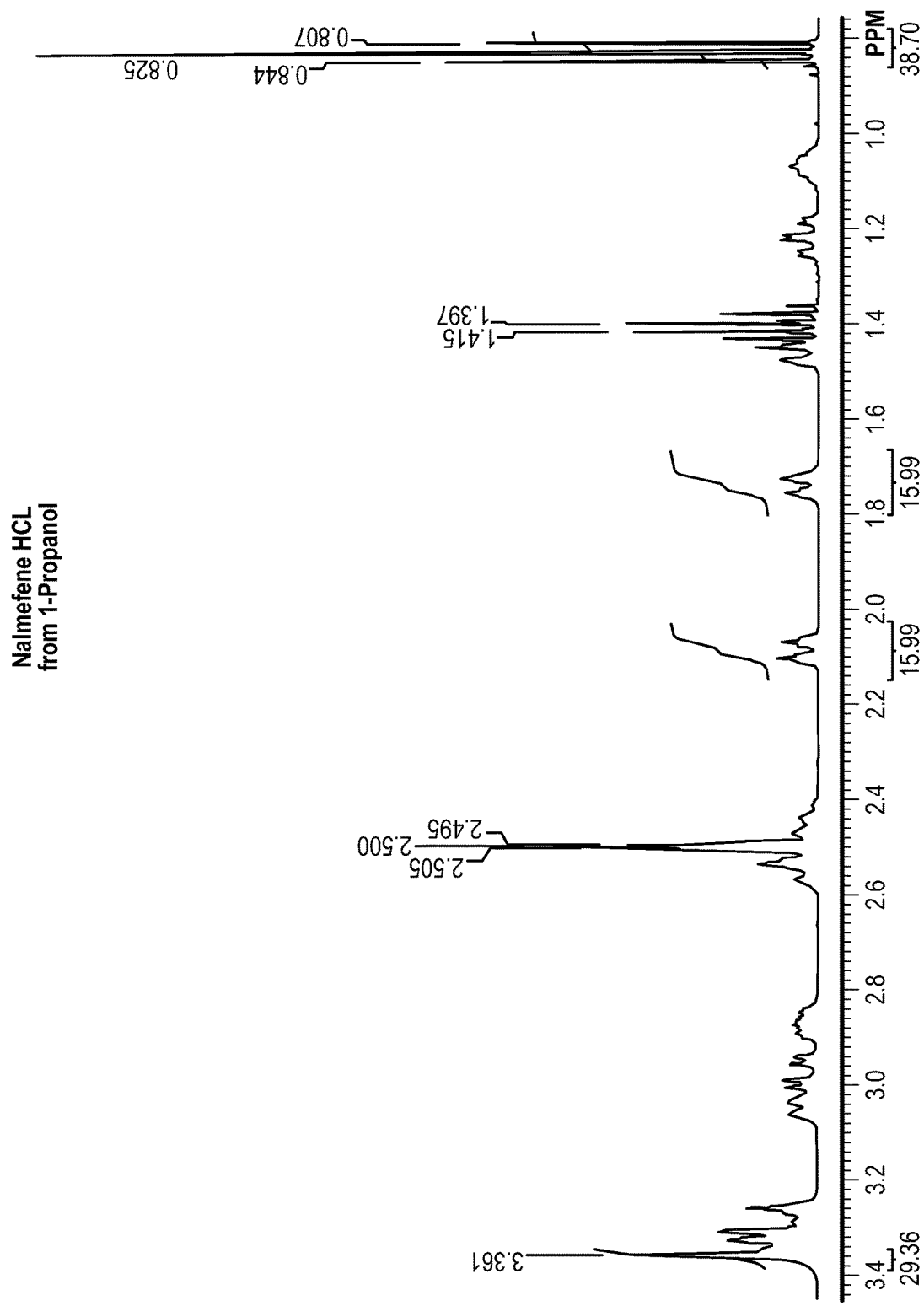
FIG. 8B is a magnified region of the NMR spectrum of FIG. 8A.
Figure 8C:
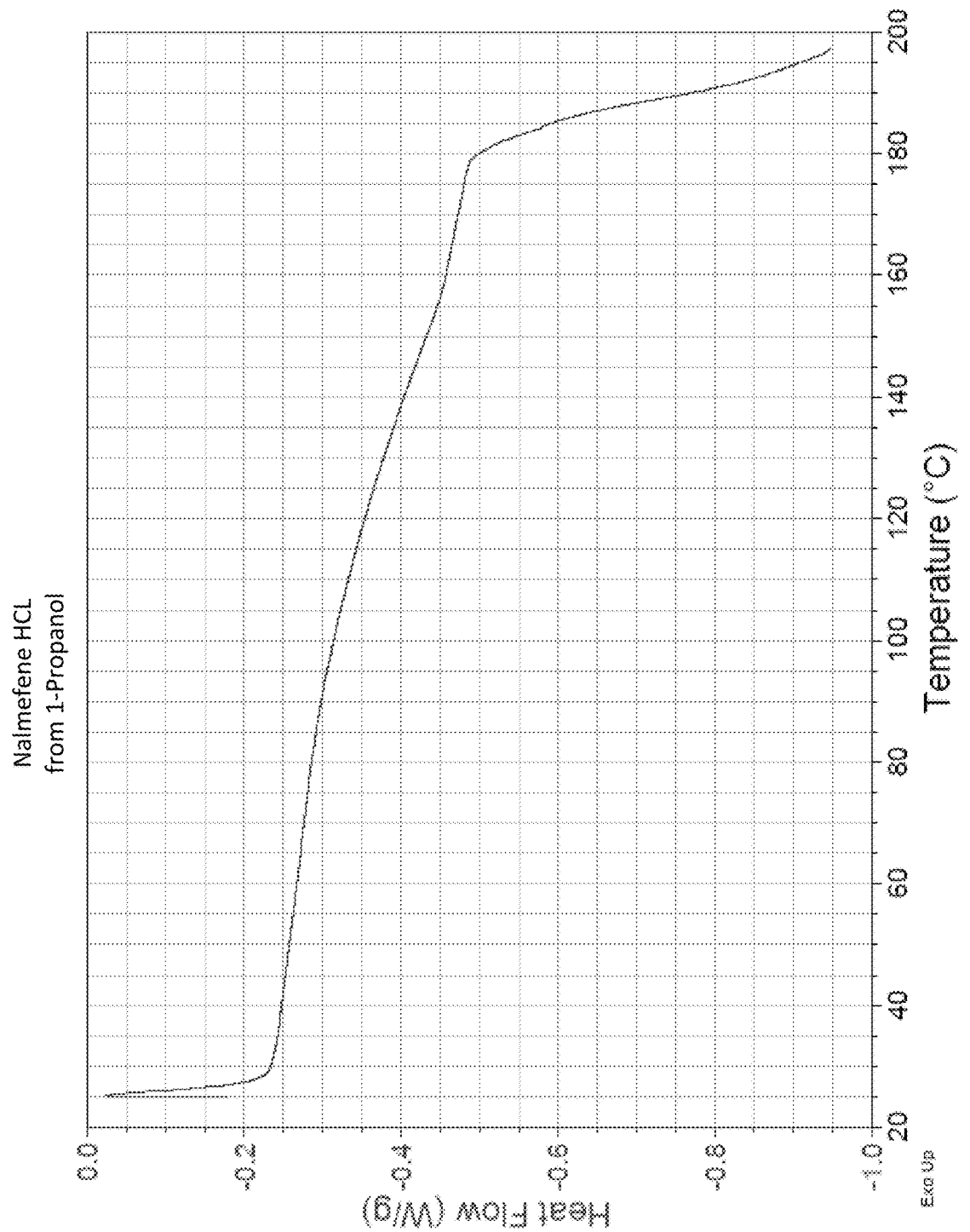
FIG. 8C is a Differential Scanning calorimetry (DC) plot measured from a sample of crystalline Nalmefene HCl recrystallized from a mixture of 1-propanol, Water, and Nalmefene HCl.
Figure 8D:
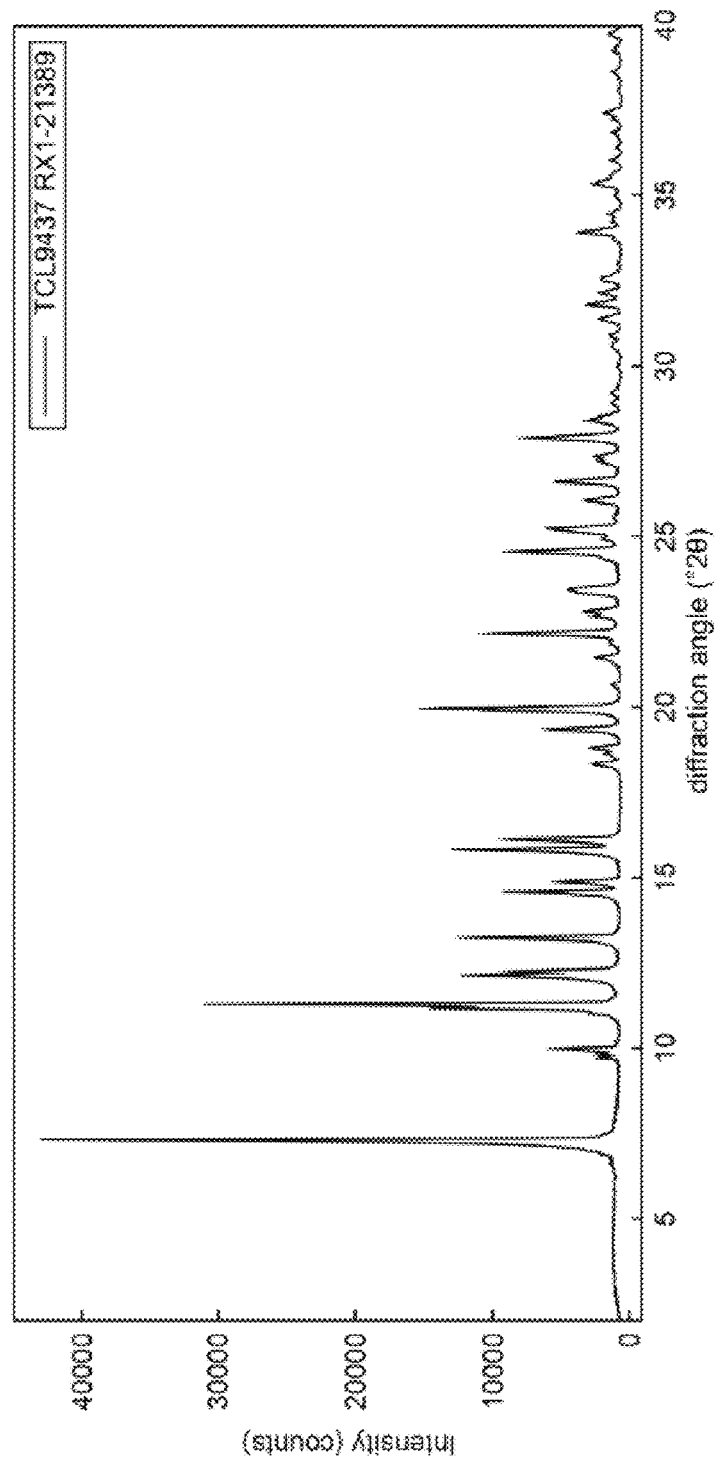
FIG. 8D is an x-ray diffraction spectrum measured from a sample of crystalline Nalmefene HCl recrystallized from a mixture of 1-propanol, Water, and Nalmefene HCl.
Figure 9B:
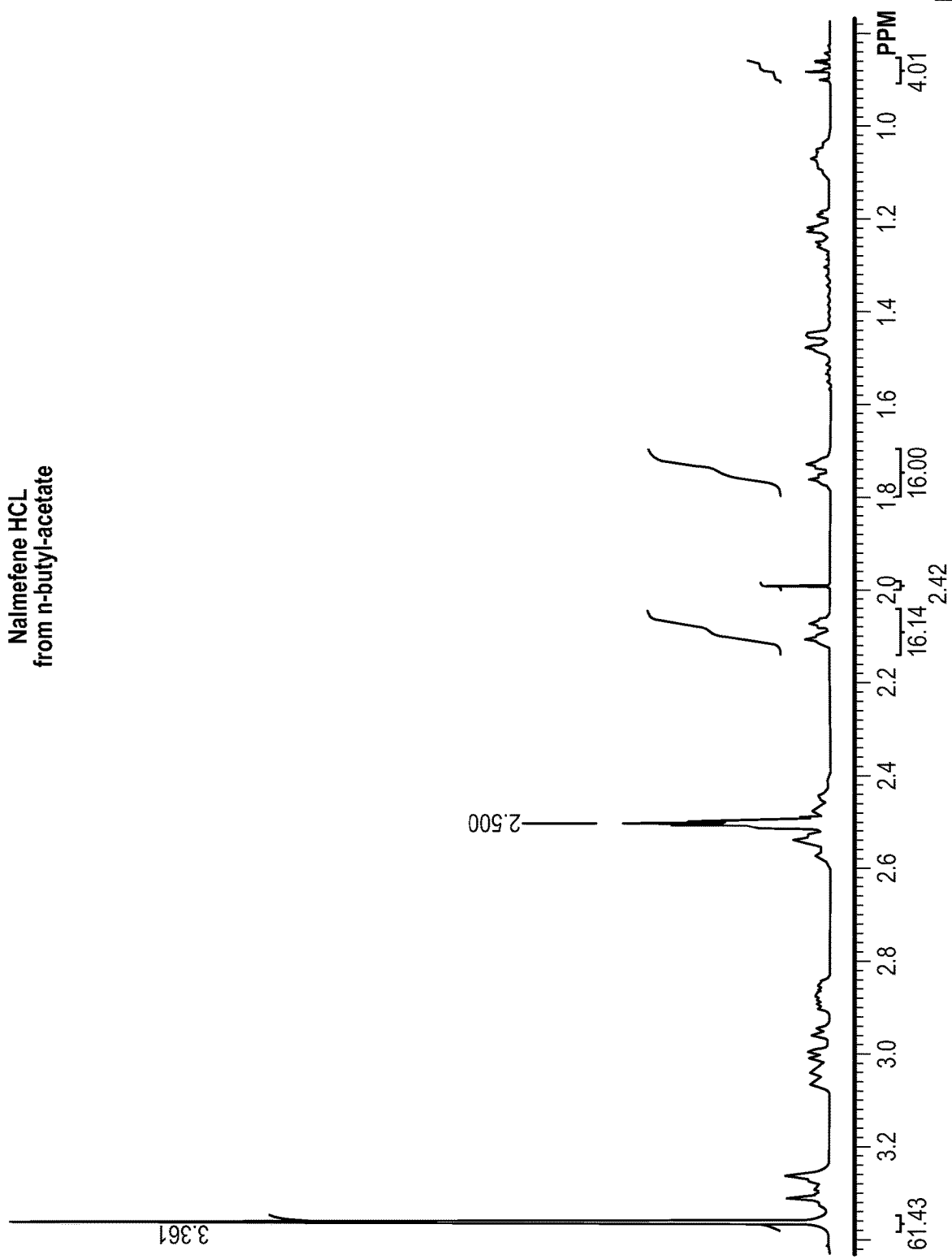
FIG. 9B is a magnified region of the NMR spectrum of FIG. 9A.
Figure 9C:
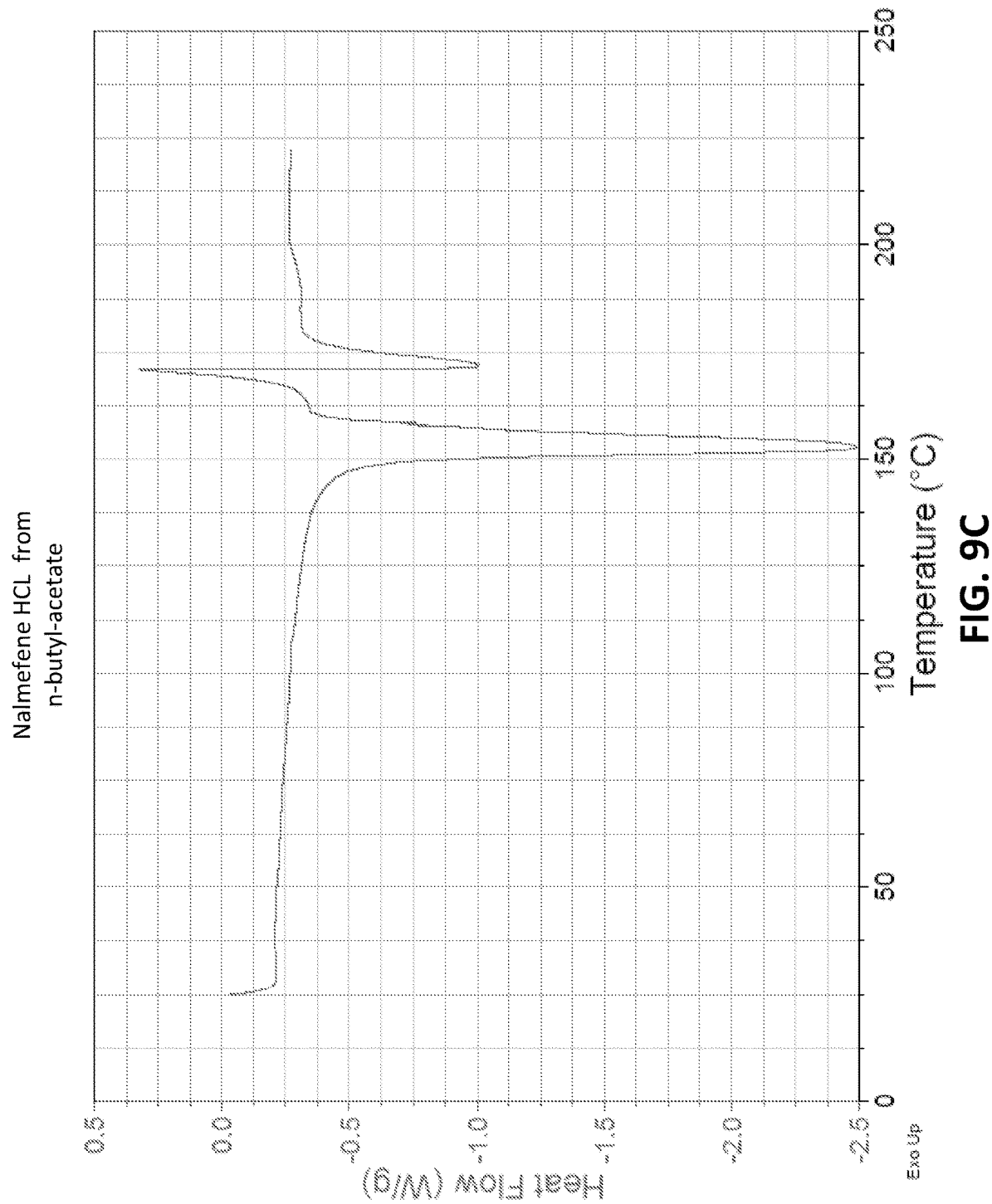
FIG. 9C is a Differential Scanning calorimetry (DC) plot measured from a sample of crystalline Nalmefene HCl recrystallized from a mixture of n-butyl-acetate, Water, and Nalmefene HCl.
Figure 9D:
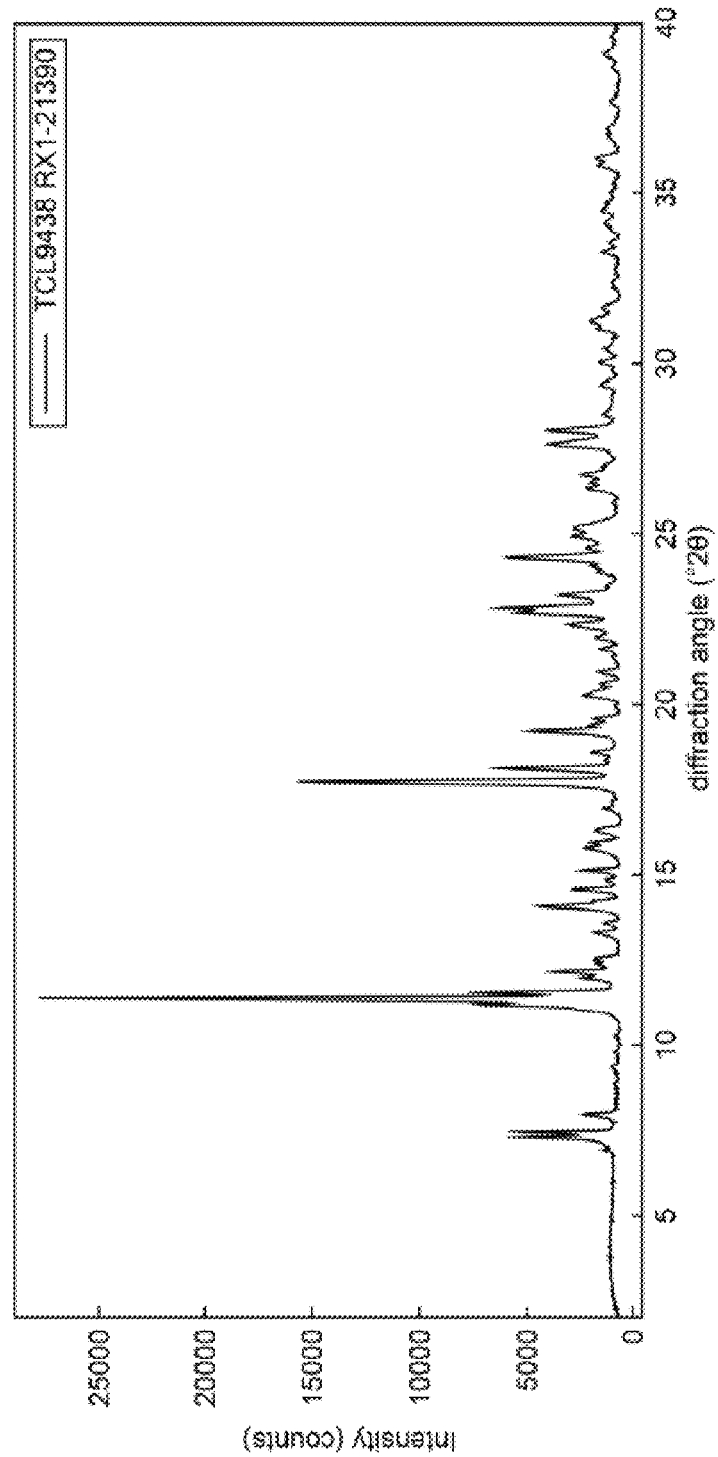
FIG. 9D is an x-ray diffraction spectrum measured from a sample of crystalline Nalmefene HCl recrystallized from a mixture of n-butyl-acetate, Water, and Nalmefene HCl.
Figure 10A:
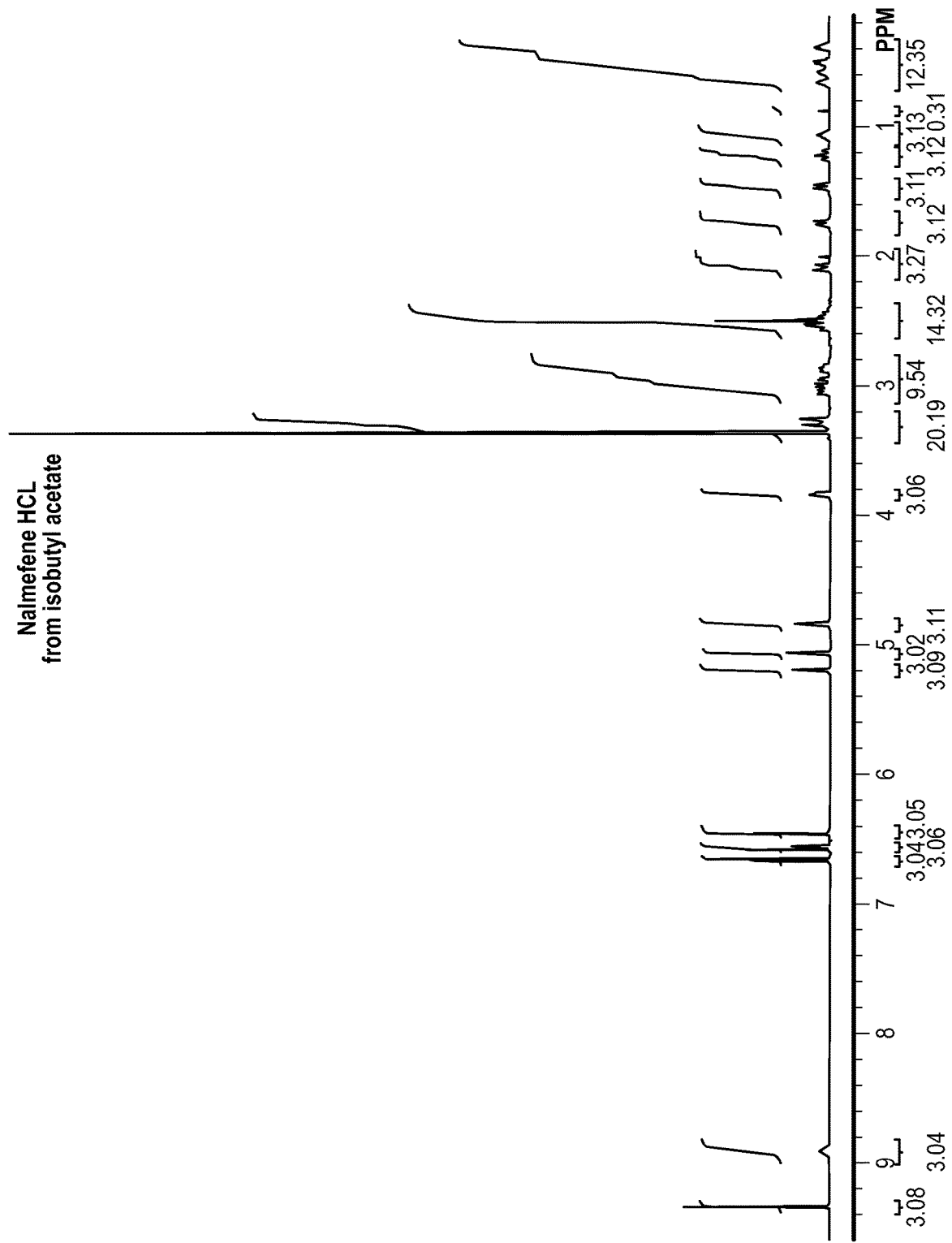
FIG. 10A is a proton nuclear magnetic resonance (NMR) spectrum measured from a sample of crystalline Nalmefene HCl recrystallized from a mixture of isobutyl acetate, Water, and Nalmefene HCl.
Figure 10B:
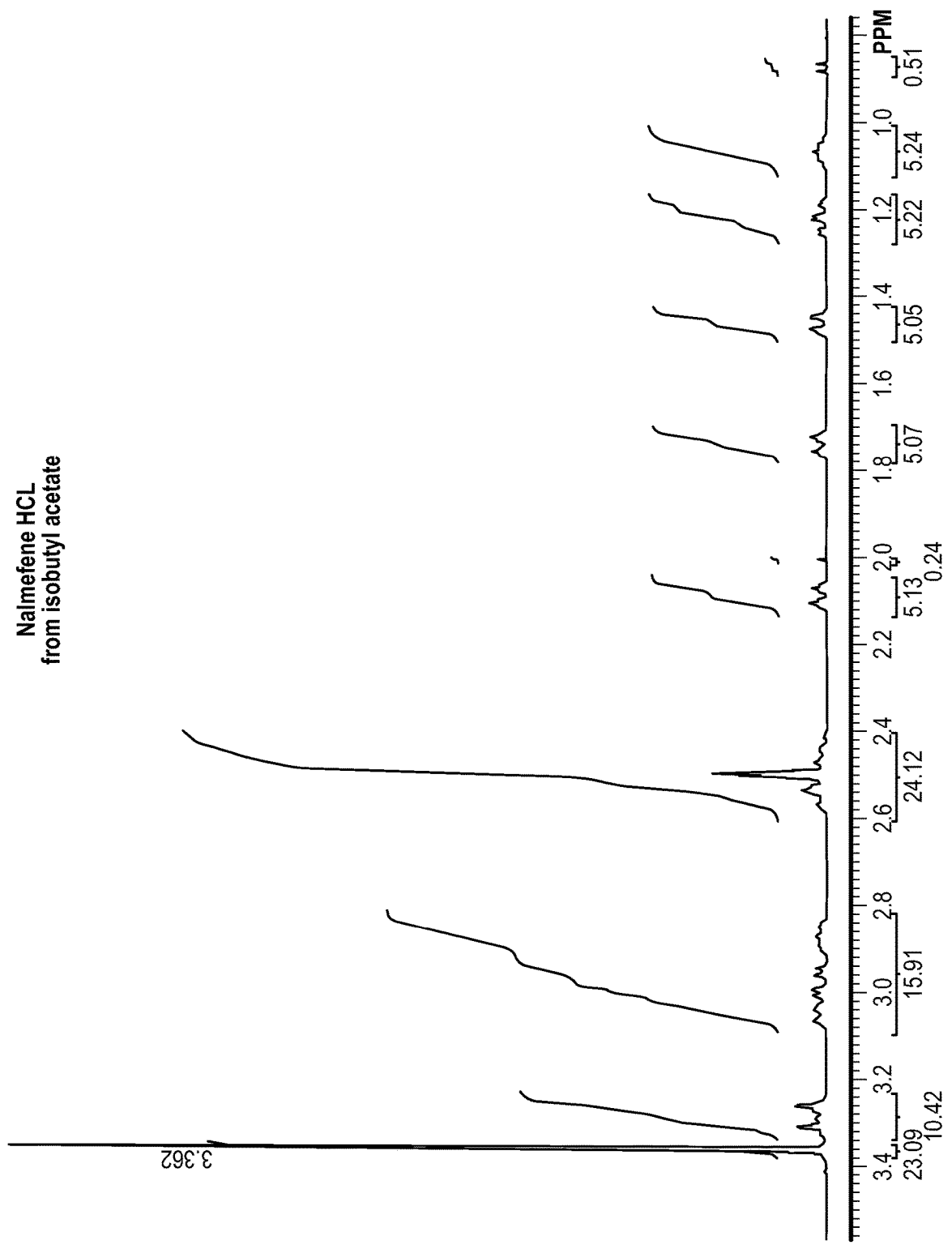
FIG. 10B is a magnified region of the NMR spectrum of FIG. 10A.
Figure 10D:
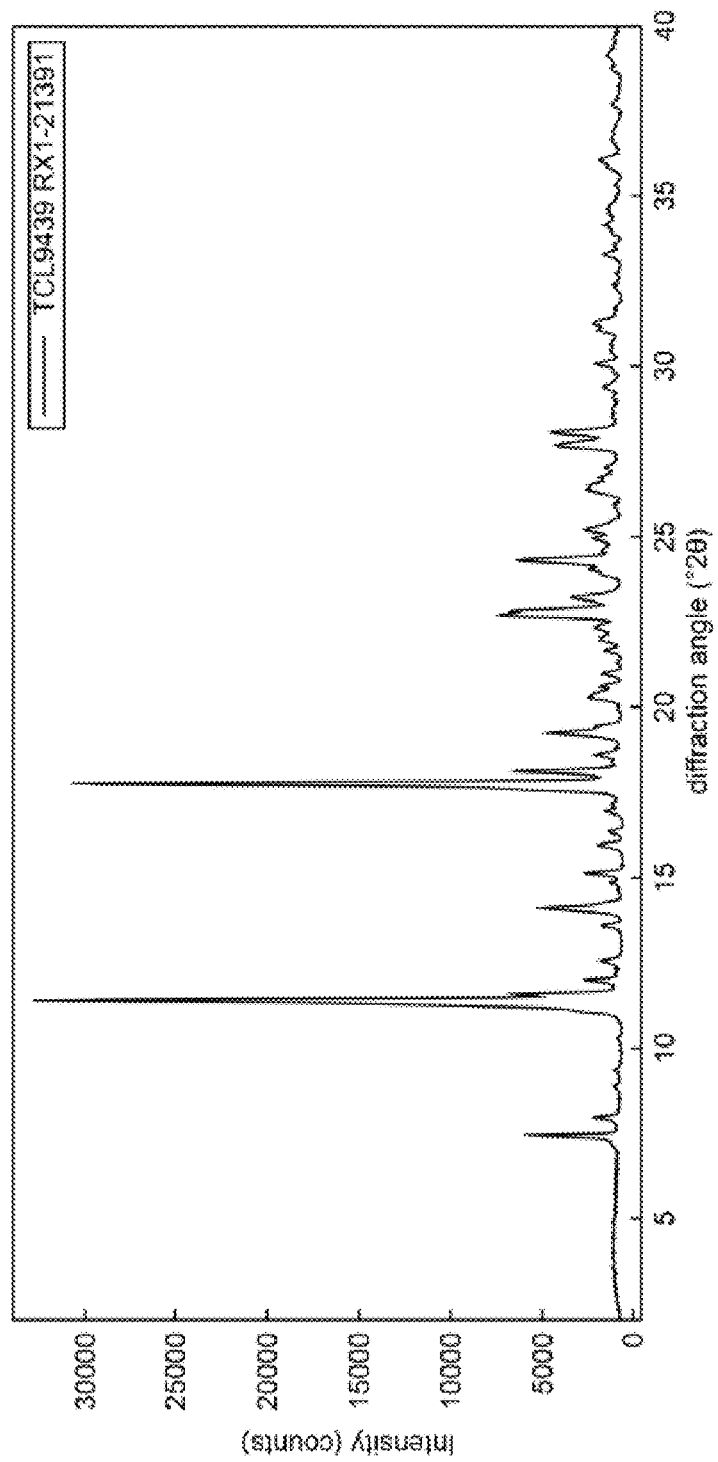
FIG. 10D is an x-ray diffraction spectrum measured from a sample of crystalline Nalmefene HCl recrystallized from a solution of isobutyl acetate, Water, and Nalmefene HCl.
Figure 11A:
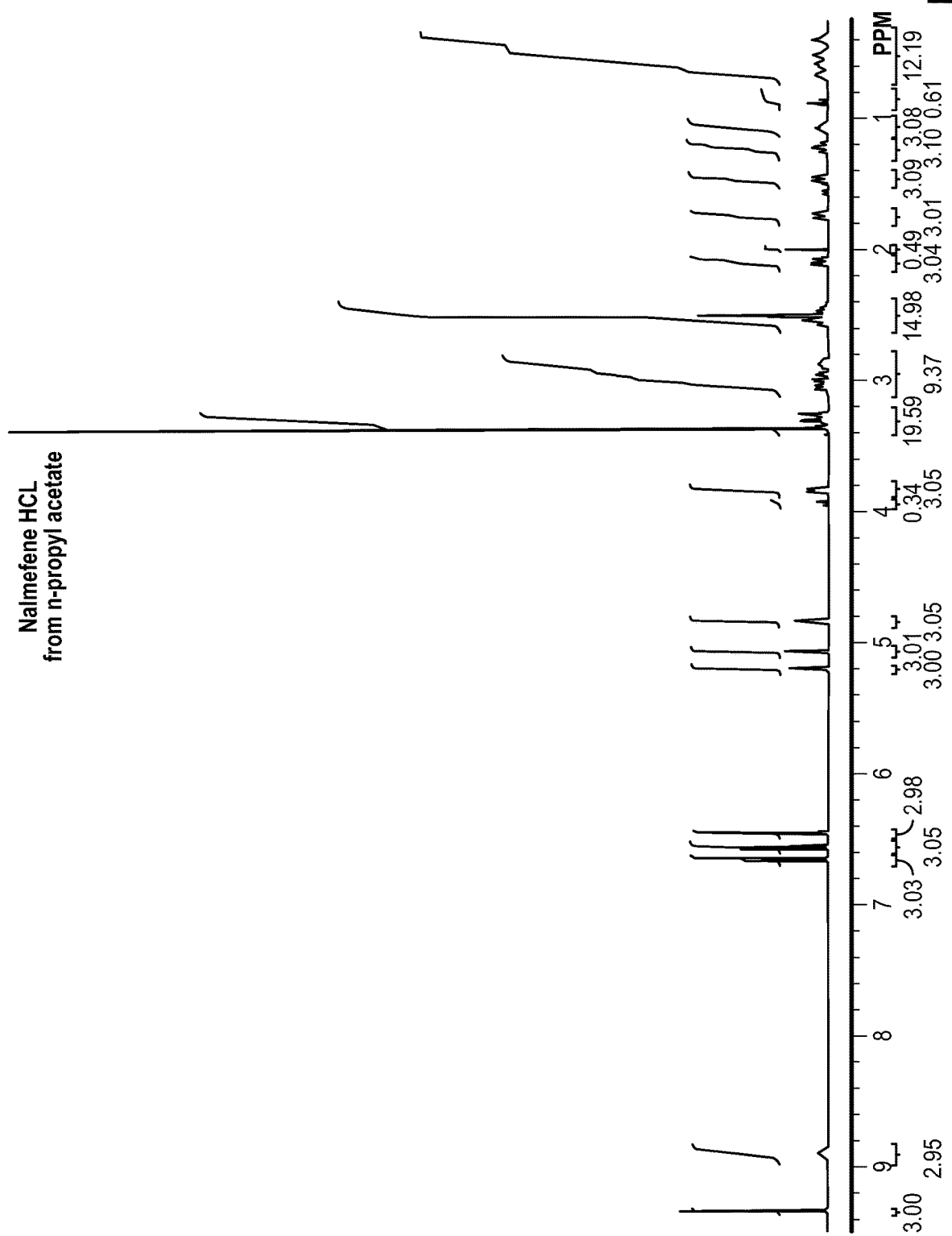
FIG. 11A is a proton nuclear magnetic resonance (NMR) spectrum measured from a sample of crystalline Nalmefene HCl recrystallized from a solution of n-propyl acetate, Water, and Nalmefene HCl.
Figure 11D:
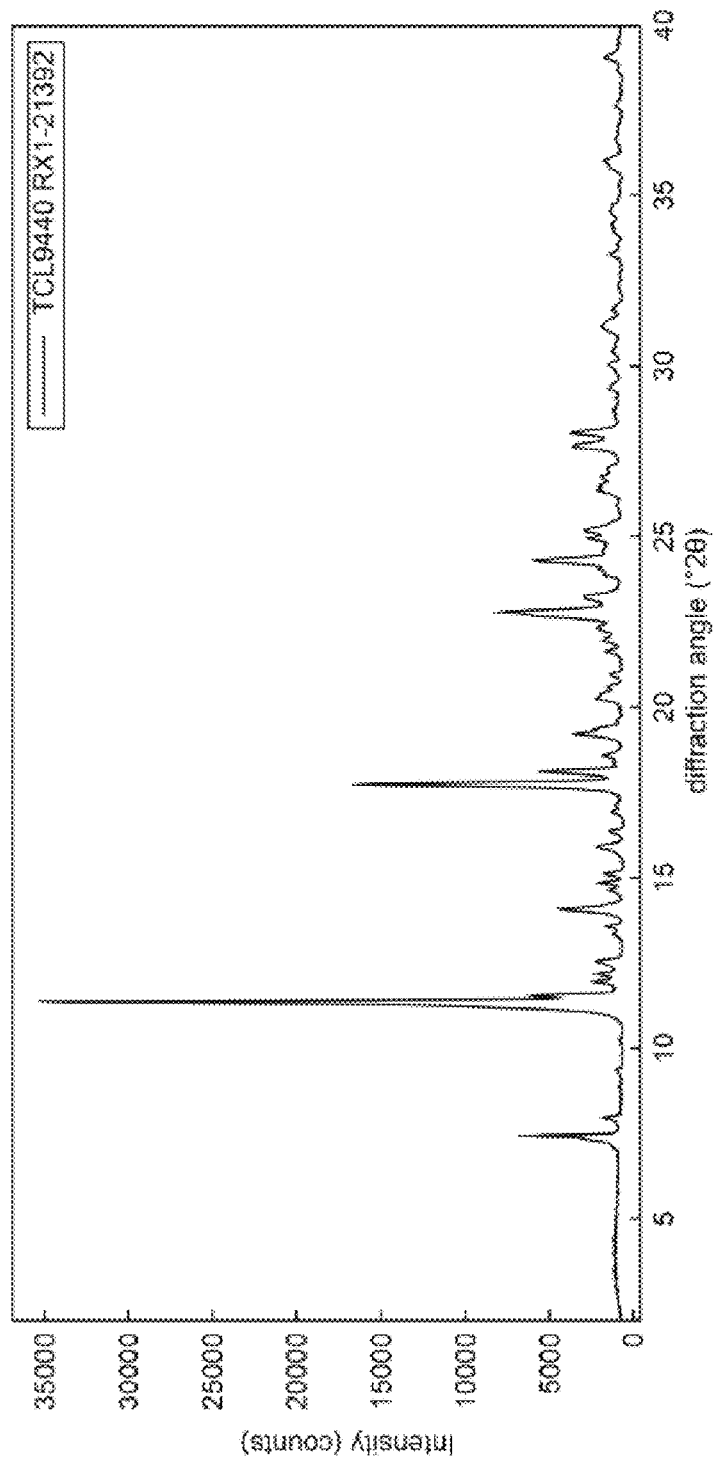
FIG. 11D is an x-ray diffraction spectrum measured from a sample of crystalline Nalmefene HCl recrystallized from a solution of n-propyl acetate, Water, and Nalmefene HCl.
Figure 12A:
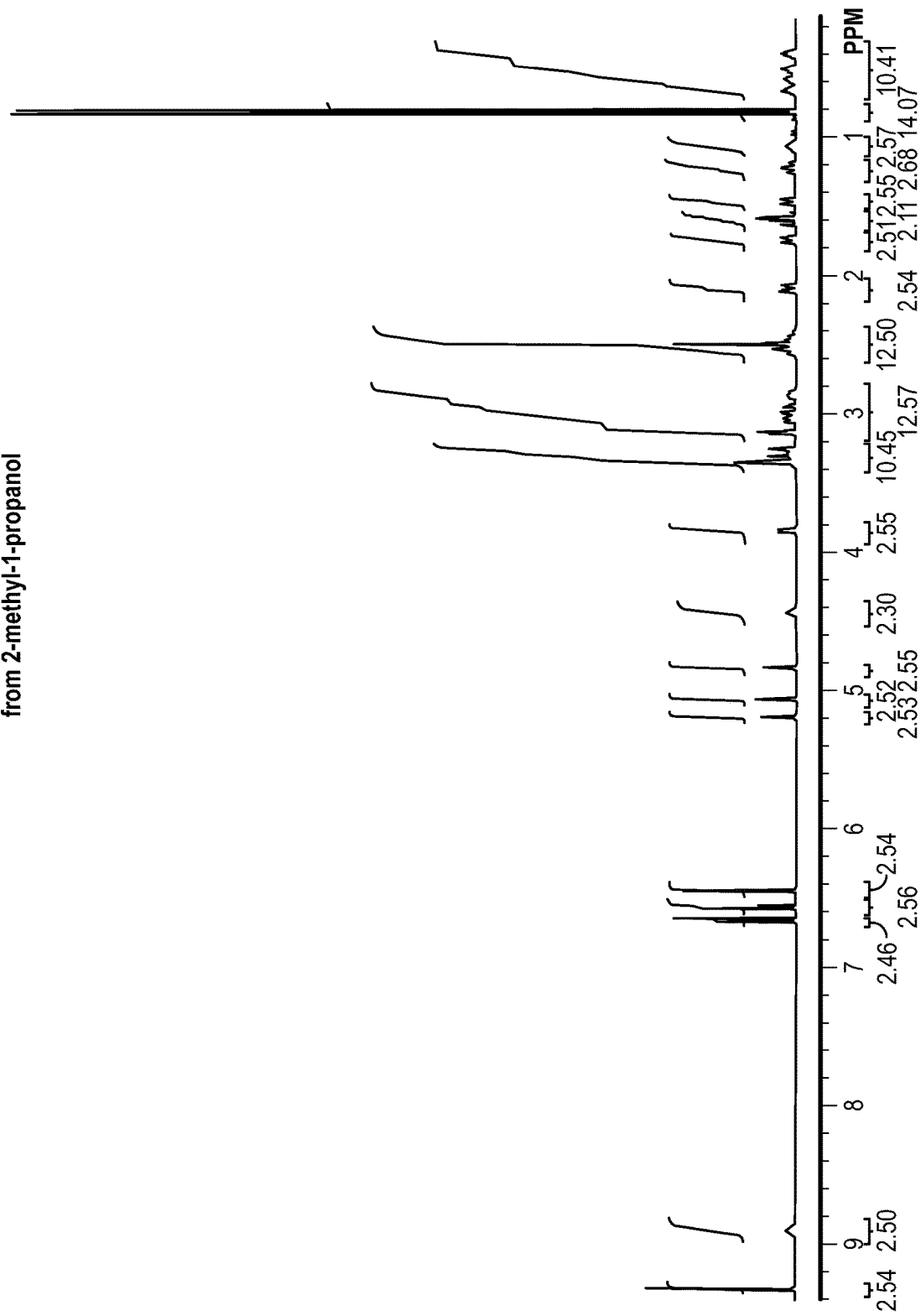
FIG. 12A is a proton nuclear magnetic resonance (NMR) spectrum measured from a sample of crystalline Nalmefene HCl recrystallized from a solution of 2-methyl-1-propanol, Water, and Nalmefene HCl.
Figure 12C:
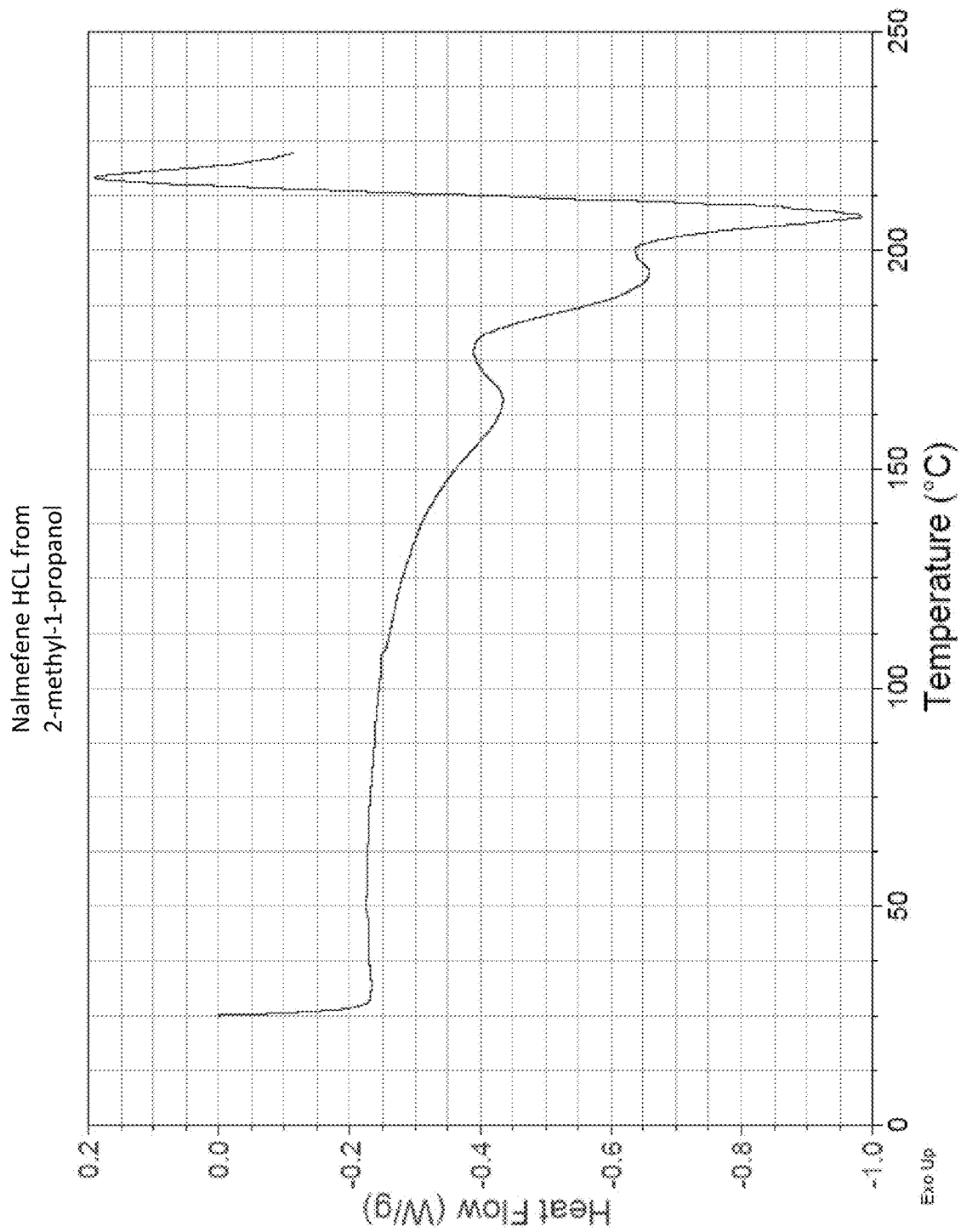
FIG. 12C is a Differential Scanning calorimetry (DC) plot measured from a sample of crystalline Nalmefene HCl recrystallized from a solution of 2-methyl-1-propanol, Water, and Nalmefene HCl.
Figure 12D:
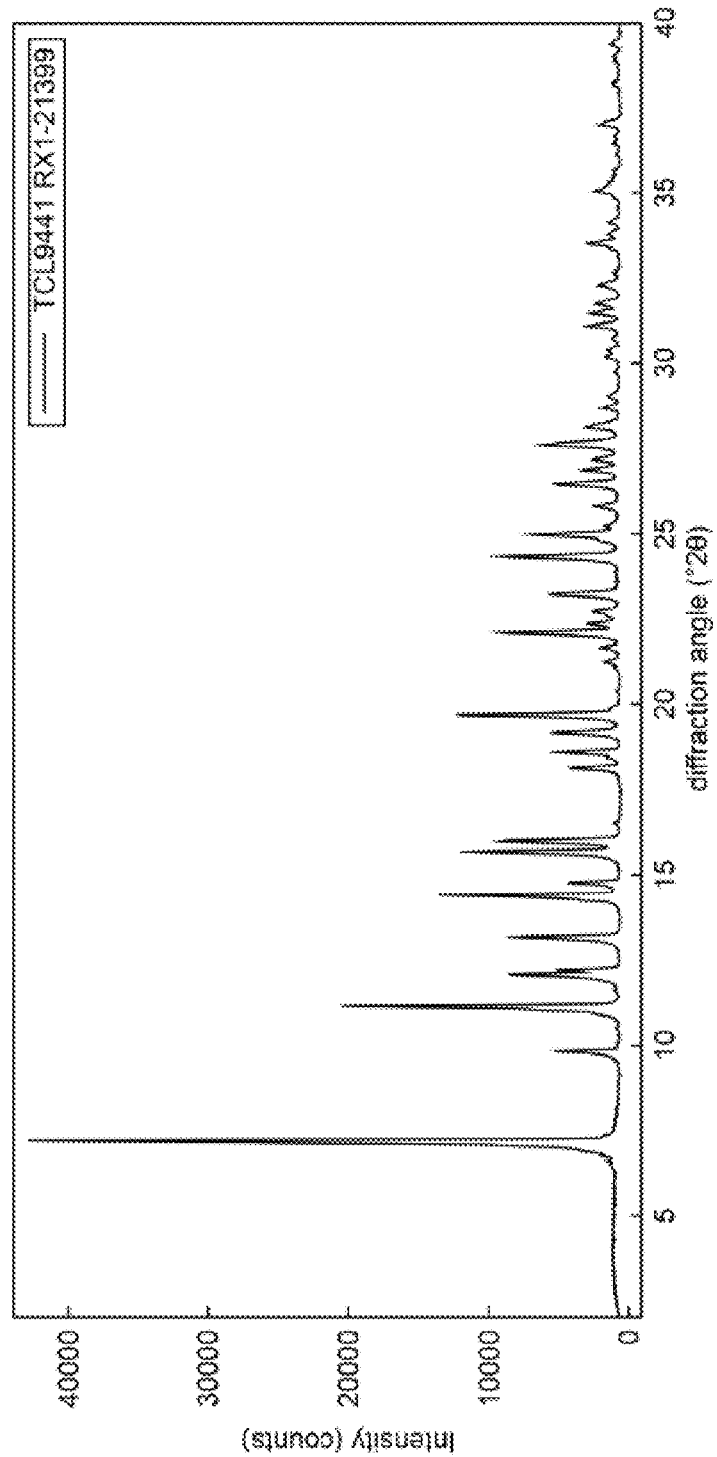
FIG. 12D is an x-ray diffraction spectrum measured from a sample of crystalline Nalmefene HCl recrystallized from a solution of 2-methyl-1-propanol, Water, and Nalmefene HCl.
Figure 13A:
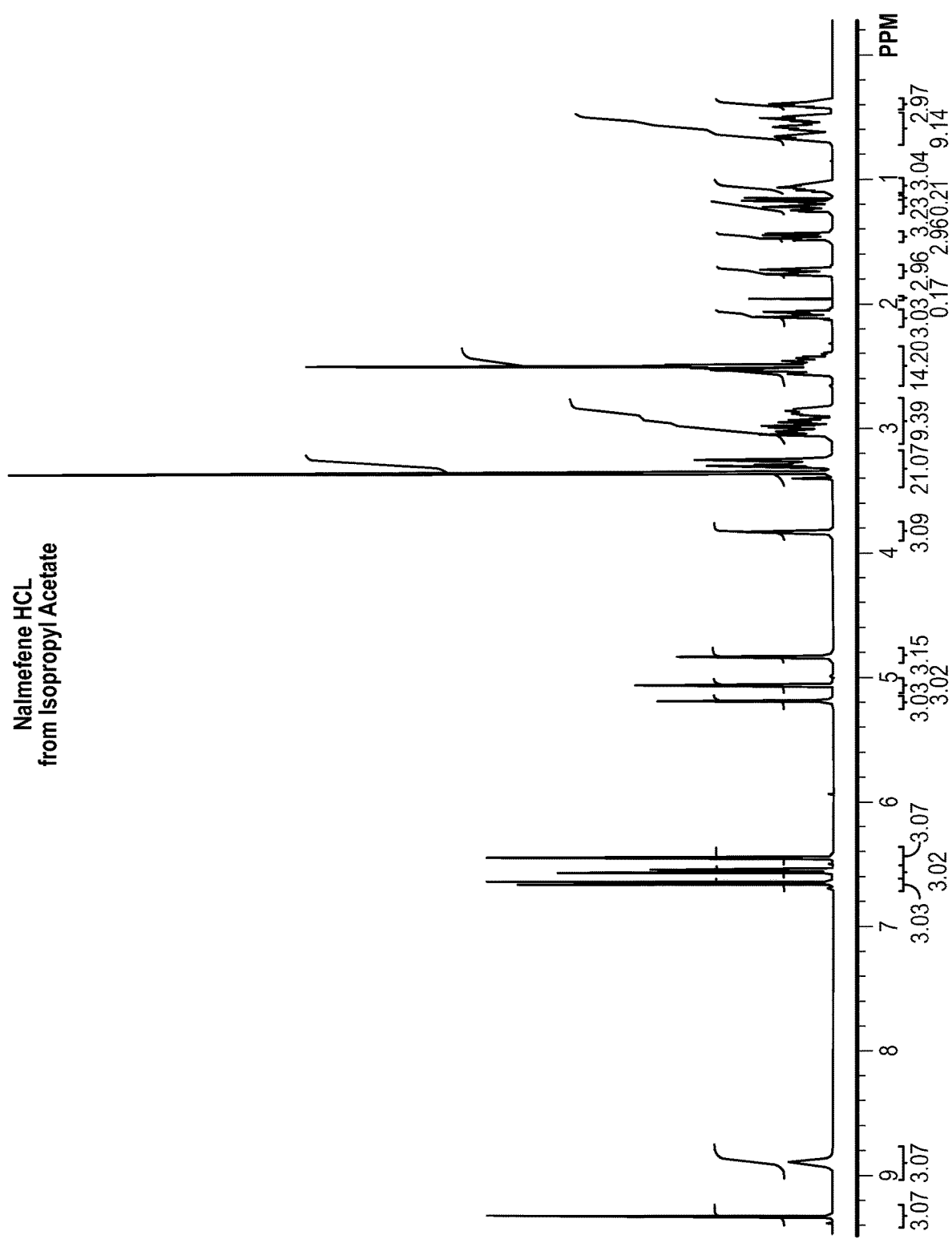
FIG. 13A is a proton nuclear magnetic resonance (NMR) spectrum measured from a sample of crystalline Nalmefene HCl recrystallized from a solution of isopropyl acetate, Water, and Nalmefene HCl.
Figure 13C:
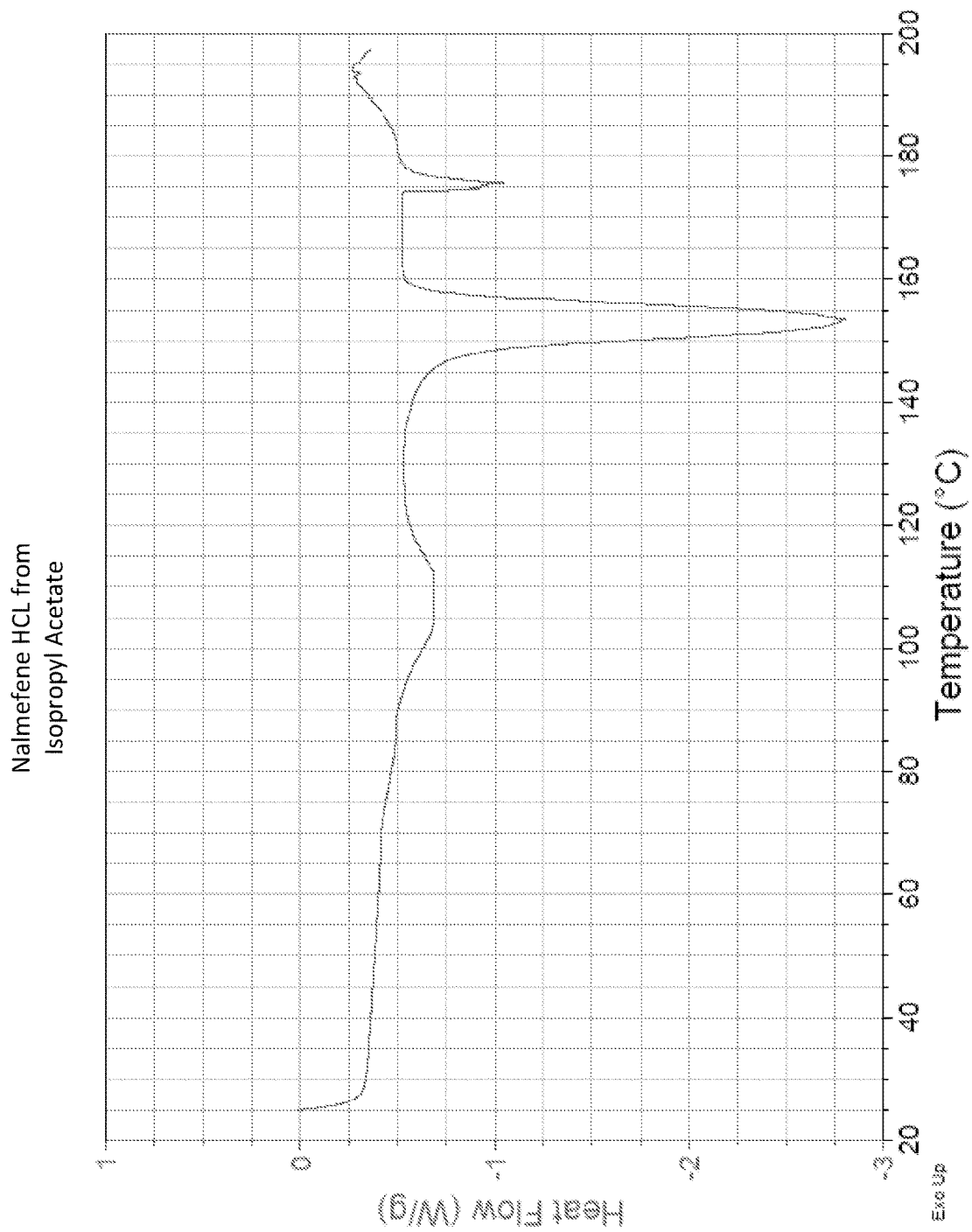
FIG. 13C is a Differential Scanning calorimetry (DC) plot measured from a sample of crystalline Nalmefene HCl recrystallized from a solution of isopropyl acetate, Water, and Nalmefene HCl.
Figure 13D:
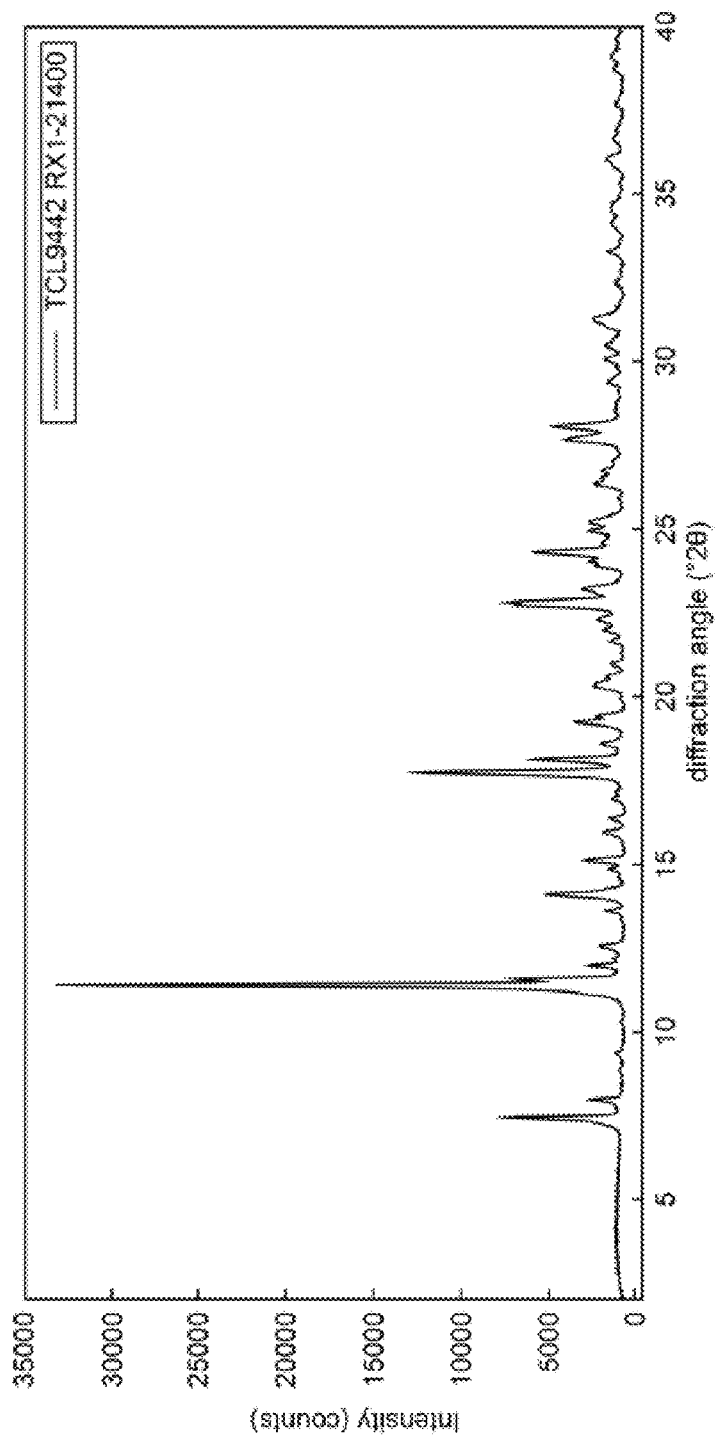
FIG. 13D is an x-ray diffraction spectrum measured from a sample of crystalline Nalmefene HCl recrystallized from a solution of isopropyl acetate, Water, and Nalmefene HCl.

DSC:

Each of the samples was analyzed by differential scanning calorimetry (DCS) using a TA instruments Q100 MDSC. To perform the analysis ~5-15 mg of each sample was weighted into an aluminum pan and crimped. The samples were then placed into the furnace of the DLC. The furnace was purged with 50 ml/min of nitrogen and the samples were heated to 250° C. at a thermal ramp rate of 10° C./min. The heat flow versus temperature of each sample was measured and plotted, and the results are shown in FIGS. 2C, 3C, 4C . . . 13C. From the data, it was observed that all the dihydrate samples showed a major (most intense) endotherm at about 148° C. to about 156° C., as compared to relatively less intense endotherms at higher temperatures. This suggests that the dihydrate samples (4a, 6, 7, and 9-11) are all the same polymorph. Fewer similarities are present in the monohydrate, monosolvate samples, suggesting that those samples are different than the dihydrate samples and are different from one another. The data is summarized in table 8 below

TABLE 8

DSC endotherms for Nalmefene HC1 samples

| # | Solvent | Mols H$_2$O | Mols Solvent | Observed Endotherms (° C.) |
|---|---|---|---|---|
| 1 | Ethanol | 1.01 | 0.96 | 184,489 |
| 2 | 1-Butanol | 0.43 | 1.53 | 114, 201, 209 |
| 3 | 2-Butanone | 1.59 | 0.36 | 157 |
| 4a | n-Butyl acetate | 1.94 | 0.05 | 152, 168 |
| 5 | 2-Propanol | 0.98 | 0.92 | 196, 205 |
| 6 | Heptane | 1.96 | 0.01 | 154, 177, 182 |
| 7 | Ethyl Acetate | 1.85 | 0.12 | 150, 171 |
| 8 | 1-Propanol | 1.01 | 0.89 | >195 |
| 9 | Isopropyl acetate | 2.14 | 0.01 | 153, 175 |
| 10 | Isobutyl acetate | 2.07 | 0.02 | 152, 173, 211 |
| 11 | N-propyl acetate | 2.03 | 0.05 | 150, 165, 190 |
| 12 | 2-Methyl-1-propanol | 0.99 | 0.97 | 162, 196, 207 |

Figure 2D:
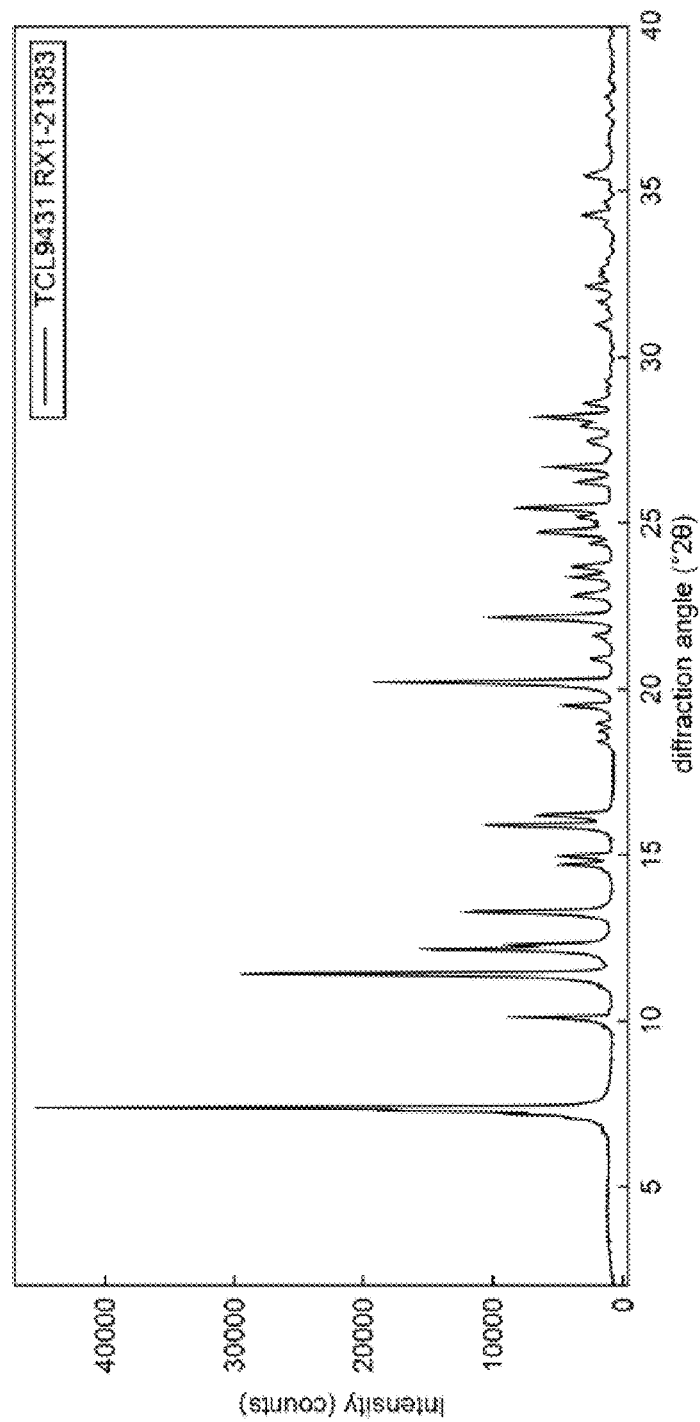
FIG. 2D is an x-ray diffraction spectrum measured from a sample of crystalline Nalmefene HCl recrystallized from a mixture of Ethanol, Water, and Nalmefene HCl.

XRPD:

Each of the samples were analyzed using x-ray power diffraction (XRPD) using a Rigaku Smart-Lab x-ray diffraction system. The obtained XRPD spectra are provided in FIGS. 2DS, 3D, 4D . . . 13D. All the XRPD spectra were compared to a known XRPD spectra of Nalmefene HCl dihydrate. The XRPD spectra for Samples 4a, 6, 7, and 9-11 matched the known XRPD spectra for the dihydrate, indicating that such samples were crystalline Nalmefene HCl dihydrate. The other samples did not match the known XRPD spectrum for the dihydrate, and so are believed to correspond to the monohydrate, monosolvate, as supported by other measurements. The data is summarized in table 9 below.

TABLE 9

XRPD analysis of obtained Nalmefene HCl samples

| # | Solvent | Mols H$_2$O | Mols Solvent | Matched Known DH Spectrum |
|---|---|---|---|---|
| 1 | Ethanol | 1.01 | 0.96 | No |
| 2 | 1-Butanol | 0.43 | 1.53 | No |
| 3 | 2-Butanone | 1.59 | 0.36 | No |
| 4a | n-Butyl acetate | 1.94 | 0.05 | Yes |
| 5 | 2-Propanol | 0.98 | 0.92 | No |
| 6 | Heptane | 1.96 | 0.01 | Yes |
| 7 | Ethyl Acetate | 1.85 | 0.12 | Yes |
| 8 | 1-Propanol | 1.01 | 0.89 | No |
| 9 | Isopropyl acetate | 2.14 | 0.01 | Yes |
| 10 | Isobutyl acetate | 2.07 | 0.02 | Yes |
| 11 | N-propyl acetate | 2.03 | 0.05 | Yes |
| 12 | 2-Methyl-1-propanol | 0.99 | 0.97 | No |

Without wishing to be bound by theory, the inventors believe that solvents with a molar volume less than or equal to 95 cm$^3$ are small enough to be entrapped in the crystalline lattice of Nalmefene HCl, making such solvents more difficult to remove by conventional processes such as vacuum drying. In contrast, solvents with a molar volume of 98 cm$^3$ or greater are believed to be too large to fit into the crystalline lattice of Nalmefene HCl.

Additional Examples

The following are additional example embodiments of the present disclosure

Example 1: According to this example there is provided a method of forming Nalmefene hydrochloride (HCl) (17-(cyclopropylmethyl)-4,5-alpha-epoxy-6-methylenemorphinan-3,14-diol hydrochloride), including: forming a first mixture including Nalmefene HCl, a first amount of a first solvent, and water; and performing at least one solvent removal operation to remove the first solvent and water from the mixture to form crystalline Nalmefene HCl; wherein a residual amount of the first solvent in the crystalline Nalmefene HCl is less than or equal to about 15 weight %.

Example 2: This example includes any or all the features of example 1, wherein the first solvent is an organic solvent with a molar volume of greater than or equal to 98 cm$^3$.

Example 3: This example includes any or all the features of example 1, wherein the first solvent is selected from the group consisting of heptane, ethyl acetate, n-butyl acetate, isobutyl acetate, n-propyl acetate, isopropyl acetate, or a combination of two or more thereof.

Example 4: This example includes any or all the features of example 1, wherein the residual amount of the first solvent in the crystalline Nalmefene HCl is less than or equal to 5 weight %.

Example 5: This example includes any or all the features of example 1, wherein the residual amount of the first solvent in the crystalline Nalmefene HCl is less than or equal to 2.5 weight %.

Example 6: This example includes any or all the features of example 1, wherein the residual amount of the first solvent in the crystalline Nalmefene HCl is less than or equal to 1.4 weight %.

Example 7: This example includes any or all the features of example 1, wherein the crystalline Nalmefene HCl consists essentially of crystalline Nalmefene HCl dihydrate.

Example 8: This example includes any or all the features of example 2, wherein the crystalline Nalmefene HCl consists essentially of crystalline Nalmefene HCl dihydrate.

Example 9: This example includes any or all the features of example 3, wherein the crystalline Nalmefene HCl consists essentially of crystalline Nalmefene HCl dihydrate.

Example 10: This example includes any or all the features of example 1, wherein performing said at least one solvent removal operation includes: removing part of the first solvent from the first mixture to produce a second mixture including the Nalmefene HCl and a second amount of the first solvent that is less than the first amount of the first solvent; adding first solvent to the second mixture to form a third mixture that includes a third amount of the first solvent; and removing substantially all the first solvent from the third mixture to form the crystalline Nalmefene HCl.

Example 11: This example includes any or all the features of example 1, wherein the first mixture is an azeotrope of the first solvent and the water.

Example 12: This example includes any or all the features of example 1, wherein the first solvent is an organic solvent with a molar volume of about 55 to 95 cm$^3$.

Example 13: This example includes any or all the features of example 12, wherein the first solvent is selected from the group consisting of ethanol, 2-propanol, 1-propanol, 2-methyl-1-propanol or a combination of two or more thereof.

Example 14: This example includes any or all the features of example 12 wherein the residual amount of the first solvent in the crystalline Nalmefene HCl ranges from 8 to 15 weight %.

Example 15: This example includes any or all the features of example 12, wherein the residual amount of the first solvent in the crystalline Nalmefene HCl ranges from about 9.8 to 14.9 weight %.

Example 16: This example includes any or all the features of example 1, wherein the crystalline Nalmefene HCl consists essentially of Nalmefene HCl monohydrate monosolvate.

Example 17: This example includes any or all the features of example 12, wherein the crystalline Nalmefene HCl consists essentially of Nalmefene HCl monohydrate monosolvate.

Example 18: This example includes any or all the features of example 13, wherein the crystalline Nalmefene HCl consists essentially of Nalmefene HCl monohydrate monosolvate.

Example 19: According to this example there is provided crystalline Nalmefene HCl (17-(cyclopropylmethyl)-4,5-alpha-epoxy-6-methylenemorphinan-3,14-diol hydrochloride) including less than 15 weight % of a residual amount of a first solvent.

Example 20: This example includes any or all the features of \example 19, wherein the first solvent is an organic solvent with a molecular volume molar volume of greater than or equal to about 98 $cm^3$.

Example 21: This example includes any or all the features of example 20, wherein the first solvent is selected from the group consisting of heptane, ethyl acetate, n-butyl acetate, isobutyl acetate, n-propyl acetate, isopropyl acetate, or a combination of two or more thereof.

Example 22: This example includes any or all the features of example 20, wherein the residual amount of the first solvent is less than or equal to 5 weight %.

Example 23: This example includes any or all the features of example 20, wherein the residual amount of the first solvent is less than or equal to 2.5 weight %.

Example 24: This example includes any or all the features of example 20, wherein the crystalline Nalmefene HCl consists essentially of Nalmefene HCl dihydrate.

Example 25: This example includes any or all the features of example 19, wherein the first solvent is an organic solvent with a molecular volume molar volume in a range of 55 to 95 $cm^3$.

Example 26: This example includes any or all the features of example 25, wherein the first solvent is selected from the group consisting of ethanol, 2-propanol, 1-propanol, 2-methyl-1-propanol or a combination of two or more thereof.

Example 27: This example includes any or all the features of example 25 wherein the residual amount of the first solvent in the crystalline Nalmefene HCl ranges from 8 to 15 weight %.

Example 28: This example includes any or all the features of example 25, wherein the residual amount of the first solvent in the crystalline Nalmefene HCl ranges from about 9.8 to 14.9 weight %.

Example 29: This example includes any or all the features of example 28, wherein the crystalline Nalmefene HCl consists essentially of Nalmefene HCl monohydrate monosolvate.

As may be appreciated by the foregoing, the methods of the present disclosure enable a relatively simple crystallization process for controlling (e.g., reducing) the amount of residual solvent contained in crystalline Nalmefene HCl by appropriate selection of recrystallization solvent. In addition, crystallization of a monosolvate, monohydrate polymorph or a dihydrate polymorph can be attained by selection of an appropriate recrystallization solvent. Moreover, the processes described herein enable a relatively simple method for purifying crystalline Nalmefene HCl that is contaminated with an undesirable solvent having a relatively small molar volume (e.g., less than or equal to 95 $cm^3$). Specifically, using the processes described herein, the contaminated salt may be recrystallized into the dihydrate form from an azeotrope of water and an organic solvent having a molar volume greater than or equal to 98 $cm^3$. During that process, it is believed that the smaller organic solvent (i.e., the contaminant) is replaced by water, and the larger solvent in the azeotrope is too large to fit in the crystalline lattice of Nalmefene HCl. The processes described herein can also produce nearly quantitative yields, indicating that they are an efficient way to remove undesirable residual solvents from Nalmefene HCl.

While the present disclosure is described herein with reference to illustrative embodiments for particular applications, such embodiments are exemplary only and that the invention as defined by the appended claims is not limited thereto. Those skilled in the relevant art(s) with access to the teachings provided herein will recognize additional modifications, applications, and embodiments within the scope of this disclosure, and additional fields in which embodiments of the present disclosure would be of utility.

As used herein the terms "substantially" and "about" when used in connection with a value or range of values mean plus or minus 5% of the indicated value or the end points of the indicated range. To the extent ranges are recited in the present disclosure, it should be understood that the indicated range(s) is/are not limited to the indicated end points, but rather include each point therein and ranges between any two points therein as though such points and ranges are expressly recited. For example, recitation of the range "1 to 10" should be understood to include 2, 3, 4, 5, 6, 7, 8 etc., as well as the ranges 2-10, 2-9, 2-8 . . . , 3-10, 3-9, 3-8 . . . , 4-10, 4-9, 4-8 . . . , 5-10, 5-9, 5-8 . . . , etc.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents. Various features, aspects, and embodiments have been described herein. The features, aspects, and embodiments are susceptible to combination with one another as well as to variation and modification, as will be understood by those having skill in the art. The present disclosure should, therefore, be considered to encompass such combinations, variations, and modifications.

What is claimed is:

1. A method of forming Nalmefene hydrochloride (HCl) (17-(cyclopropylmethyl)-4,5-alpha-epoxy-6-methylenemorphinan-3,14-diol hydrochloride), comprising:
   forming a first mixture comprising Nalmefene HCl, a first amount of a first solvent, and water; and
   performing at least one solvent removal operation to remove said first solvent and water from said first mixture to form crystalline Nalmefene HCl;
   wherein:
   a residual amount of said first solvent in said crystalline Nalmefene HCl is less than or equal to about 15 weight %; and
   said solvent is an organic solvent with a molar volume greater than or equal to 110 $cm^3$.

2. The method of claim 1, wherein said first solvent is selected from the group consisting of heptane, n butyl acetate, isobutyl acetate, n-propyl acetate, isopropyl acetate, or a combination of two or more thereof.

3. The method of claim 1, wherein said residual amount of said first solvent in said crystalline Nalmefene HCl is less than or equal to 5 weight %.

4. The method of claim 1, wherein said residual amount of said first solvent in said crystalline Nalmefene HCl is less than or equal to 2.5 weight %.

5. The method of claim 1, wherein said residual amount of said first solvent in said crystalline Nalmefene HCl is less than or equal to 1.4 weight %.

6. The method of claim 1, wherein said crystalline Nalmefene HCl consists essentially of crystalline Nalmefene HCl dihydrate.

7. The method of claim 2, wherein said crystalline Nalmefene HCl consists essentially of crystalline Nalmefene HCl dihydrate.

8. The method of claim 1, wherein performing said at least one solvent removal operation comprises:
    removing part of the first solvent from the first mixture to produce a second mixture comprising said Nalmefene HCl and a second amount of said first solvent that is less than the first amount of said first solvent;
    adding first solvent to the second mixture to form a third mixture that comprises said Nalmefene HCl and a third amount of said first solvent; and
    removing substantially all the first solvent from the third mixture to form said crystalline Nalmefene HCl.

9. The method of claim 1, wherein said first mixture is an azeotrope of said first solvent and said water.

10. A method of forming Nalmefene hydrochloride (HCl) (17-(cyclopropylmethyl)-4,5-alpha-epoxy-6-methylenemorphinan-3,14-diol hydrochloride), comprising:
    forming a first mixture comprising Nalmefene HCl, a first amount of a first solvent, and water, wherein said first solvent is an organic solvent with a molar volume of about 55 to 95 cm$^3$; and
    performing at least one solvent removal operation to remove said first solvent and water from said first mixture to form crystalline Nalmefene HCl;
    wherein:
    a residual amount of said first solvent in said crystalline Nalmefene HCl is less than or equal to about 15 weight %; and
    said first solvent is selected from the group consisting of ethanol, 2-propanol, 1-propanol, 2-methyl-1-propanol or a combination of two or more thereof.

11. The method of claim 10 wherein said residual amount of said first solvent in said crystalline Nalmefene HCl ranges from 8 to 15 weight %.

12. The method of claim 10, wherein said residual amount of said first solvent in said crystalline Nalmefene HCl ranges from about 9.8 to 14.9 weight %.

13. The method of claim 10, wherein performing said at least one solvent removal operation comprises:
    removing part of the first solvent from the first mixture to produce a second mixture comprising said Nalmefene HCl and a second amount of said first solvent that is less than the first amount of said first solvent;
    adding first solvent to the second mixture to form a third mixture that comprises said Nalmefene HCl and a third amount of said first solvent; and
    removing substantially all the first solvent from the third mixture to form said crystalline Nalmefene HCl.

14. The method of claim 10, wherein said crystalline Nalmefene HCl consists essentially of Nalmefene HCl monohydrate monosolvate.

15. The method of claim 13, wherein said crystalline Nalmefene HCl consists essentially of Nalmefene HCl monohydrate monosolvate.

16. Crystalline Nalmefene HCl (17-(cyclopropylmethyl)-4,5-alpha-epoxy-6-methylenemorphinan-3,14-diol hydrochloride) comprising less than 15 weight % of a residual amount of a first solvent, wherein said first solvent has a molar volume greater than or equal to about 110 cm$^3$.

17. The crystalline Nalmefene HCl of claim 16, wherein said first solvent is selected from the group consisting of heptane, ethyl acetate, n butyl acetate, isobutyl acetate, n-propyl acetate, isopropyl acetate, or a combination of two or more thereof.

18. The crystalline Nalmefene HCl of claim 16, wherein said residual amount of said first solvent is less than or equal to 5 weight %.

19. The crystalline Nalmefene HCl of claim 16, wherein said residual amount of said first solvent is less than or equal to 2.5 weight %.

20. Crystalline Nalmefene HCl (17-(cyclopropylmethyl)-4,5-alpha-epoxy-6-methylenemorphinan-3,14-diol hydrochloride) comprising less than 15 weight % of a residual amount of a first solvent, wherein said crystalline Nalmefene HCl consists essentially of crystalline Nalmefene HCl dihydrate.

21. Crystalline Nalmefene HCl (17-(cyclopropylmethyl)-4,5-alpha-epoxy-6-methylenemorphinan-3,14-diol hydrochloride) comprising less than 15 weight % of a residual amount of a first solvent, wherein said first solvent is selected from the group consisting of: ethanol, 2-propanol, 1-propanol, 2-methyl-1-propanol or a combination of two or more thereof.

22. The crystalline Nalmefene HCl of claim 21, wherein said crystalline Nalmefene HCl consists essentially of Nalmefene HCl monohydrate monosolvate.

23. The crystalline Nalmefene HCl of claim 21 wherein said residual amount of said first solvent in said crystalline Nalmefene HCl ranges from 8 to 15 weight %.

24. The crystalline Nalmefene HCl of claim 21, wherein said residual amount of said first solvent in said crystalline Nalmefene HCl ranges from about 9.8 to 14.9 weight %.

25. The crystalline Nalmefene HCl of claim 24, wherein said crystalline Nalmefene HCl consists essentially of Nalmefene HCl monohydrate monosolvate.

\* \* \* \* \*